US010189890B2

(12) United States Patent
Sun et al.

(10) Patent No.: US 10,189,890 B2
(45) Date of Patent: Jan. 29, 2019

(54) VARIANTS OF TISSUE INHIBITOR OF METALLOPROTEINASE TYPE THREE (TIMP-3), COMPOSITIONS AND METHODS

(71) Applicant: AMGEN INC., Thousand Oaks, CA (US)

(72) Inventors: Jeonghoon Sun, San Diego, CA (US); Jason Charles O'Neill, Brier, WA (US); Randal R. Ketchem, Snohomish, WA (US); Randy Ira Hecht, Raleigh, NC (US); Edward J. Belouski, Thousand Oaks, CA (US); Mark Leo Michaels, Encino, CA (US)

(73) Assignee: Amgen Inc., Thousand Oaks, CA (US)

( * ) Notice: Subject to any disclaimer, the term of this patent is extended or adjusted under 35 U.S.C. 154(b) by 69 days.

(21) Appl. No.: 14/775,482

(22) PCT Filed: Mar. 13, 2014

(86) PCT No.: PCT/US2014/026811
§ 371 (c)(1),
(2) Date: Sep. 11, 2015

(87) PCT Pub. No.: WO2014/152012
PCT Pub. Date: Sep. 25, 2014

(65) Prior Publication Data

US 2016/0031969 A1 Feb. 4, 2016

Related U.S. Application Data

(60) Provisional application No. 61/782,613, filed on Mar. 14, 2013, provisional application No. 61/798,160, filed on Mar. 15, 2013, provisional application No. 61/802,988, filed on Mar. 18, 2013, provisional application No. 61/940,673, filed on Feb. 17, 2014.

(51) Int. Cl.

| | |
|---|---|
| ***C07K 14/435*** | (2006.01) |
| ***A61K 38/16*** | (2006.01) |
| ***C12N 15/09*** | (2006.01) |
| ***C12N 15/11*** | (2006.01) |
| ***C12N 15/12*** | (2006.01) |
| ***C12N 15/63*** | (2006.01) |
| ***C07K 14/81*** | (2006.01) |
| ***C12N 9/64*** | (2006.01) |
| *A61K 38/00* | (2006.01) |

(52) U.S. Cl.
CPC ........ *C07K 14/8146* (2013.01); *C12N 9/6489* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 2004/0224398 A1 | 11/2004 | Anand-Apte | |
| 2007/0202094 A1 | 8/2007 | Anand-Apte | |
| 2010/0010201 A1 | 1/2010 | Silbiger | |
| 2015/0018747 A1 | 1/2015 | Michal et al. | |

FOREIGN PATENT DOCUMENTS

| | | |
|---|---|---|
| EP | 0648838 A1 | 4/1995 |
| EP | 0648838 B1 | 5/2003 |
| WO | 2007/016482 A2 | 2/2007 |
| WO | 2007/016482 A3 | 2/2007 |
| WO | 2008/109433 A2 | 9/2008 |

OTHER PUBLICATIONS

Bowie et al. Deciphering the message in protein sequences: tolerance to amino acid substitutions. Science, (Mar. 16, 1990) 247 (4948) 1306-10.*

Lee et al. Tailoring tissue inhibitor of metalloproteinases-3 to overcome the weakening effects of the cysteine-rich domains of tumour necrosis factor-alpha converting enzyme. Biochem J. Apr. 15, 2003;371(Pt 2):369-76.*

Ngo et al., in the Protein Folding Problem and Tertiary Structure Prediction, Merz and Le Grand (Eds), Aug. 1994, Springer Verlag, pp. 433 and 492-495.*

Umlauf et al. Cartilage biology, pathology, and repair. Cell Mol Life Sci. Dec. 2010;67(24):4197-211. Epub Aug. 25, 2010.*

Langton, K.P. et al., "Localization of the Functional Domains of Human Tissue Inhibitor of Metalloproteinases-3 and the Effects of a Sorsby's Fundus Dystrophy Mutation*," The Journal of Biological Chemistry, vol. 273, No. 27; pp. 16778-16781 (1998).

Database XP002725522, http://ibis/exam/dbfetch.jsp?UNITPROT:L5KF25, May 14, 2014.

Database XP55122276A, http://www.unitprot.org/unitprot/B2KII1; Last modified Apr. 16, 2014. Version 22. "Tissue inhibitor of metalloproteinsase 3 (Predicted)—TIMP3".

Anonymous: "Tissue inhibitor of metalloproteinase 3 (Predicted)—TIMP3—*Rhinolophus ferrumequinum* (Greater horseshoe bat)" Jun. 10, 2008 (Jun. 10, 2008), XP055122276, Retrieved from the Internet: URL:http://www.uniprot.org/uniprot/B2KII1 [retrieved on Jun. 10, 2014] the whole document, as notated on International Search Report (please see D3 below); retrieval date of the attached reference Jul. 26, 2017.

Database UniProt [Online] Mar. 6, 2013 (Mar. 6, 2013), "SubName: Full=Metalloproteinase inhibitor 3;" XP002725522, retrieved from EBI accession No. UNI PROT: L5KF25; Database accession No. L5KF25 the whole document, as notated on the International Search Report (please see D3 below); http://www.uniprot.org/uniprot/L5KF25; retrieval date of the attached reference Jul. 26, 2017.

International Search Report, Patent Cooperation Treaty, Date of the actual completion of the international search Aug. 26, 2015; dated Sep. 2, 2015; Authorized officer: Landre, Julien.

(Continued)

*Primary Examiner* — Christine J Saoud
*Assistant Examiner* — Jon M Lockard
(74) *Attorney, Agent, or Firm* — Lisa E. Alexander

(57) ABSTRACT

There are disclosed TIMP-3 muteins, variants and derivatives, nucleic acids encoding them, and methods of making and using them.

6 Claims, 6 Drawing Sheets

Specification includes a Sequence Listing.

(56) References Cited

OTHER PUBLICATIONS

Apte S. S. et al., The gene structure of tissue inhibitor of metalloproteinases (TIMP)-3 and its inhibitory activities define the distinct TIMP gene family. *J. Biol. Chem.*, 1995, vol. 270, No. 24, pp. 14313-14318.

Fingleton B., MMPs as therapeutic targets—still a viable option?, Semin Cell Dev. Biol. , Feb. 2008, vol. 19, No. 1, pp. 61-68.

* cited by examiner

```
1          11         21         31         41         51
MTPWLGLIVL LGSWSLGDWG AEACTCSPSH PQDAFCNSDI VIRAKVVGKK LVKEGPFGTL
XXXXXXXXXX XXXXXXXXXX XXXCTCSPSH PQDAFCNSDI VIRAXVXGXX XXXEGXXXTL

61         71         81         91         101        111
VYTIKQMKMY RGFTKMPHVQ YIHTEASESL CGLKLEVNKY QYLLTGRVYD GKMYTGLCNF
VYXIXQXXMY RGFXXMXXVX YIHTEASESL CGLXLXXXXY QYLLTGRVYX GXMYTGLCNF

121        131        141        151        161        171
VERWDQLTLS QRKGLNYRYH LGCNCKIKSC YYLPCFVTSK NECLWTDMLS NFGYPGYQSK
VERWDXLTLS QRXGLNYXYX LGCNCKIKSC YYLPCFVXSX NECLWXDXLS NFXYPGYQSK

181        191        201        211
HYACIRQKGG YCSWYRGWAP PDKSIINATD P
XYXCIXQXGG YCSWYRGWAP XDXSIINXTD P
```

Figure 1

```
1          11         21         31         41         51
MTPWLGLIVL LGSWSLGDWG AEACTCSPSH PQDAFCNSDI VIRAKVVGKK LVKEGPFGTL
                         *X*XX** *X******X* **X*XX*XX* X*XX******

61         71         81         91         101        111
VYTIKQMKMY RGFTKMPHVQ YIHTEASESL CGLKLEVNKY QYLLTGRVYD GKMYTGLCNF
**X***XX** *******X** ********** *****X**** ********** **********

121        131        141        151        161        171
VERWDQLTLS QRKGLNYRYH LGCNCKIKSC YYLPCFVTSK NECLWTDMLS NFGYPGYQSK
********** ********** ********** ********** ********** **********

181        191        201        211
HYACIRQKGG YCSWYRGWAP PDKSIINATD P
********** ********** *X****X*** *
```

Figure 2

```
1          11         21         31         41         51
MTPWLGLIVL LGSWSLGDWG AEACTCSPSH PQDAFCNSDI VIRAKVVGKK LVKEGPFGTL
XXXXXXXXXX XXXXXXXXXX XXXCTCSPSH PQDAFCNSDI VIXAXVVGKK LVXXGPFGTL

61         71         81         91         101        111
VYTIKQMKMY RGFTKMPHVQ YIHTEASESL CGLKLEVNKY QYLLTGRVYD GKMYTGLCNF
VYTIXQXXMY XXXXXXXXVQ YIHTEASESL CGLKLEVNKY QYLLTGRVYD GKMYTGLCNF

121        131        141
VERWDQLTLS QRKGLNYRYH LGCN
VERWDQLTLS QRKGLNYRYH LGCN
```

Figure 4

```
1          11         21         31         41         51
MTPWLGLIVL LGSWSLGDWG AEACTCSPSH PQDAFCNSDI VIRAKVVGKK LVKEGPFGTL
XXXXXXXXXX XXXXXXXXXX XXXCXXXXXX XXDAXXXSXI XXXAXXVXXK XVXXGXFGTX

61         71         81         91         101        111
VYTIKQMKMY RGFTKMPHVQ YIHTEASESL CGLKLEVNKY QYLLTGRVYD GKMYTGLCNF
XYXIKQMKMY RGFXKMPXVX YIHTEASESL CGLKLEVNKY QYLLTGRVYD GKMYTXLXXF

121        131        141
VERWDQLTLS QRKGLNYRYH LGCN
VERWDQLTLS QRKGLNYRYH LGXX
```

Figure 5

```
        1                                                  50
TIMP-2  MGAAARTLRL ALGLLLLATL LRP..ADACS CSPVHPQQAF CNADVVIRAK
TIMP-3  ~~~~~M PW  G IV  GSWS  GDWG E  T    S   D      S I
              *  *  *  **     *    * **  *** *** ** ** * *****

        51                                                100
TIMP-2  AVSEKEVDSG NDIYGNPIKR IQYEIKQIKM FKGPEK..DI EFIYTAPSSA
TIMP-3  V GK L KE  ...... FGT LV T   M   YR FT MPHV QY H EA ES
         *  * *  *       *      * *** **   *  *       * *  *

        101                                               150
TIMP-2  VCGVSLDVGG KKEYLIAGKA EGDGKMHITL CDFIVPWDTL STTQKKSLNH
TIMP-3  L  LK E .N  YQ  LT RV Y.    YTG   N VER  Q  TLS R G  Y
         **  * *   *  **  *     ****   * * *   ** *    * * **

        151                                               200
TIMP-2  RYQMGCECKI TRCPMIPCYI SSPDECLWMD WVTEKNINGH QAKFFACIKR
TIMP-3    HL  N    KS YYL  FV T KN    T  MLSNFGYP Y  S HY   RQ
        **  ** ***   *   **    *  **** *         *  * *  ***

        201                    224
TIMP-2  SDGSCAWYRG AAPPKQEFLD IEDP
TIMP-3  KG Y S     W   DKSIIN AT
          * * ****  ***         **
```

Figure 6

SEQUENCE LISTING

```
<160> NUMBER OF SEQ ID NOS: 99

<210> SEQ ID NO 1
<211> LENGTH: 633
<212> TYPE: DNA
<213> ORGANISM: Homo sapiens

<400> SEQUENCE: 1

atgacccctt ggctcgggct catcgtgctc ctgggcagct ggagcctggg ggactggggc     60

gccgaggcgt gcacatgctc gcccagccac ccccaggacg ccttctgcaa ctccgacatc    120

gtgatccggg ccaaggtggt ggggaagaag ctggtaaagg aggggccctt cggcacgctg    180

gtctacacca tcaagcagat gaagatgtac cgaggcttca ccaagatgcc ccatgtgcag    240

tacatccaca cggaagcttc cgagagtctc tgtggcctta agctggaggt caacaagtac    300

cagtacctgc tgacaggtcg cgtctatgat ggcaagatgt acacggggct gtgcaacttc    360

gtggagaggt gggaccagct caccctctcc cagcgcaagg ggctgaacta tcggtatcac    420

ctgggttgta actgcaagat caagtcctgc tactacctgc cttgctttgt gacttccaag    480

aacgagtgtc tctggaccga catgctctcc aatttcggtt accctggcta ccagtccaaa    540

cactacgcct gcatccggca gaagggcggc tactgcagct ggtaccgagg atgggccccc    600

ccggataaaa gcatcatcaa tgccacagac ccc                                 633


<210> SEQ ID NO 2
<211> LENGTH: 211
<212> TYPE: PRT
<213> ORGANISM: Homo sapiens

<400> SEQUENCE: 2

Met Thr Pro Trp Leu Gly Leu Ile Val Leu Leu Gly Ser Trp Ser Leu
1               5                   10                  15

Gly Asp Trp Gly Ala Glu Ala Cys Thr Cys Ser Pro Ser His Pro Gln
```

-continued

```
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 3
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
```

<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide
<220> FEATURE:
<221> NAME/KEY: MOD_RES
<222> LOCATION: (45)..(45)
<223> OTHER INFORMATION: Lys, Glu, Asn or Ser
<220> FEATURE:
<221> NAME/KEY: MOD_RES
<222> LOCATION: (47)..(47)
<223> OTHER INFORMATION: Val or Thr
<220> FEATURE:
<221> NAME/KEY: MOD_RES
<222> LOCATION: (49)..(49)
<223> OTHER INFORMATION: Lys, Glu, Asn or Ser
<220> FEATURE:
<221> NAME/KEY: MOD_RES
<222> LOCATION: (50)..(50)
<223> OTHER INFORMATION: Lys or Asn
<220> FEATURE:
<221> NAME/KEY: MOD_RES
<222> LOCATION: (51)..(51)
<223> OTHER INFORMATION: Leu, Asn or Thr
<220> FEATURE:
<221> NAME/KEY: MOD_RES
<222> LOCATION: (52)..(52)
<223> OTHER INFORMATION: Val or Thr
<220> FEATURE:
<221> NAME/KEY: MOD_RES
<222> LOCATION: (53)..(53)
<223> OTHER INFORMATION: Lys or Thr
<220> FEATURE:
<221> NAME/KEY: MOD_RES
<222> LOCATION: (56)..(56)
<223> OTHER INFORMATION: Pro or Asn
<220> FEATURE:
<221> NAME/KEY: MOD_RES
<222> LOCATION: (57)..(57)
<223> OTHER INFORMATION: Phe or Asn
<220> FEATURE:
<221> NAME/KEY: MOD_RES
<222> LOCATION: (58)..(58)
<223> OTHER INFORMATION: Gly or Thr
<220> FEATURE:
<221> NAME/KEY: MOD_RES
<222> LOCATION: (63)..(63)
<223> OTHER INFORMATION: Thr, Glu or Asn
<220> FEATURE:
<221> NAME/KEY: MOD_RES
<222> LOCATION: (65)..(65)
<223> OTHER INFORMATION: Lys, Thr or Asn
<220> FEATURE:
<221> NAME/KEY: MOD_RES
<222> LOCATION: (67)..(67)
<223> OTHER INFORMATION: Met or Thr
<220> FEATURE:
<221> NAME/KEY: MOD_RES
<222> LOCATION: (68)..(68)
<223> OTHER INFORMATION: Lys or Ser
<220> FEATURE:
<221> NAME/KEY: MOD_RES
<222> LOCATION: (74)..(74)
<223> OTHER INFORMATION: Thr or Glu
<220> FEATURE:
<221> NAME/KEY: MOD_RES
<222> LOCATION: (75)..(75)
<223> OTHER INFORMATION: Lys or Asn
<220> FEATURE:
<221> NAME/KEY: MOD_RES
<222> LOCATION: (77)..(77)
<223> OTHER INFORMATION: Pro or Thr
<220> FEATURE:
<221> NAME/KEY: MOD_RES
<222> LOCATION: (78)..(78)
<223> OTHER INFORMATION: His, Asp, Glu or Asn
<220> FEATURE:
<221> NAME/KEY: MOD_RES
<222> LOCATION: (80)..(80)
<223> OTHER INFORMATION: Gln, Glu or Thr
<220> FEATURE:
<221> NAME/KEY: MOD_RES
<222> LOCATION: (94)..(94)
<223> OTHER INFORMATION: Lys or Asn
<220> FEATURE:

<221> NAME/KEY: MOD_RES
<222> LOCATION: (96)..(96)
<223> OTHER INFORMATION: Glu, Thr or Asn
<220> FEATURE:
<221> NAME/KEY: MOD_RES
<222> LOCATION: (97)..(97)
<223> OTHER INFORMATION: Val or Asn
<220> FEATURE:
<221> NAME/KEY: MOD_RES
<222> LOCATION: (98)..(98)
<223> OTHER INFORMATION: Asn or Thr
<220> FEATURE:
<221> NAME/KEY: MOD_RES
<222> LOCATION: (99)..(99)
<223> OTHER INFORMATION: Lys or Thr
<220> FEATURE:
<221> NAME/KEY: MOD_RES
<222> LOCATION: (110)..(110)
<223> OTHER INFORMATION: Asp or Asn
<220> FEATURE:
<221> NAME/KEY: MOD_RES
<222> LOCATION: (112)..(112)
<223> OTHER INFORMATION: Lys or Thr
<220> FEATURE:
<221> NAME/KEY: MOD_RES
<222> LOCATION: (126)..(126)
<223> OTHER INFORMATION: Gln or Asn
<220> FEATURE:
<221> NAME/KEY: MOD_RES
<222> LOCATION: (133)..(133)
<223> OTHER INFORMATION: Lys or Ser
<220> FEATURE:
<221> NAME/KEY: MOD_RES
<222> LOCATION: (138)..(138)
<223> OTHER INFORMATION: Arg, Asn or Thr
<220> FEATURE:
<221> NAME/KEY: MOD_RES
<222> LOCATION: (140)..(140)
<223> OTHER INFORMATION: His or Thr
<220> FEATURE:
<221> NAME/KEY: MOD_RES
<222> LOCATION: (158)..(158)
<223> OTHER INFORMATION: Thr or Asn
<220> FEATURE:
<221> NAME/KEY: MOD_RES
<222> LOCATION: (160)..(160)
<223> OTHER INFORMATION: Lys or Thr
<220> FEATURE:
<221> NAME/KEY: MOD_RES
<222> LOCATION: (166)..(166)
<223> OTHER INFORMATION: Thr or Asn
<220> FEATURE:
<221> NAME/KEY: MOD_RES
<222> LOCATION: (168)..(168)
<223> OTHER INFORMATION: Met or Thr
<220> FEATURE:
<221> NAME/KEY: MOD_RES
<222> LOCATION: (173)..(173)
<223> OTHER INFORMATION: Gly or Thr
<220> FEATURE:
<221> NAME/KEY: MOD_RES
<222> LOCATION: (181)..(181)
<223> OTHER INFORMATION: His or Asn
<220> FEATURE:
<221> NAME/KEY: MOD_RES
<222> LOCATION: (183)..(183)
<223> OTHER INFORMATION: Ala or Thr
<220> FEATURE:
<221> NAME/KEY: MOD_RES
<222> LOCATION: (186)..(186)
<223> OTHER INFORMATION: Arg or Asn
<220> FEATURE:
<221> NAME/KEY: MOD_RES
<222> LOCATION: (188)..(188)
<223> OTHER INFORMATION: Lys or Thr
<220> FEATURE:
<221> NAME/KEY: MOD_RES
<222> LOCATION: (201)..(201)
<223> OTHER INFORMATION: Pro or Asn

<220> FEATURE:
<221> NAME/KEY: MOD_RES
<222> LOCATION: (203)..(203)
<223> OTHER INFORMATION: Lys or Thr
<220> FEATURE:
<221> NAME/KEY: MOD_RES
<222> LOCATION: (208)..(208)
<223> OTHER INFORMATION: Ala, Val or Tyr

<400> SEQUENCE: 3

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Xaa Val Xaa Gly
        35                  40                  45

Xaa Xaa Xaa Xaa Xaa Glu Gly Xaa Xaa Xaa Thr Leu Val Tyr Xaa Ile
    50                  55                  60

Xaa Gln Xaa Xaa Met Tyr Arg Gly Phe Xaa Xaa Met Xaa Xaa Val Xaa
65                  70                  75                  80

Tyr Ile His Thr Glu Ala Ser Glu Ser Leu Cys Gly Leu Xaa Leu Xaa
                85                  90                  95

Xaa Xaa Xaa Tyr Gln Tyr Leu Leu Thr Gly Arg Val Tyr Xaa Gly Xaa
            100                 105                 110

Met Tyr Thr Gly Leu Cys Asn Phe Val Glu Arg Trp Asp Xaa Leu Thr
        115                 120                 125

Leu Ser Gln Arg Xaa Gly Leu Asn Tyr Xaa Tyr Xaa Leu Gly Cys Asn
    130                 135                 140

Cys Lys Ile Lys Ser Cys Tyr Tyr Leu Pro Cys Phe Val Xaa Ser Xaa
145                 150                 155                 160

Asn Glu Cys Leu Trp Xaa Asp Xaa Leu Ser Asn Phe Xaa Tyr Pro Gly
                165                 170                 175

Tyr Gln Ser Lys Xaa Tyr Xaa Cys Ile Xaa Gln Xaa Gly Gly Tyr Cys
            180                 185                 190

Ser Trp Tyr Arg Gly Trp Ala Pro Xaa Asp Xaa Ser Ile Ile Asn Xaa
        195                 200                 205

Thr Asp Pro
    210
```

<210> SEQ ID NO 4
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)

```
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
```

<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide
<220> FEATURE:
<221> NAME/KEY: MOD_RES
<222> LOCATION: (25)..(25)
<223> OTHER INFORMATION: Thr, His, Lys, Pro, Arg, Ser or Trp
<220> FEATURE:
<221> NAME/KEY: MOD_RES
<222> LOCATION: (27)..(27)
<223> OTHER INFORMATION: Ser or Ala
<220> FEATURE:
<221> NAME/KEY: MOD_RES
<222> LOCATION: (28)..(28)
<223> OTHER INFORMATION: Pro, Asp, Leu or Ser
<220> FEATURE:
<221> NAME/KEY: MOD_RES
<222> LOCATION: (32)..(32)
<223> OTHER INFORMATION: Gln or Asn
<220> FEATURE:
<221> NAME/KEY: MOD_RES
<222> LOCATION: (39)..(39)
<223> OTHER INFORMATION: Asp or Thr
<220> FEATURE:
<221> NAME/KEY: MOD_RES
<222> LOCATION: (43)..(43)
<223> OTHER INFORMATION: Arg, Thr, Phe, Ala or Asn
<220> FEATURE:
<221> NAME/KEY: MOD_RES
<222> LOCATION: (45)..(45)
<223> OTHER INFORMATION: Lys, Ile or Thr
<220> FEATURE:
<221> NAME/KEY: MOD_RES
<222> LOCATION: (46)..(46)
<223> OTHER INFORMATION: Val or Asp
<220> FEATURE:
<221> NAME/KEY: MOD_RES
<222> LOCATION: (48)..(48)
<223> OTHER INFORMATION: Gly or Ser
<220> FEATURE:
<221> NAME/KEY: MOD_RES
<222> LOCATION: (49)..(49)
<223> OTHER INFORMATION: Lys or Ser
<220> FEATURE:
<221> NAME/KEY: MOD_RES
<222> LOCATION: (51)..(51)
<223> OTHER INFORMATION: Leu or Thr
<220> FEATURE:
<221> NAME/KEY: MOD_RES
<222> LOCATION: (53)..(53)
<223> OTHER INFORMATION: Lys or Thr
<220> FEATURE:
<221> NAME/KEY: MOD_RES
<222> LOCATION: (54)..(54)
<223> OTHER INFORMATION: Glu or Tyr
<220> FEATURE:
<221> NAME/KEY: MOD_RES
<222> LOCATION: (67)..(67)
<223> OTHER INFORMATION: Met or Asn
<220> FEATURE:
<221> NAME/KEY: MOD_RES
<222> LOCATION: (68)..(68)
<223> OTHER INFORMATION: Lys or Ile
<220> FEATURE:
<221> NAME/KEY: MOD_RES
<222> LOCATION: (78)..(78)
<223> OTHER INFORMATION: His, Asp or Trp
<220> FEATURE:
<221> NAME/KEY: MOD_RES
<222> LOCATION: (202)..(202)
<223> OTHER INFORMATION: Asp or Asn
<220> FEATURE:
<221> NAME/KEY: MOD_RES
<222> LOCATION: (207)..(207)
<223> OTHER INFORMATION: Asn or Ser

<400> SEQUENCE: 4

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Xaa Cys Xaa Xaa Ser His Pro Xaa
            20                  25                  30

Asp Ala Phe Cys Asn Ser Xaa Ile Val Ile Xaa Ala Xaa Xaa Val Xaa
        35                  40                  45

Xaa Lys Xaa Val Xaa Xaa Gly Pro Phe Gly Thr Leu Val Tyr Thr Ile
    50                  55                  60

Lys Gln Xaa Xaa Met Tyr Arg Gly Phe Thr Lys Met Pro Xaa Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Xaa Lys Ser Ile Ile Xaa Ala
        195                 200                 205

Thr Asp Pro
    210
```

<210> SEQ ID NO 5
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous
signal peptide
<220> FEATURE:
<221> NAME/KEY: MOD_RES
<222> LOCATION: (6)..(6)
<223> OTHER INFORMATION: Gly or any amino acid from a heterologous
signal peptide
<220> FEATURE:
<221> NAME/KEY: MOD_RES
<222> LOCATION: (7)..(7)
<223> OTHER INFORMATION: Leu or any amino acid from a heterologous
signal peptide
<220> FEATURE:
<221> NAME/KEY: MOD_RES
<222> LOCATION: (8)..(8)
<223> OTHER INFORMATION: Ile or any amino acid from a heterologous
signal peptide
<220> FEATURE:
<221> NAME/KEY: MOD_RES
<222> LOCATION: (9)..(9)
<223> OTHER INFORMATION: Val or any amino acid from a heterologous
signal peptide
<220> FEATURE:
<221> NAME/KEY: MOD_RES
<222> LOCATION: (10)..(11)
<223> OTHER INFORMATION: Leu or any amino acid from a heterologous
signal peptide
<220> FEATURE:
<221> NAME/KEY: MOD_RES
<222> LOCATION: (12)..(12)
<223> OTHER INFORMATION: Gly or any amino acid from a heterologous
signal peptide
<220> FEATURE:
<221> NAME/KEY: MOD_RES
<222> LOCATION: (13)..(13)
<223> OTHER INFORMATION: Ser or any amino acid from a heterologous
signal peptide
<220> FEATURE:
<221> NAME/KEY: MOD_RES
<222> LOCATION: (14)..(14)
<223> OTHER INFORMATION: Trp or any amino acid from a heterologous
signal peptide
<220> FEATURE:
<221> NAME/KEY: MOD_RES
<222> LOCATION: (15)..(15)
<223> OTHER INFORMATION: Ser or any amino acid from a heterologous
signal peptide
<220> FEATURE:
<221> NAME/KEY: MOD_RES
<222> LOCATION: (16)..(16)
<223> OTHER INFORMATION: Leu or any amino acid from a heterologous
signal peptide
<220> FEATURE:
<221> NAME/KEY: MOD_RES
<222> LOCATION: (17)..(17)
<223> OTHER INFORMATION: Gly or any amino acid from a heterologous
signal peptide
<220> FEATURE:
<221> NAME/KEY: MOD_RES
<222> LOCATION: (18)..(18)
<223> OTHER INFORMATION: Asp or any amino acid from a heterologous
signal peptide
<220> FEATURE:
<221> NAME/KEY: MOD_RES
<222> LOCATION: (19)..(19)
<223> OTHER INFORMATION: Trp or any amino acid from a heterologous
signal peptide
<220> FEATURE:
<221> NAME/KEY: MOD_RES
<222> LOCATION: (20)..(20)
<223> OTHER INFORMATION: Gly or any amino acid from a heterologous
signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 5

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Glu Val Val Gly
        35                  40                  45

Ser Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 6
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 6

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Glu Val Val Gly
        35                  40                  45

Glu Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 7
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide

```
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
```

signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 7

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Glu Val Val Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 8
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide

```
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
```

signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 8

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Glu Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Glu
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 9
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous
signal peptide
<220> FEATURE:
<221> NAME/KEY: MOD_RES
<222> LOCATION: (19)..(19)
<223> OTHER INFORMATION: Trp or any amino acid from a heterologous
signal peptide
<220> FEATURE:
<221> NAME/KEY: MOD_RES
<222> LOCATION: (20)..(20)
<223> OTHER INFORMATION: Gly or any amino acid from a heterologous
signal peptide
<220> FEATURE:
<221> NAME/KEY: MOD_RES
<222> LOCATION: (21)..(21)
<223> OTHER INFORMATION: Ala or any amino acid from a heterologous
signal peptide
<220> FEATURE:
<221> NAME/KEY: MOD_RES
<222> LOCATION: (22)..(22)
<223> OTHER INFORMATION: Glu or any amino acid from a heterologous
signal peptide
<220> FEATURE:
<221> NAME/KEY: MOD_RES
<222> LOCATION: (23)..(23)
<223> OTHER INFORMATION: Ala or any amino acid from a heterologous
signal peptide

<400> SEQUENCE: 9

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Thr Lys Met Pro Glu Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 10
<211> LENGTH: 211

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous

```
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 10

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Glu Val Val Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Thr Lys Met Pro Glu Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
```

210

<210> SEQ ID NO 11
<211> LENGTH: 211
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Met or any amino acid from a heterologous
signal peptide
<220> FEATURE:
<221> NAME/KEY: MOD_RES
<222> LOCATION: (2)..(2)
<223> OTHER INFORMATION: Thr or any amino acid from a heterologous
signal peptide
<220> FEATURE:
<221> NAME/KEY: MOD_RES
<222> LOCATION: (3)..(3)
<223> OTHER INFORMATION: Pro or any amino acid from a heterologous
signal peptide
<220> FEATURE:
<221> NAME/KEY: MOD_RES
<222> LOCATION: (4)..(4)
<223> OTHER INFORMATION: Trp or any amino acid from a heterologous
signal peptide
<220> FEATURE:
<221> NAME/KEY: MOD_RES
<222> LOCATION: (5)..(5)
<223> OTHER INFORMATION: Leu or any amino acid from a heterologous
signal peptide
<220> FEATURE:
<221> NAME/KEY: MOD_RES
<222> LOCATION: (6)..(6)
<223> OTHER INFORMATION: Gly or any amino acid from a heterologous
signal peptide
<220> FEATURE:
<221> NAME/KEY: MOD_RES
<222> LOCATION: (7)..(7)
<223> OTHER INFORMATION: Leu or any amino acid from a heterologous
signal peptide
<220> FEATURE:
<221> NAME/KEY: MOD_RES
<222> LOCATION: (8)..(8)
<223> OTHER INFORMATION: Ile or any amino acid from a heterologous
signal peptide
<220> FEATURE:
<221> NAME/KEY: MOD_RES
<222> LOCATION: (9)..(9)
<223> OTHER INFORMATION: Val or any amino acid from a heterologous
signal peptide
<220> FEATURE:
<221> NAME/KEY: MOD_RES
<222> LOCATION: (10)..(11)
<223> OTHER INFORMATION: Leu or any amino acid from a heterologous
signal peptide
<220> FEATURE:
<221> NAME/KEY: MOD_RES
<222> LOCATION: (12)..(12)
<223> OTHER INFORMATION: Gly or any amino acid from a heterologous
signal peptide
<220> FEATURE:
<221> NAME/KEY: MOD_RES
<222> LOCATION: (13)..(13)
<223> OTHER INFORMATION: Ser or any amino acid from a heterologous
signal peptide
<220> FEATURE:
<221> NAME/KEY: MOD_RES
<222> LOCATION: (14)..(14)
<223> OTHER INFORMATION: Trp or any amino acid from a heterologous
signal peptide
<220> FEATURE:
<221> NAME/KEY: MOD_RES
<222> LOCATION: (15)..(15)
<223> OTHER INFORMATION: Ser or any amino acid from a heterologous

```
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Thr Lys Met Pro Glu Val Glu
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190
```

```
Ser Trp Tyr Arg Gly Trp Ala Pro Pro Asp Lys Ser Ile Ile Asn Ala
        195                 200                 205

Thr Asp Pro
    210


<210> SEQ ID NO 12
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
```

```
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Glu Val Val Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Thr Lys Met Pro Glu Val Glu
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160
```

-continued

```
Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 13
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 13

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Glu Lys Met Pro Glu Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
```

```
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 14
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous

```
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Glu Lys Met Pro Asp Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110
```

-continued

```
Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 15
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous

```
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 15

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Thr Val Lys Glu Gly Pro Phe Gly Thr Leu Val Tyr Thr Ile
    50                  55                  60

Lys Gln Met Lys Met Tyr Arg Gly Phe Glu Lys Met Pro Asp Val Gln
65                  70                  75                  80
```

```
Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

```
<210> SEQ ID NO 16
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
```

-continued

```
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
```

```
    50                  55                  60

Lys Gln Met Lys Met Tyr Arg Gly Phe Glu Lys Met Pro Glu Val Glu
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 17
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
```

signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 17

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30
```

```
Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Glu Lys Met Pro Asp Val Glu
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 18
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous

```
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 18
```

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Asn Val Thr Gly
        35                  40                  45

Lys Lys Leu Val Lys Glu Gly Pro Phe Gly Thr Leu Val Tyr Glu Ile
    50                  55                  60

Lys Gln Met Lys Met Tyr Arg Gly Phe Glu Lys Met Pro Glu Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 19
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
```

```
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
```

<223> OTHER INFORMATION: Ala or any amino acid from a heterologous
      signal peptide

<400> SEQUENCE: 19

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Asn Lys Thr Val Lys Glu Gly Pro Phe Gly Thr Leu Val Tyr Glu Ile
    50                  55                  60

Lys Gln Met Lys Met Tyr Arg Gly Phe Glu Lys Met Pro Glu Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 20
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous
signal peptide
<220> FEATURE:
<221> NAME/KEY: MOD_RES
<222> LOCATION: (7)..(7)
<223> OTHER INFORMATION: Leu or any amino acid from a heterologous
signal peptide
<220> FEATURE:
<221> NAME/KEY: MOD_RES
<222> LOCATION: (8)..(8)
<223> OTHER INFORMATION: Ile or any amino acid from a heterologous
signal peptide
<220> FEATURE:
<221> NAME/KEY: MOD_RES
<222> LOCATION: (9)..(9)
<223> OTHER INFORMATION: Val or any amino acid from a heterologous
signal peptide
<220> FEATURE:
<221> NAME/KEY: MOD_RES
<222> LOCATION: (10)..(11)
<223> OTHER INFORMATION: Leu or any amino acid from a heterologous
signal peptide
<220> FEATURE:
<221> NAME/KEY: MOD_RES
<222> LOCATION: (12)..(12)
<223> OTHER INFORMATION: Gly or any amino acid from a heterologous
signal peptide
<220> FEATURE:
<221> NAME/KEY: MOD_RES
<222> LOCATION: (13)..(13)
<223> OTHER INFORMATION: Ser or any amino acid from a heterologous
signal peptide
<220> FEATURE:
<221> NAME/KEY: MOD_RES
<222> LOCATION: (14)..(14)
<223> OTHER INFORMATION: Trp or any amino acid from a heterologous
signal peptide
<220> FEATURE:
<221> NAME/KEY: MOD_RES
<222> LOCATION: (15)..(15)
<223> OTHER INFORMATION: Ser or any amino acid from a heterologous
signal peptide
<220> FEATURE:
<221> NAME/KEY: MOD_RES
<222> LOCATION: (16)..(16)
<223> OTHER INFORMATION: Leu or any amino acid from a heterologous
signal peptide
<220> FEATURE:
<221> NAME/KEY: MOD_RES
<222> LOCATION: (17)..(17)
<223> OTHER INFORMATION: Gly or any amino acid from a heterologous
signal peptide
<220> FEATURE:
<221> NAME/KEY: MOD_RES
<222> LOCATION: (18)..(18)
<223> OTHER INFORMATION: Asp or any amino acid from a heterologous
signal peptide
<220> FEATURE:
<221> NAME/KEY: MOD_RES
<222> LOCATION: (19)..(19)
<223> OTHER INFORMATION: Trp or any amino acid from a heterologous
signal peptide
<220> FEATURE:
<221> NAME/KEY: MOD_RES
<222> LOCATION: (20)..(20)
<223> OTHER INFORMATION: Gly or any amino acid from a heterologous
signal peptide
<220> FEATURE:
<221> NAME/KEY: MOD_RES
<222> LOCATION: (21)..(21)
<223> OTHER INFORMATION: Ala or any amino acid from a heterologous
signal peptide
<220> FEATURE:
<221> NAME/KEY: MOD_RES
<222> LOCATION: (22)..(22)

<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 20

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Glu Val Val Gly
        35                  40                  45

Asn Lys Thr Val Lys Glu Gly Pro Phe Gly Thr Leu Val Tyr Glu Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 21
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous

```
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
```

<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 21

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Asn Lys Thr Val Lys Glu Gly Pro Phe Gly Thr Leu Val Tyr Thr Ile
    50                  55                  60

Lys Gln Met Lys Met Tyr Arg Gly Phe Glu Lys Met Pro Glu Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 22
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous

```
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
```

<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 22

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Ser Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 23
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous

```
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
```

```
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Ser Val Val Gly
        35                  40                  45

Lys Lys Leu Val Lys Glu Gly Pro Asn Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 24
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
```

signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)

<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 24

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Ser Val Val Gly
        35                  40                  45

Lys Lys Leu Val Lys Glu Gly Pro Asn Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Ser Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 25
<211> LENGTH: 211
<212> TYPE: PRT
<213> ORGANISM: Artificial Sequence
<220> FEATURE:
<223> OTHER INFORMATION: Description of Artificial Sequence: Synthetic

```
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
```

<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 25

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Glu Lys Met Pro Asp Val Glu
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 26

-continued

<211> LENGTH: 211
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Met or any amino acid from a heterologous
signal peptide
<220> FEATURE:
<221> NAME/KEY: MOD_RES
<222> LOCATION: (2)..(2)
<223> OTHER INFORMATION: Thr or any amino acid from a heterologous
signal peptide
<220> FEATURE:
<221> NAME/KEY: MOD_RES
<222> LOCATION: (3)..(3)
<223> OTHER INFORMATION: Pro or any amino acid from a heterologous
signal peptide
<220> FEATURE:
<221> NAME/KEY: MOD_RES
<222> LOCATION: (4)..(4)
<223> OTHER INFORMATION: Trp or any amino acid from a heterologous
signal peptide
<220> FEATURE:
<221> NAME/KEY: MOD_RES
<222> LOCATION: (5)..(5)
<223> OTHER INFORMATION: Leu or any amino acid from a heterologous
signal peptide
<220> FEATURE:
<221> NAME/KEY: MOD_RES
<222> LOCATION: (6)..(6)
<223> OTHER INFORMATION: Gly or any amino acid from a heterologous
signal peptide
<220> FEATURE:
<221> NAME/KEY: MOD_RES
<222> LOCATION: (7)..(7)
<223> OTHER INFORMATION: Leu or any amino acid from a heterologous
signal peptide
<220> FEATURE:
<221> NAME/KEY: MOD_RES
<222> LOCATION: (8)..(8)
<223> OTHER INFORMATION: Ile or any amino acid from a heterologous
signal peptide
<220> FEATURE:
<221> NAME/KEY: MOD_RES
<222> LOCATION: (9)..(9)
<223> OTHER INFORMATION: Val or any amino acid from a heterologous
signal peptide
<220> FEATURE:
<221> NAME/KEY: MOD_RES
<222> LOCATION: (10)..(11)
<223> OTHER INFORMATION: Leu or any amino acid from a heterologous
signal peptide
<220> FEATURE:
<221> NAME/KEY: MOD_RES
<222> LOCATION: (12)..(12)
<223> OTHER INFORMATION: Gly or any amino acid from a heterologous
signal peptide
<220> FEATURE:
<221> NAME/KEY: MOD_RES
<222> LOCATION: (13)..(13)
<223> OTHER INFORMATION: Ser or any amino acid from a heterologous
signal peptide
<220> FEATURE:
<221> NAME/KEY: MOD_RES
<222> LOCATION: (14)..(14)
<223> OTHER INFORMATION: Trp or any amino acid from a heterologous
signal peptide
<220> FEATURE:
<221> NAME/KEY: MOD_RES
<222> LOCATION: (15)..(15)
<223> OTHER INFORMATION: Ser or any amino acid from a heterologous
signal peptide
<220> FEATURE:
<221> NAME/KEY: MOD_RES
<222> LOCATION: (16)..(16)

<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 26

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Asn Val Thr Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205
```

```
Thr Asp Pro
    210


<210> SEQ ID NO 27
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
```

<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 27

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Asn Lys Thr Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
```

```
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 28
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
```

<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 28

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Ser Lys Leu Val Lys Glu Gly Pro Asn Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160
```

```
Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 29
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)

<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 29

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Ser Lys Leu Val Lys Glu Gly Pro Asn Gly Thr Leu Val Tyr Thr Ile
    50                  55                  60

Lys Gln Met Ser Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125
```

```
Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

```
<210> SEQ ID NO 30
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
```

<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 30

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Asn Leu Thr Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
```

```
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 31
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
```

<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 31

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Asn Phe Thr Thr Leu Val Tyr Thr Ile
    50                  55                  60

Lys Gln Met Lys Met Tyr Arg Gly Phe Thr Lys Met Pro His Val Gln
65                  70                  75                  80
```

```
Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

```
<210> SEQ ID NO 32
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
```

```
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 32

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45
```

```
Lys Lys Leu Val Lys Glu Gly Asn Phe Thr Thr Leu Val Tyr Asn Ile
    50                  55                  60

Thr Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

```
<210> SEQ ID NO 33
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
```

<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 33

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
```

```
            20                  25                  30

Asp Ala Phe Cys Asn Ser Asp Ile Val Ile Arg Ala Lys Val Val Gly
        35                  40                  45

Lys Lys Leu Val Lys Glu Gly Pro Asn Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 34
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
```

<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 34

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Asn Gly Thr Leu Val Tyr Thr Ile
    50                  55                  60

Lys Gln Met Ser Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 35
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
```

<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 35

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Cys Thr Cys Ser Pro Ser His Pro Gln
20 25 30

Asp Ala Phe Cys Asn Ser Asp Ile Val Ile Arg Ala Lys Val Val Gly
35 40 45

Lys Lys Leu Val Lys Glu Gly Pro Asn Gly Thr Leu Val Tyr Thr Ile
50 55 60

Lys Gln Met Lys Met Tyr Arg Gly Phe Thr Lys Met Pro His Val Gln
65 70 75 80

Tyr Ile His Thr Glu Ala Ser Glu Ser Leu Cys Gly Leu Lys Leu Glu
85 90 95

Val Asn Lys Tyr Gln Tyr Leu Leu Thr Gly Arg Val Tyr Asp Gly Lys
100 105 110

Met Tyr Thr Gly Leu Cys Asn Phe Val Glu Arg Trp Asp Gln Leu Thr
115 120 125

Leu Ser Gln Arg Ser Gly Leu Asn Tyr Arg Tyr His Leu Gly Cys Asn
130 135 140

Cys Lys Ile Lys Ser Cys Tyr Tyr Leu Pro Cys Phe Val Thr Ser Lys
145 150 155 160

Asn Glu Cys Leu Trp Thr Asp Met Leu Ser Asn Phe Gly Tyr Pro Gly
165 170 175

Tyr Gln Ser Lys His Tyr Ala Cys Ile Arg Gln Lys Gly Gly Tyr Cys
180 185 190

Ser Trp Tyr Arg Gly Trp Ala Pro Pro Asp Lys Ser Ile Ile Asn Ala
195 200 205

Thr Asp Pro
210

<210> SEQ ID NO 36
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)

<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES -continued
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 36

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Asn Ile
    50                  55                  60

Thr Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 37
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)

<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 37

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Asn Gln Thr Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 38
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)

<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
signal peptide
<220> FEATURE:
<221> NAME/KEY: MOD_RES
<222> LOCATION: (21)..(21)
<223> OTHER INFORMATION: Ala or any amino acid from a heterologous
signal peptide
<220> FEATURE:
<221> NAME/KEY: MOD_RES
<222> LOCATION: (22)..(22)
<223> OTHER INFORMATION: Glu or any amino acid from a heterologous
signal peptide
<220> FEATURE:
<221> NAME/KEY: MOD_RES
<222> LOCATION: (23)..(23)
<223> OTHER INFORMATION: Ala or any amino acid from a heterologous
signal peptide

<400> SEQUENCE: 38

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Asn Met Thr His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 39
<211> LENGTH: 211
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Met or any amino acid from a heterologous
signal peptide
<220> FEATURE:
<221> NAME/KEY: MOD_RES
<222> LOCATION: (2)..(2)

<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous
signal peptide
<220> FEATURE:
<221> NAME/KEY: MOD_RES
<222> LOCATION: (20)..(20)
<223> OTHER INFORMATION: Gly or any amino acid from a heterologous
signal peptide
<220> FEATURE:
<221> NAME/KEY: MOD_RES
<222> LOCATION: (21)..(21)
<223> OTHER INFORMATION: Ala or any amino acid from a heterologous
signal peptide
<220> FEATURE:
<221> NAME/KEY: MOD_RES
<222> LOCATION: (22)..(22)
<223> OTHER INFORMATION: Glu or any amino acid from a heterologous
signal peptide
<220> FEATURE:
<221> NAME/KEY: MOD_RES
<222> LOCATION: (23)..(23)
<223> OTHER INFORMATION: Ala or any amino acid from a heterologous
signal peptide

<400> SEQUENCE: 39

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro Asn Val Thr
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 40
<211> LENGTH: 211
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)

<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES

```
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 40

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Asn Leu Thr
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 41
<211> LENGTH: 211
<212> TYPE: PRT
<213> ORGANISM: Artificial Sequence
<220> FEATURE:
```

<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Met or any amino acid from a heterologous
signal peptide
<220> FEATURE:
<221> NAME/KEY: MOD_RES
<222> LOCATION: (2)..(2)
<223> OTHER INFORMATION: Thr or any amino acid from a heterologous
signal peptide
<220> FEATURE:
<221> NAME/KEY: MOD_RES
<222> LOCATION: (3)..(3)
<223> OTHER INFORMATION: Pro or any amino acid from a heterologous
signal peptide
<220> FEATURE:
<221> NAME/KEY: MOD_RES
<222> LOCATION: (4)..(4)
<223> OTHER INFORMATION: Trp or any amino acid from a heterologous
signal peptide
<220> FEATURE:
<221> NAME/KEY: MOD_RES
<222> LOCATION: (5)..(5)
<223> OTHER INFORMATION: Leu or any amino acid from a heterologous
signal peptide
<220> FEATURE:
<221> NAME/KEY: MOD_RES
<222> LOCATION: (6)..(6)
<223> OTHER INFORMATION: Gly or any amino acid from a heterologous
signal peptide
<220> FEATURE:
<221> NAME/KEY: MOD_RES
<222> LOCATION: (7)..(7)
<223> OTHER INFORMATION: Leu or any amino acid from a heterologous
signal peptide
<220> FEATURE:
<221> NAME/KEY: MOD_RES
<222> LOCATION: (8)..(8)
<223> OTHER INFORMATION: Ile or any amino acid from a heterologous
signal peptide
<220> FEATURE:
<221> NAME/KEY: MOD_RES
<222> LOCATION: (9)..(9)
<223> OTHER INFORMATION: Val or any amino acid from a heterologous
signal peptide
<220> FEATURE:
<221> NAME/KEY: MOD_RES
<222> LOCATION: (10)..(11)
<223> OTHER INFORMATION: Leu or any amino acid from a heterologous
signal peptide
<220> FEATURE:
<221> NAME/KEY: MOD_RES
<222> LOCATION: (12)..(12)
<223> OTHER INFORMATION: Gly or any amino acid from a heterologous
signal peptide
<220> FEATURE:
<221> NAME/KEY: MOD_RES
<222> LOCATION: (13)..(13)
<223> OTHER INFORMATION: Ser or any amino acid from a heterologous
signal peptide
<220> FEATURE:
<221> NAME/KEY: MOD_RES
<222> LOCATION: (14)..(14)
<223> OTHER INFORMATION: Trp or any amino acid from a heterologous
signal peptide
<220> FEATURE:
<221> NAME/KEY: MOD_RES
<222> LOCATION: (15)..(15)
<223> OTHER INFORMATION: Ser or any amino acid from a heterologous
signal peptide
<220> FEATURE:
<221> NAME/KEY: MOD_RES
<222> LOCATION: (16)..(16)
<223> OTHER INFORMATION: Leu or any amino acid from a heterologous
signal peptide
<220> FEATURE:
<221> NAME/KEY: MOD_RES

```
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 41

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Asn
                85                  90                  95

Val Thr Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 42
<211> LENGTH: 211
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Met or any amino acid from a heterologous
signal peptide
<220> FEATURE:
<221> NAME/KEY: MOD_RES
<222> LOCATION: (2)..(2)
<223> OTHER INFORMATION: Thr or any amino acid from a heterologous
signal peptide
<220> FEATURE:
<221> NAME/KEY: MOD_RES
<222> LOCATION: (3)..(3)
<223> OTHER INFORMATION: Pro or any amino acid from a heterologous
signal peptide
<220> FEATURE:
<221> NAME/KEY: MOD_RES
<222> LOCATION: (4)..(4)
<223> OTHER INFORMATION: Trp or any amino acid from a heterologous
signal peptide
<220> FEATURE:
<221> NAME/KEY: MOD_RES
<222> LOCATION: (5)..(5)
<223> OTHER INFORMATION: Leu or any amino acid from a heterologous
signal peptide
<220> FEATURE:
<221> NAME/KEY: MOD_RES
<222> LOCATION: (6)..(6)
<223> OTHER INFORMATION: Gly or any amino acid from a heterologous
signal peptide
<220> FEATURE:
<221> NAME/KEY: MOD_RES
<222> LOCATION: (7)..(7)
<223> OTHER INFORMATION: Leu or any amino acid from a heterologous
signal peptide
<220> FEATURE:
<221> NAME/KEY: MOD_RES
<222> LOCATION: (8)..(8)
<223> OTHER INFORMATION: Ile or any amino acid from a heterologous
signal peptide
<220> FEATURE:
<221> NAME/KEY: MOD_RES
<222> LOCATION: (9)..(9)
<223> OTHER INFORMATION: Val or any amino acid from a heterologous
signal peptide
<220> FEATURE:
<221> NAME/KEY: MOD_RES
<222> LOCATION: (10)..(11)
<223> OTHER INFORMATION: Leu or any amino acid from a heterologous
signal peptide
<220> FEATURE:
<221> NAME/KEY: MOD_RES
<222> LOCATION: (12)..(12)
<223> OTHER INFORMATION: Gly or any amino acid from a heterologous
signal peptide
<220> FEATURE:
<221> NAME/KEY: MOD_RES
<222> LOCATION: (13)..(13)
<223> OTHER INFORMATION: Ser or any amino acid from a heterologous
signal peptide
<220> FEATURE:
<221> NAME/KEY: MOD_RES
<222> LOCATION: (14)..(14)
<223> OTHER INFORMATION: Trp or any amino acid from a heterologous
signal peptide
<220> FEATURE:
<221> NAME/KEY: MOD_RES
<222> LOCATION: (15)..(15)
<223> OTHER INFORMATION: Ser or any amino acid from a heterologous
signal peptide
<220> FEATURE:
<221> NAME/KEY: MOD_RES

```
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 42

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Asn Asn Thr Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205
```

```
Thr Asp Pro
    210


<210> SEQ ID NO 43
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
```

```
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 43

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asn Gly Thr
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175
```

-continued

```
Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 44
<211> LENGTH: 211
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Met or any amino acid from a heterologous
signal peptide
<220> FEATURE:
<221> NAME/KEY: MOD_RES
<222> LOCATION: (2)..(2)
<223> OTHER INFORMATION: Thr or any amino acid from a heterologous
signal peptide
<220> FEATURE:
<221> NAME/KEY: MOD_RES
<222> LOCATION: (3)..(3)
<223> OTHER INFORMATION: Pro or any amino acid from a heterologous
signal peptide
<220> FEATURE:
<221> NAME/KEY: MOD_RES
<222> LOCATION: (4)..(4)
<223> OTHER INFORMATION: Trp or any amino acid from a heterologous
signal peptide
<220> FEATURE:
<221> NAME/KEY: MOD_RES
<222> LOCATION: (5)..(5)
<223> OTHER INFORMATION: Leu or any amino acid from a heterologous
signal peptide
<220> FEATURE:
<221> NAME/KEY: MOD_RES
<222> LOCATION: (6)..(6)
<223> OTHER INFORMATION: Gly or any amino acid from a heterologous
signal peptide
<220> FEATURE:
<221> NAME/KEY: MOD_RES
<222> LOCATION: (7)..(7)
<223> OTHER INFORMATION: Leu or any amino acid from a heterologous
signal peptide
<220> FEATURE:
<221> NAME/KEY: MOD_RES
<222> LOCATION: (8)..(8)
<223> OTHER INFORMATION: Ile or any amino acid from a heterologous
signal peptide
<220> FEATURE:
<221> NAME/KEY: MOD_RES
<222> LOCATION: (9)..(9)
<223> OTHER INFORMATION: Val or any amino acid from a heterologous
signal peptide
<220> FEATURE:
<221> NAME/KEY: MOD_RES
<222> LOCATION: (10)..(11)
<223> OTHER INFORMATION: Leu or any amino acid from a heterologous
signal peptide
<220> FEATURE:
<221> NAME/KEY: MOD_RES
<222> LOCATION: (12)..(12)
<223> OTHER INFORMATION: Gly or any amino acid from a heterologous
signal peptide
<220> FEATURE:
<221> NAME/KEY: MOD_RES
<222> LOCATION: (13)..(13)
<223> OTHER INFORMATION: Ser or any amino acid from a heterologous
signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 44

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Asn Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
```

```
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 45
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 45

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125
```

```
Leu Ser Gln Arg Lys Gly Leu Asn Tyr Thr Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 46
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous signal peptide
<220> FEATURE:
<221> NAME/KEY: MOD_RES
<222> LOCATION: (7)..(7)
<223> OTHER INFORMATION: Leu or any amino acid from a heterologous signal peptide
<220> FEATURE:
<221> NAME/KEY: MOD_RES
<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES

```
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 46

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95
```

```
Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Asn Tyr Thr Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 47
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
```

```
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 47

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
```

```
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Asn Ser Thr
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

```
<210> SEQ ID NO 48
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
```

<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 48

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45
```

```
Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Asn Asp Thr Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

```
<210> SEQ ID NO 49
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
```

<222> LOCATION: (8)..(8)
<223> OTHER INFORMATION: Ile or any amino acid from a heterologous signal peptide
<220> FEATURE:
<221> NAME/KEY: MOD_RES
<222> LOCATION: (9)..(9)
<223> OTHER INFORMATION: Val or any amino acid from a heterologous signal peptide
<220> FEATURE:
<221> NAME/KEY: MOD_RES
<222> LOCATION: (10)..(11)
<223> OTHER INFORMATION: Leu or any amino acid from a heterologous signal peptide
<220> FEATURE:
<221> NAME/KEY: MOD_RES
<222> LOCATION: (12)..(12)
<223> OTHER INFORMATION: Gly or any amino acid from a heterologous signal peptide
<220> FEATURE:
<221> NAME/KEY: MOD_RES
<222> LOCATION: (13)..(13)
<223> OTHER INFORMATION: Ser or any amino acid from a heterologous signal peptide
<220> FEATURE:
<221> NAME/KEY: MOD_RES
<222> LOCATION: (14)..(14)
<223> OTHER INFORMATION: Trp or any amino acid from a heterologous signal peptide
<220> FEATURE:
<221> NAME/KEY: MOD_RES
<222> LOCATION: (15)..(15)
<223> OTHER INFORMATION: Ser or any amino acid from a heterologous signal peptide
<220> FEATURE:
<221> NAME/KEY: MOD_RES
<222> LOCATION: (16)..(16)
<223> OTHER INFORMATION: Leu or any amino acid from a heterologous signal peptide
<220> FEATURE:
<221> NAME/KEY: MOD_RES
<222> LOCATION: (17)..(17)
<223> OTHER INFORMATION: Gly or any amino acid from a heterologous signal peptide
<220> FEATURE:
<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 49

```
Xaa Xaa Xaa Xaa Xaa Xaa Xaa Xaa Xaa Xaa Xaa Xaa Xaa Xaa Xaa Xaa
1               5                   10                  15
```

```
Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Thr Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210


<210> SEQ ID NO 50
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
```

<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 50

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Cys Thr Cys Ser Pro Ser His Pro Gln
20 25 30

Asp Ala Phe Cys Asn Ser Asp Ile Val Ile Arg Ala Lys Val Val Gly
35 40 45

Lys Lys Leu Val Lys Glu Gly Pro Phe Gly Thr Leu Val Tyr Thr Ile
50 55 60

Lys Gln Met Lys Met Tyr Arg Gly Phe Thr Lys Met Pro His Val Gln
65 70 75 80

Tyr Ile His Thr Glu Ala Ser Glu Ser Leu Cys Gly Leu Lys Leu Glu
85 90 95

Val Asn Lys Tyr Gln Tyr Leu Leu Thr Gly Arg Val Tyr Asp Gly Lys
100 105 110

Met Tyr Thr Gly Leu Cys Asn Phe Val Glu Arg Trp Asp Gln Leu Thr
115 120 125

Leu Ser Gln Arg Lys Gly Leu Asn Tyr Arg Tyr His Leu Gly Cys Asn
130 135 140

Cys Lys Ile Lys Ser Cys Tyr Tyr Leu Pro Cys Phe Val Thr Ser Lys
145 150 155 160

Asn Glu Cys Leu Trp Thr Asp Met Leu Ser Asn Phe Gly Tyr Pro Gly
165 170 175

Tyr Gln Ser Lys Asn Tyr Thr Cys Ile Arg Gln Lys Gly Gly Tyr Cys
180 185 190

Ser Trp Tyr Arg Gly Trp Ala Pro Pro Asp Lys Ser Ile Ile Asn Ala
195 200 205

Thr Asp Pro
210

<210> SEQ ID NO 51
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:
<221> NAME/KEY: MOD_RES
<222> LOCATION: (22)..(22)
<223> OTHER INFORMATION: Glu or any amino acid from a heterologous
      signal peptide
<220> FEATURE:

<221> NAME/KEY: MOD_RES
<222> LOCATION: (23)..(23)
<223> OTHER INFORMATION: Ala or any amino acid from a heterologous signal peptide

<400> SEQUENCE: 51

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Asn Gln Thr Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 52
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES
<222> LOCATION: (3)..(3)
<223> OTHER INFORMATION: Pro or any amino acid from a heterologous signal peptide
<220> FEATURE:
<221> NAME/KEY: MOD_RES
<222> LOCATION: (4)..(4)
<223> OTHER INFORMATION: Trp or any amino acid from a heterologous signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:
<221> NAME/KEY: MOD_RES
<222> LOCATION: (21)..(21)
<223> OTHER INFORMATION: Ala or any amino acid from a heterologous
      signal peptide
<220> FEATURE:

<221> NAME/KEY: MOD_RES
<222> LOCATION: (22)..(22)
<223> OTHER INFORMATION: Glu or any amino acid from a heterologous
      signal peptide
<220> FEATURE:
<221> NAME/KEY: MOD_RES
<222> LOCATION: (23)..(23)
<223> OTHER INFORMATION: Ala or any amino acid from a heterologous
      signal peptide

<400> SEQUENCE: 52

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Asn Asp Thr Ser Ile Ile Asn Ala
        195                 200                 205

Thr Asp Pro
    210
```

<210> SEQ ID NO 53
<211> LENGTH: 211
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
<221> NAME/KEY: MOD_RES
<222> LOCATION: (20)..(20)
<223> OTHER INFORMATION: Gly or any amino acid from a heterologous
      signal peptide
<220> FEATURE:

<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 53

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Thr Val Lys Glu Gly Pro Phe Gly Thr Leu Val Tyr Thr Ile
    50                  55                  60

Lys Gln Met Lys Met Tyr Arg Gly Phe Glu Lys Met Pro Asp Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 54
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous signal peptide
<220> FEATURE:
<221> NAME/KEY: MOD_RES

```
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:
<221> NAME/KEY: MOD_RES
<222> LOCATION: (19)..(19)
<223> OTHER INFORMATION: Trp or any amino acid from a heterologous
      signal peptide
<220> FEATURE:
```

<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 54

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Asn Val Thr Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Ala
        195                 200                 205

Thr Asp Pro
    210
```

<210> SEQ ID NO 55
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:
<221> NAME/KEY: MOD_RES
<222> LOCATION: (18)..(18)
<223> OTHER INFORMATION: Asp or any amino acid from a heterologous
      signal peptide
<220> FEATURE:

<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 55

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Tyr
        195                 200                 205

Thr Asp Pro
    210
```

<210> SEQ ID NO 56
<211> LENGTH: 211
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (1)..(1)
<223> OTHER INFORMATION: Met or any amino acid from a heterologous
      signal peptide
<220> FEATURE:
<221> NAME/KEY: MOD_RES
<222> LOCATION: (2)..(2)
<223> OTHER INFORMATION: Thr or any amino acid from a heterologous
      signal peptide
<220> FEATURE:
<221> NAME/KEY: MOD_RES
<222> LOCATION: (3)..(3)
<223> OTHER INFORMATION: Pro or any amino acid from a heterologous
      signal peptide
<220> FEATURE:
<221> NAME/KEY: MOD_RES
<222> LOCATION: (4)..(4)
<223> OTHER INFORMATION: Trp or any amino acid from a heterologous
      signal peptide
<220> FEATURE:
<221> NAME/KEY: MOD_RES
<222> LOCATION: (5)..(5)
<223> OTHER INFORMATION: Leu or any amino acid from a heterologous
      signal peptide
<220> FEATURE:
<221> NAME/KEY: MOD_RES
<222> LOCATION: (6)..(6)
<223> OTHER INFORMATION: Gly or any amino acid from a heterologous
      signal peptide
<220> FEATURE:
<221> NAME/KEY: MOD_RES
<222> LOCATION: (7)..(7)
<223> OTHER INFORMATION: Leu or any amino acid from a heterologous
      signal peptide
<220> FEATURE:
<221> NAME/KEY: MOD_RES
<222> LOCATION: (8)..(8)
<223> OTHER INFORMATION: Ile or any amino acid from a heterologous
      signal peptide
<220> FEATURE:
<221> NAME/KEY: MOD_RES
<222> LOCATION: (9)..(9)
<223> OTHER INFORMATION: Val or any amino acid from a heterologous
      signal peptide
<220> FEATURE:
<221> NAME/KEY: MOD_RES
<222> LOCATION: (10)..(11)
<223> OTHER INFORMATION: Leu or any amino acid from a heterologous
      signal peptide
<220> FEATURE:
<221> NAME/KEY: MOD_RES
<222> LOCATION: (12)..(12)
<223> OTHER INFORMATION: Gly or any amino acid from a heterologous
      signal peptide
<220> FEATURE:
<221> NAME/KEY: MOD_RES
<222> LOCATION: (13)..(13)
<223> OTHER INFORMATION: Ser or any amino acid from a heterologous
      signal peptide
<220> FEATURE:
<221> NAME/KEY: MOD_RES
<222> LOCATION: (14)..(14)
<223> OTHER INFORMATION: Trp or any amino acid from a heterologous
      signal peptide
<220> FEATURE:
<221> NAME/KEY: MOD_RES
<222> LOCATION: (15)..(15)
<223> OTHER INFORMATION: Ser or any amino acid from a heterologous
      signal peptide
<220> FEATURE:
<221> NAME/KEY: MOD_RES
<222> LOCATION: (16)..(16)
<223> OTHER INFORMATION: Leu or any amino acid from a heterologous
      signal peptide
<220> FEATURE:
<221> NAME/KEY: MOD_RES
<222> LOCATION: (17)..(17)
<223> OTHER INFORMATION: Gly or any amino acid from a heterologous
      signal peptide
<220> FEATURE:

<221> NAME/KEY: MOD_RES
<222> LOCATION: (18)..(18)
<223> OTHER INFORMATION: Asp or any amino acid from a heterologous signal peptide
<220> FEATURE:
<221> NAME/KEY: MOD_RES
<222> LOCATION: (19)..(19)
<223> OTHER INFORMATION: Trp or any amino acid from a heterologous signal peptide
<220> FEATURE:
<221> NAME/KEY: MOD_RES
<222> LOCATION: (20)..(20)
<223> OTHER INFORMATION: Gly or any amino acid from a heterologous signal peptide
<220> FEATURE:
<221> NAME/KEY: MOD_RES
<222> LOCATION: (21)..(21)
<223> OTHER INFORMATION: Ala or any amino acid from a heterologous signal peptide
<220> FEATURE:
<221> NAME/KEY: MOD_RES
<222> LOCATION: (22)..(22)
<223> OTHER INFORMATION: Glu or any amino acid from a heterologous signal peptide
<220> FEATURE:
<221> NAME/KEY: MOD_RES
<222> LOCATION: (23)..(23)
<223> OTHER INFORMATION: Ala or any amino acid from a heterologous signal peptide

<400> SEQUENCE: 56

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Cys Thr Cys Ser Pro Ser His Pro Gln
            20                  25                  30

Asp Ala Phe Cys Asn Ser Asp Ile Val Ile Arg Ala Lys Val Val Gly
        35                  40                  45

Lys Lys Leu Val Lys Glu Gly Pro Phe Gly Thr Leu Val Tyr Thr Ile
    50                  55                  60

Lys Gln Met Lys Met Tyr Arg Gly Phe Thr Lys Met Pro His Val Gln
65                  70                  75                  80

Tyr Ile His Thr Glu Ala Ser Glu Ser Leu Cys Gly Leu Lys Leu Glu
                85                  90                  95

Val Asn Lys Tyr Gln Tyr Leu Leu Thr Gly Arg Val Tyr Asp Gly Lys
            100                 105                 110

Met Tyr Thr Gly Leu Cys Asn Phe Val Glu Arg Trp Asp Gln Leu Thr
        115                 120                 125

Leu Ser Gln Arg Lys Gly Leu Asn Tyr Arg Tyr His Leu Gly Cys Asn
    130                 135                 140

Cys Lys Ile Lys Ser Cys Tyr Tyr Leu Pro Cys Phe Val Thr Ser Lys
145                 150                 155                 160

Asn Glu Cys Leu Trp Thr Asp Met Leu Ser Asn Phe Gly Tyr Pro Gly
                165                 170                 175

Tyr Gln Ser Lys His Tyr Ala Cys Ile Arg Gln Lys Gly Gly Tyr Cys
            180                 185                 190

Ser Trp Tyr Arg Gly Trp Ala Pro Pro Asp Lys Ser Ile Ile Asn Val
        195                 200                 205

Thr Asp Pro
    210
```

<210> SEQ ID NO 57
<211> LENGTH: 188
<212> TYPE: PRT
<213> ORGANISM: Homo sapiens
<220> FEATURE:
<223> OTHER INFORMATION: huTIMP3(K45S, F57N, I205F, A208G)

<400> SEQUENCE: 57

```
Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Phe Ile Asn Gly Thr Asp Pro
            180                 185
```

<210> SEQ ID NO 58
<211> LENGTH: 188
<212> TYPE: PRT
<213> ORGANISM: Homo sapiens
<220> FEATURE:
<223> OTHER INFORMATION: huTIMP3(K45S, F57N, A208G)

<400> SEQUENCE: 58

```
Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
```

145 150 155 160

Cys Ile Arg Gln Lys Gly Gly Tyr Cys Ser Trp Tyr Arg Gly Trp Ala
165 170 175

Pro Pro Asp Lys Ser Ile Ile Asn Gly Thr Asp Pro
180 185

<210> SEQ ID NO 59
<211> LENGTH: 188
<212> TYPE: PRT
<213> ORGANISM: Homo sapiens
<220> FEATURE:
<223> OTHER INFORMATION: huTIMP3(K45S, F57N, I205Y)

<400> SEQUENCE: 59

Cys Thr Cys Ser Pro Ser His Pro Gln Asp Ala Phe Cys Asn Ser Asp
1 5 10 15

Ile Val Ile Arg Ala Ser Val Val Gly Lys Lys Leu Val Lys Glu Gly
20 25 30

Pro Asn Gly Thr Leu Val Tyr Thr Ile Lys Gln Met Lys Met Tyr Arg
35 40 45

Gly Phe Thr Lys Met Pro His Val Gln Tyr Ile His Thr Glu Ala Ser
50 55 60

Glu Ser Leu Cys Gly Leu Lys Leu Glu Val Asn Lys Tyr Gln Tyr Leu
65 70 75 80

Leu Thr Gly Arg Val Tyr Asp Gly Lys Met Tyr Thr Gly Leu Cys Asn
85 90 95

Phe Val Glu Arg Trp Asp Gln Leu Thr Leu Ser Gln Arg Lys Gly Leu
100 105 110

Asn Tyr Arg Tyr His Leu Gly Cys Asn Cys Lys Ile Lys Ser Cys Tyr
115 120 125

Tyr Leu Pro Cys Phe Val Thr Ser Lys Asn Glu Cys Leu Trp Thr Asp
130 135 140

Met Leu Ser Asn Phe Gly Tyr Pro Gly Tyr Gln Ser Lys His Tyr Ala
145 150 155 160

Cys Ile Arg Gln Lys Gly Gly Tyr Cys Ser Trp Tyr Arg Gly Trp Ala
165 170 175

Pro Pro Asp Lys Ser Tyr Ile Asn Ala Thr Asp Pro
180 185

<210> SEQ ID NO 60
<211> LENGTH: 188
<212> TYPE: PRT
<213> ORGANISM: Homo sapiens
<220> FEATURE:
<223> OTHER INFORMATION: huTIMP3(K45S, F57N, I205Y, A208G)

<400> SEQUENCE: 60

Cys Thr Cys Ser Pro Ser His Pro Gln Asp Ala Phe Cys Asn Ser Asp
1 5 10 15

Ile Val Ile Arg Ala Ser Val Val Gly Lys Lys Leu Val Lys Glu Gly
20 25 30

Pro Asn Gly Thr Leu Val Tyr Thr Ile Lys Gln Met Lys Met Tyr Arg
35 40 45

Gly Phe Thr Lys Met Pro His Val Gln Tyr Ile His Thr Glu Ala Ser
50 55 60

Glu Ser Leu Cys Gly Leu Lys Leu Glu Val Asn Lys Tyr Gln Tyr Leu
65 70 75 80

```
Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Tyr Ile Asn Gly Thr Asp Pro
            180                 185


<210> SEQ ID NO 61
<211> LENGTH: 188
<212> TYPE: PRT
<213> ORGANISM: Homo sapiens
<220> FEATURE:
<223> OTHER INFORMATION: huTIMP3(K45N,V47T,F57N,K75N,P77T,K94N,E96T,
      R138T,G173T)

<400> SEQUENCE: 61

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Asn Met Thr His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 62
<211> LENGTH: 188
<212> TYPE: PRT
<213> ORGANISM: Homo sapiens
<220> FEATURE:
<223> OTHER INFORMATION: huTIMP3(K45N,V47T,F57N,K94N,E96T,R138T,G173T)

<400> SEQUENCE: 62

Cys Thr Cys Ser Pro Ser His Pro Gln Asp Ala Phe Cys Asn Ser Asp
```

-continued 1 5 10 15

Ile Val Ile Arg Ala Asn Val Thr Gly Lys Lys Leu Val Lys Glu Gly
20 25 30

Pro Asn Gly Thr Leu Val Tyr Thr Ile Lys Gln Met Lys Met Tyr Arg
35 40 45

Gly Phe Thr Lys Met Pro His Val Gln Tyr Ile His Thr Glu Ala Ser
50 55 60

Glu Ser Leu Cys Gly Leu Asn Leu Thr Val Asn Lys Tyr Gln Tyr Leu
65 70 75 80

Leu Thr Gly Arg Val Tyr Asp Gly Lys Met Tyr Thr Gly Leu Cys Asn
85 90 95

Phe Val Glu Arg Trp Asp Gln Leu Thr Leu Ser Gln Arg Lys Gly Leu
100 105 110

Asn Tyr Thr Tyr His Leu Gly Cys Asn Cys Lys Ile Lys Ser Cys Tyr
115 120 125

Tyr Leu Pro Cys Phe Val Thr Ser Lys Asn Glu Cys Leu Trp Thr Asp
130 135 140

Met Leu Ser Asn Phe Thr Tyr Pro Gly Tyr Gln Ser Lys His Tyr Ala
145 150 155 160

Cys Ile Arg Gln Lys Gly Gly Tyr Cys Ser Trp Tyr Arg Gly Trp Ala
165 170 175

Pro Pro Asp Lys Ser Ile Ile Asn Ala Thr Asp Pro
180 185

<210> SEQ ID NO 63
<211> LENGTH: 188
<212> TYPE: PRT
<213> ORGANISM: Homo sapiens
<220> FEATURE:
<223> OTHER INFORMATION: huTIMP3(K45N,V47T,K50N,V52T,F57N,V97N,K99T)

<400> SEQUENCE: 63

Cys Thr Cys Ser Pro Ser His Pro Gln Asp Ala Phe Cys Asn Ser Asp
1 5 10 15

Ile Val Ile Arg Ala Asn Val Thr Gly Lys Asn Leu Thr Lys Glu Gly
20 25 30

Pro Asn Gly Thr Leu Val Tyr Thr Ile Lys Gln Met Lys Met Tyr Arg
35 40 45

Gly Phe Thr Lys Met Pro His Val Gln Tyr Ile His Thr Glu Ala Ser
50 55 60

Glu Ser Leu Cys Gly Leu Lys Leu Glu Asn Asn Thr Tyr Gln Tyr Leu
65 70 75 80

Leu Thr Gly Arg Val Tyr Asp Gly Lys Met Tyr Thr Gly Leu Cys Asn
85 90 95

Phe Val Glu Arg Trp Asp Gln Leu Thr Leu Ser Gln Arg Lys Gly Leu
100 105 110

Asn Tyr Arg Tyr His Leu Gly Cys Asn Cys Lys Ile Lys Ser Cys Tyr
115 120 125

Tyr Leu Pro Cys Phe Val Thr Ser Lys Asn Glu Cys Leu Trp Thr Asp
130 135 140

Met Leu Ser Asn Phe Gly Tyr Pro Gly Tyr Gln Ser Lys His Tyr Ala
145 150 155 160

Cys Ile Arg Gln Lys Gly Gly Tyr Cys Ser Trp Tyr Arg Gly Trp Ala
165 170 175

Pro Pro Asp Lys Ser Ile Ile Asn Ala Thr Asp Pro 180 185

<210> SEQ ID NO 64
<211> LENGTH: 188
<212> TYPE: PRT
<213> ORGANISM: Homo sapiens
<220> FEATURE:
<223> OTHER INFORMATION: huTIMP3(K45S,K50N,V52T,F57N,V97N,K99T,R186N,
K188T)

<400> SEQUENCE: 64

```
Cys Thr Cys Ser Pro Ser His Pro Gln Asp Ala Phe Cys Asn Ser Asp
1               5                   10                  15

Ile Val Ile Arg Ala Ser Val Val Gly Lys Asn Leu Thr Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

<210> SEQ ID NO 65
<211> LENGTH: 188
<212> TYPE: PRT
<213> ORGANISM: Homo sapiens
<220> FEATURE:
<223> OTHER INFORMATION: huTIMP3(K45S,F57N,K94N,E96T,D110N,K112T,R138T,
G173T)

<400> SEQUENCE: 65

```
Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
```

```
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 66
<211> LENGTH: 188
<212> TYPE: PRT
<213> ORGANISM: Homo sapiens
<220> FEATURE:
<223> OTHER INFORMATION: huTIMP3(K45S,F57N,T63N,K65T,K94N,E96T,G173T)

<400> SEQUENCE: 66

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Asn Ile Thr Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 67
<211> LENGTH: 188
<212> TYPE: PRT
<213> ORGANISM: Homo sapiens
<220> FEATURE:
<223> OTHER INFORMATION: huTIMP3(K45N,V47T,K50N,V52T,F57N,V97N,K99T,
      R138T,R186N,K188T)

<400> SEQUENCE: 67

Cys Thr Cys Ser Pro Ser His Pro Gln Asp Ala Phe Cys Asn Ser Asp
1               5                   10                  15

Ile Val Ile Arg Ala Asn Val Thr Gly Lys Asn Leu Thr Lys Glu Gly
            20                  25                  30
```

```
Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 68
<211> LENGTH: 188
<212> TYPE: PRT
<213> ORGANISM: Homo sapiens
<220> FEATURE:
<223> OTHER INFORMATION: huTIMP3(K45S,F57N,T63N,K65T,K94N,E96T,Q126N,
      R138T)

<400> SEQUENCE: 68

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Asn Ile Thr Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Asn Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

```
<210> SEQ ID NO 69
<211> LENGTH: 188
<212> TYPE: PRT
<213> ORGANISM: Homo sapiens
<220> FEATURE:
<223> OTHER INFORMATION: huTIMP3(K45N,V47T,K50N,V52T,F57N,V97N,K99T,
      R186N,K188T)

<400> SEQUENCE: 69

Cys Thr Cys Ser Pro Ser His Pro Gln Asp Ala Phe Cys Asn Ser Asp
1               5                   10                  15

Ile Val Ile Arg Ala Asn Val Thr Gly Lys Asn Leu Thr Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 70
<211> LENGTH: 188
<212> TYPE: PRT
<213> ORGANISM: Homo sapiens
<220> FEATURE:
<223> OTHER INFORMATION: huTIMP3(K45N,V47T,K50N,V52T,V97N,K99T,R138T,
      R186N,K188T)

<400> SEQUENCE: 70

Cys Thr Cys Ser Pro Ser His Pro Gln Asp Ala Phe Cys Asn Ser Asp
1               5                   10                  15

Ile Val Ile Arg Ala Asn Val Thr Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
```

```
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 71
<211> LENGTH: 188
<212> TYPE: PRT
<213> ORGANISM: Homo sapiens
<220> FEATURE:
<223> OTHER INFORMATION: huTIMP3(K45S,F57N,H78N,Q80T,K94N,E96T,R138T,
      G173T)

<400> SEQUENCE: 71

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro Asn Val Thr Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 72
<211> LENGTH: 188
<212> TYPE: PRT
<213> ORGANISM: Homo sapiens
<220> FEATURE:
<223> OTHER INFORMATION: huTIMP3(K45S,F57N,K75N,P77T,K94N,E96T,R138T,
      G173T)

<400> SEQUENCE: 72

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
```

```
        35                  40                  45

Gly Phe Thr Asn Met Thr His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 73
<211> LENGTH: 188
<212> TYPE: PRT
<213> ORGANISM: Homo sapiens
<220> FEATURE:
<223> OTHER INFORMATION: huTIMP3(K45N,V47T,K50N,V52T,V97N,K99T,G173T,
      R186N,K188T)

<400> SEQUENCE: 73

Cys Thr Cys Ser Pro Ser His Pro Gln Asp Ala Phe Cys Asn Ser Asp
1               5                   10                  15

Ile Val Ile Arg Ala Asn Val Thr Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 74
<211> LENGTH: 188
```

<212> TYPE: PRT
<213> ORGANISM: Homo sapiens
<220> FEATURE:
<223> OTHER INFORMATION: huTIMP3(K45E,F57N,Q126N,R138T,G173T)

<400> SEQUENCE: 74

```
Cys Thr Cys Ser Pro Ser His Pro Gln Asp Ala Phe Cys Asn Ser Asp
1               5                   10                  15

Ile Val Ile Arg Ala Glu Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Asn Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

<210> SEQ ID NO 75
<211> LENGTH: 188
<212> TYPE: PRT
<213> ORGANISM: Homo sapiens
<220> FEATURE:
<223> OTHER INFORMATION: huTIMP3(K45S,F57N,T63N,K65T,K94N,E96T,R138T,
      G173T)

<400> SEQUENCE: 75

```
Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Asn Ile Thr Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
```

```
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 76
<211> LENGTH: 188
<212> TYPE: PRT
<213> ORGANISM: Homo sapiens
<220> FEATURE:
<223> OTHER INFORMATION: huTIMP3(K45S,K50N,V52T,F57N,V97N,K99T,R138T,
      R186N,K188T)

<400> SEQUENCE: 76

Cys Thr Cys Ser Pro Ser His Pro Gln Asp Ala Phe Cys Asn Ser Asp
1               5                   10                  15

Ile Val Ile Arg Ala Ser Val Val Gly Lys Asn Leu Thr Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 77
<211> LENGTH: 188
<212> TYPE: PRT
<213> ORGANISM: Homo sapiens
<220> FEATURE:
<223> OTHER INFORMATION: huTIMP3(K45S.K50N,V52T,F57N,V97N,K99T,G173T,
      R186N,K188T)

<400> SEQUENCE: 77

Cys Thr Cys Ser Pro Ser His Pro Gln Asp Ala Phe Cys Asn Ser Asp
1               5                   10                  15

Ile Val Ile Arg Ala Ser Val Val Gly Lys Asn Leu Thr Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
```

```
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 78
<211> LENGTH: 188
<212> TYPE: PRT
<213> ORGANISM: Homo sapiens
<220> FEATURE:
<223> OTHER INFORMATION: huTIMP3(K45N,V47T, F57N, K94N,E96T, G173T,
      R186N,K188T)

<400> SEQUENCE: 78

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 79
<211> LENGTH: 188
<212> TYPE: PRT
<213> ORGANISM: Homo sapiens
<220> FEATURE:
```

<223> OTHER INFORMATION: huTIMP3(K45N,V47T, F57N, K94N,E96T, D110N, K112T, R186N,K188T)

<400> SEQUENCE: 79

```
Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

<210> SEQ ID NO 80
<211> LENGTH: 188
<212> TYPE: PRT
<213> ORGANISM: Homo sapiens
<220> FEATURE:
<223> OTHER INFORMATION: huTIMP3(K45N,V47T, F57N, V97N,K99T, R138T, G173T)

<400> SEQUENCE: 80

```
Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Asn Asn Thr Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140
```

-continued

```
Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 81
<211> LENGTH: 188
<212> TYPE: PRT
<213> ORGANISM: Homo sapiens
<220> FEATURE:
<223> OTHER INFORMATION: huTIMP3(K45N,V47T, F57N, K99E G173T, R186N,
      K188T)

<400> SEQUENCE: 81

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Lys Leu Glu Val Asn Glu Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 82
<211> LENGTH: 188
<212> TYPE: PRT
<213> ORGANISM: Homo sapiens
<220> FEATURE:
<223> OTHER INFORMATION: huTIMP3(K45E, K49E, F57N, K94N,E96T, D110N,
      K112T, G173T, R186N,K188T)

<400> SEQUENCE: 82

Cys Thr Cys Ser Pro Ser His Pro Gln Asp Ala Phe Cys Asn Ser Asp
1               5                   10                  15

Ile Val Ile Arg Ala Glu Val Val Gly Glu Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60
```

```
Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 83
<211> LENGTH: 188
<212> TYPE: PRT
<213> ORGANISM: Homo sapiens
<220> FEATURE:
<223> OTHER INFORMATION: huTIMP3(K50N,V52T, K94N,E96T, R138T, G173T)

<400> SEQUENCE: 83

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 84
<211> LENGTH: 188
<212> TYPE: PRT
<213> ORGANISM: Homo sapiens
<220> FEATURE:
<223> OTHER INFORMATION: huTIMP3(K45E, K50N,V52T, K94N,E96T, D110N,
      K112T, R138T, G173T)
```

<400> SEQUENCE: 84

```
Cys Thr Cys Ser Pro Ser His Pro Gln Asp Ala Phe Cys Asn Ser Asp
1               5                   10                  15

Ile Val Ile Arg Ala Glu Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

<210> SEQ ID NO 85
<211> LENGTH: 188
<212> TYPE: PRT
<213> ORGANISM: Homo sapiens
<220> FEATURE:
<223> OTHER INFORMATION: huTIMP3(K50N,V52T, K94N,E96T, R138T, G173T, R186N,K188T)

<400> SEQUENCE: 85

```
Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160
```

-continued

```
Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 86
<211> LENGTH: 188
<212> TYPE: PRT
<213> ORGANISM: Homo sapiens
<220> FEATURE:
<223> OTHER INFORMATION: huTIMP3(K45E, F57N ,T63N,K65T, K94N,E96T ,
      G173T, R186N,K188T)

<400> SEQUENCE: 86

Cys Thr Cys Ser Pro Ser His Pro Gln Asp Ala Phe Cys Asn Ser Asp
1               5                   10                  15

Ile Val Ile Arg Ala Glu Val Val Gly Lys Lys Leu Val Lys Glu Gly
            20                  25                  30

Pro Asn Gly Thr Leu Val Tyr Asn Ile Thr Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 87
<211> LENGTH: 188
<212> TYPE: PRT
<213> ORGANISM: Homo sapiens
<220> FEATURE:
<223> OTHER INFORMATION: huTIMP3(K45N,V47T, F57N, K94N,E96T, D110N,
      K112T, G173T, R186Q,K188Q)

<400> SEQUENCE: 87

Cys Thr Cys Ser Pro Ser His Pro Gln Asp Ala Phe Cys Asn Ser Asp
1               5                   10                  15

Ile Val Ile Arg Ala Asn Val Thr Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80
```

```
Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Arg Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Gln Gln Gln Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 88
<211> LENGTH: 188
<212> TYPE: PRT
<213> ORGANISM: Homo sapiens
<220> FEATURE:
<223> OTHER INFORMATION: HuTIMP3(K45S, F57N, K94N, E96T, R138T, G173T)

<400> SEQUENCE: 88

Cys Thr Cys Ser Pro Ser His Pro Gln Asp Ala Phe Cys Asn Ser Asp
1               5                   10                  15

Ile Val Ile Arg Ala Ser Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 89
<211> LENGTH: 188
<212> TYPE: PRT
<213> ORGANISM: Homo sapiens
<220> FEATURE:
<223> OTHER INFORMATION: HuTIMP3(K45E, F57N, K94N, E96T, R138T, G173T)

<400> SEQUENCE: 89

Cys Thr Cys Ser Pro Ser His Pro Gln Asp Ala Phe Cys Asn Ser Asp
1               5                   10                  15
```

```
Ile Val Ile Arg Ala Glu Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 90
<211> LENGTH: 188
<212> TYPE: PRT
<213> ORGANISM: Homo sapiens
<220> FEATURE:
<223> OTHER INFORMATION: HuTIMP3(K45E, F57N, K94N, E96T, D110N, K112T,
      R138T, G173T)

<400> SEQUENCE: 90

Cys Thr Cys Ser Pro Ser His Pro Gln Asp Ala Phe Cys Asn Ser Asp
1               5                   10                  15

Ile Val Ile Arg Ala Glu Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
```

180 185

<210> SEQ ID NO 91
<211> LENGTH: 188
<212> TYPE: PRT
<213> ORGANISM: Homo sapiens
<220> FEATURE:
<223> OTHER INFORMATION: HuTIMP3(K45E, F57N, K94N, E96T, R138T, G173T, R186Q, K188Q)

<400> SEQUENCE: 91

Cys Thr Cys Ser Pro Ser His Pro Gln Asp Ala Phe Cys Asn Ser Asp
1 5 10 15

Ile Val Ile Arg Ala Glu Val Val Gly Lys Lys Leu Val Lys Glu Gly
20 25 30

Pro Asn Gly Thr Leu Val Tyr Thr Ile Lys Gln Met Lys Met Tyr Arg
35 40 45

Gly Phe Thr Lys Met Pro His Val Gln Tyr Ile His Thr Glu Ala Ser
50 55 60

Glu Ser Leu Cys Gly Leu Asn Leu Thr Val Asn Lys Tyr Gln Tyr Leu
65 70 75 80

Leu Thr Gly Arg Val Tyr Asp Gly Lys Met Tyr Thr Gly Leu Cys Asn
85 90 95

Phe Val Glu Arg Trp Asp Gln Leu Thr Leu Ser Gln Arg Lys Gly Leu
100 105 110

Asn Tyr Thr Tyr His Leu Gly Cys Asn Cys Lys Ile Lys Ser Cys Tyr
115 120 125

Tyr Leu Pro Cys Phe Val Thr Ser Lys Asn Glu Cys Leu Trp Thr Asp
130 135 140

Met Leu Ser Asn Phe Thr Tyr Pro Gly Tyr Gln Ser Lys His Tyr Ala
145 150 155 160

Cys Ile Gln Gln Gln Gly Gly Tyr Cys Ser Trp Tyr Arg Gly Trp Ala
165 170 175

Pro Pro Asp Lys Ser Ile Ile Asn Ala Thr Asp Pro
180 185

<210> SEQ ID NO 92
<211> LENGTH: 188
<212> TYPE: PRT
<213> ORGANISM: Homo sapiens
<220> FEATURE:
<223> OTHER INFORMATION: HuTIMP3(K45E, F57N, K94N, E96T, R138T, G173T, R186E)

<400> SEQUENCE: 92

Cys Thr Cys Ser Pro Ser His Pro Gln Asp Ala Phe Cys Asn Ser Asp
1 5 10 15

Ile Val Ile Arg Ala Glu Val Val Gly Lys Lys Leu Val Lys Glu Gly
20 25 30

Pro Asn Gly Thr Leu Val Tyr Thr Ile Lys Gln Met Lys Met Tyr Arg
35 40 45

Gly Phe Thr Lys Met Pro His Val Gln Tyr Ile His Thr Glu Ala Ser
50 55 60

Glu Ser Leu Cys Gly Leu Asn Leu Thr Val Asn Lys Tyr Gln Tyr Leu
65 70 75 80

Leu Thr Gly Arg Val Tyr Asp Gly Lys Met Tyr Thr Gly Leu Cys Asn
85 90 95

Phe Val Glu Arg Trp Asp Gln Leu Thr Leu Ser Gln Arg Lys Gly Leu

```
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Glu Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 93
<211> LENGTH: 188
<212> TYPE: PRT
<213> ORGANISM: Homo sapiens
<220> FEATURE:
<223> OTHER INFORMATION: HuTIMP3(K45E, F57N, K94N, E96T, R138T, G173T,
      K188E)

<400> SEQUENCE: 93

Cys Thr Cys Ser Pro Ser His Pro Gln Asp Ala Phe Cys Asn Ser Asp
1               5                   10                  15

Ile Val Ile Arg Ala Glu Val Val Gly Lys Lys Leu Val Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Glu Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 94
<211> LENGTH: 188
<212> TYPE: PRT
<213> ORGANISM: Homo sapiens
<220> FEATURE:
<223> OTHER INFORMATION: HuTIMP3(K45E, F57N, K94N, E96T, R138T, G173T,
      R186N, K188T)

<400> SEQUENCE: 94

Cys Thr Cys Ser Pro Ser His Pro Gln Asp Ala Phe Cys Asn Ser Asp
1               5                   10                  15

Ile Val Ile Arg Ala Glu Val Val Gly Lys Lys Leu Val Lys Glu Gly
```

```
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Asn Gln Thr Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

<210> SEQ ID NO 95
<211> LENGTH: 188
<212> TYPE: PRT
<213> ORGANISM: Homo sapiens
<220> FEATURE:
<223> OTHER INFORMATION: HuTIMP3(K45E, K50N, V52T, K94N, E96T, D110N, K112T, R138T, G173T)

<400> SEQUENCE: 95

```
Cys Thr Cys Ser Pro Ser His Pro Gln Asp Ala Phe Cys Asn Ser Asp
1               5                   10                  15

Ile Val Ile Arg Ala Glu Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

```
<210> SEQ ID NO 96
<211> LENGTH: 188
<212> TYPE: PRT
<213> ORGANISM: Homo sapiens
<220> FEATURE:
<223> OTHER INFORMATION: HuTIMP3(K45E, K50N, V52T, K94N, E96T, R138T,
      G173T, K188E)

<400> SEQUENCE: 96

Cys Thr Cys Ser Pro Ser His Pro Gln Asp Ala Phe Cys Asn Ser Asp
1               5                   10                  15

Ile Val Ile Arg Ala Glu Val Val Gly Lys Asn Leu Thr Lys Glu Gly
            20                  25                  30

Pro Phe Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Glu Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 97
<211> LENGTH: 188
<212> TYPE: PRT
<213> ORGANISM: Homo sapiens
<220> FEATURE:
<223> OTHER INFORMATION: HuTIMP3(K50N, V52T, F57N, K94N, E96T, R138T,
      G173T)

<400> SEQUENCE: 97

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asp Gly Lys Met Tyr Thr Gly Leu Cys Asn
                85                  90                  95

Phe Val Glu Arg Trp Asp Gln Leu Thr Leu Ser Gln Arg Lys Gly Leu
            100                 105                 110
```

```
Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Thr Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 98
<211> LENGTH: 188
<212> TYPE: PRT
<213> ORGANISM: Homo sapiens
<220> FEATURE:
<223> OTHER INFORMATION: HuTIMP3(K50N, V52T, F57N, K94N, E96T, D110N,
      K112T, R138T)

<400> SEQUENCE: 98

Cys Thr Cys Ser Pro Ser His Pro Gln Asp Ala Phe Cys Asn Ser Asp
1               5                   10                  15

Ile Val Ile Arg Ala Lys Val Val Gly Lys Asn Leu Thr Lys Glu Gly
            20                  25                  30

Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185


<210> SEQ ID NO 99
<211> LENGTH: 188
<212> TYPE: PRT
<213> ORGANISM: Homo sapiens
<220> FEATURE:
<223> OTHER INFORMATION: HuTIMP3(K45E, F57N, K94N, E96T, D110N, K112T,
      R138T)

<400> SEQUENCE: 99

Cys Thr Cys Ser Pro Ser His Pro Gln Asp Ala Phe Cys Asn Ser Asp
1               5                   10                  15

Ile Val Ile Arg Ala Glu Val Val Gly Lys Lys Leu Val Lys Glu Gly
            20                  25                  30
```

-continued

```
Pro Asn Gly Thr Leu Val Tyr Thr Ile Lys Gln Met Lys Met Tyr Arg
        35                  40                  45

Gly Phe Thr Lys Met Pro His Val Gln Tyr Ile His Thr Glu Ala Ser
    50                  55                  60

Glu Ser Leu Cys Gly Leu Asn Leu Thr Val Asn Lys Tyr Gln Tyr Leu
65                  70                  75                  80

Leu Thr Gly Arg Val Tyr Asn Gly Thr Met Tyr Thr Gly Leu Cys Asn
                85                  90                  95

Phe Val Glu Arg Trp Asp Gln Leu Thr Leu Ser Gln Arg Lys Gly Leu
            100                 105                 110

Asn Tyr Thr Tyr His Leu Gly Cys Asn Cys Lys Ile Lys Ser Cys Tyr
        115                 120                 125

Tyr Leu Pro Cys Phe Val Thr Ser Lys Asn Glu Cys Leu Trp Thr Asp
    130                 135                 140

Met Leu Ser Asn Phe Gly Tyr Pro Gly Tyr Gln Ser Lys His Tyr Ala
145                 150                 155                 160

Cys Ile Arg Gln Lys Gly Gly Tyr Cys Ser Trp Tyr Arg Gly Trp Ala
                165                 170                 175

Pro Pro Asp Lys Ser Ile Ile Asn Ala Thr Asp Pro
            180                 185
```

VARIANTS OF TISSUE INHIBITOR OF METALLOPROTEINASE TYPE THREE (TIMP-3), COMPOSITIONS AND METHODS

CROSS REFERENCE TO RELATED APPLICATIONS

This application is a national state application under 35. U.S.C. § 371 of International Application No. PCT/US2014/026811 filed Mar. 13, 2014 which claims the benefit of, and priority to, U.S. Provisional Application No. 61/782,613 filed Mar. 14, 2013; U.S. Provisional Application No. 61/798,160 filed Mar. 15, 2013; U.S. Provisional Application No. 61/802,988 filed Mar. 18, 2013; and U.S. Provisional Application No. 61/940,673 filed Feb. 17, 2014 and which are incorporated herein by reference in their entirety.

REFERENCE TO A SEQUENCE LISTING

The present application is being filed along with a Sequence Listing in electronic format. The Sequence Listing is provided as a file, entitled A-1827WOPCT_SL31314 created Mar. 11, 2014, which is 306 KB in size. The information in the electronic format of the Sequence Listing is incorporated herein by reference in its entirety.

FIELD OF THE INVENTION

The present invention relates in general to metalloproteinase inhibitors. In particular, the invention relates to tissue inhibitor of metalloproteinase 3 ("TIMP-3") and novel, useful variants, muteins and derivatives thereof.

BACKGROUND OF THE INVENTION

Connective tissues and articular cartilage are maintained in dynamic equilibrium by the opposing effects of extracellular matrix synthesis and degradation. Degradation of the matrix is brought about primarily by the enzymatic action of metalloproteinases, including matrix metalloproteinases (MMPs) and disintegrin-metalloproteinases with thrombospondin motifs (ADAMTSs). While these enzymes are important in many natural processes (including development, morphogenesis, bone remodeling, wound healing and angiogenesis), disregulation of these enzymes leading to their elevated levels are believed to play a detrimental role in degradative diseases of connective tissue, including rheumatoid arthritis and osteoarthritis, as well as in cancer and cardiovascular conditions.

Endogenous inhibitors of metalloproteinases include plasma alpha2-macroglobulin and tissue inhibitors of metalloproteinases (TIMPs), of which there are four known to be encoded in the human genome. TIMP-3 inhibits all the major cartilage-degrading metalloproteases, and multiple lines of evidence indicate that it protects cartilage. Addition of the protein to cartilage-explants prevents cytokine-induced degradation, and intra-articular injection reduces cartilage damage in the rat medial meniscal tear model of osteoarthritis.

Dysregulation of MMPs also occurs in congestive heart failure and is thought to play a role in numerous proinflammatory processes. However, development of TIMP-3 as a therapeutic inhibitor of MMP activity has been hampered by challenges in production of recombinant protein and short half-life of recombinant forms of TIMP-3. Accordingly, there is a need in the art for forms of TIMP-3 that exhibit favorable production, purification and pharmacokinetic/pharmacodynamic properties.

BRIEF DESCRIPTION OF THE DRAWINGS

FIG. 1 presents an alignment of native, full-length human TIMP-3 and a mutated form of full-length human TIMP-3 in which the letter "X" has been substituted for particular amino acids within the sequence. The signal sequence is underlined; other signal sequences can be substituted therefore, as described herein.

FIG. 2 presents an alignment of native, full-length human TIMP-3, and a TIMP-3 variant in which certain amino acid substitutions have been made. The signal sequence is present and underlined for the native, full-length TIMP-3 sequence to maintain consistency of numbering; other signal sequences can be substituted therefore, as described herein.

FIG. 4 presents an alignment of native, human N-terminal TIMP3 and a mutated form of human N-terminal TIMP3 in which the letter "X" has been substituted for particular amino acids within the sequence. The signal sequence is underlined; other signal sequences can be substituted therefore, as described herein. Certain substitutions are envisioned in the mature form of N-terminal TIMP-3, and are designated herein as "n # m" where "n" designates the amino acid found in the native, N-terminal domain of TIMP-3, "#" designates the amino acid residue number, and "m" designates the amino acid that has been substituted (a '-' indicates that the amino acid has been deleted). Thus, for example, "K45I" indicates that the lysine (K) at amino acid 45 has been substituted with isoleucine (I). Deletion of M67 is denoted by M67-. Replacement of residues 71-77 with a pair of glycines is denoted by Y70-GG-H78. The mutated forms of human TIMP-3 exemplified herein comprise the following mutations (alone, or in combination): R43F, K45I, K45T, K53T, E54Y, K65T, M67-, K68T, K68I, Y70-GG-H78, H78W. Specific combinations of mutations include K45I, K53T, E54Y, K65T, M67-, K68T; K45I, K53T, E54Y, M67-, K68I; K45I, K53T, K65T, M67-, K68T; K45I, K53T, M67-, K68I; K45I, K53T, M67-, K68I, H78W; K45I, K65T, K68I; K45I, K65T, M67-, K68T; K45I, K65T, M67-, K68T, H78W; K45I, M67-, K68I, H78W; K45I, M67-, K68T; K45T, K65T, M67-, K68I; K45T, K65T, M67-, K68T; K53T, E54Y; K53T, H78W; R43F, K45I, K65T, K68I.

FIG. 5 presents an alignment of native, human N-terminal TIMP3 and a mutated form of human N-terminal TIMP3 in which the letter "X" has been substituted for particular amino acids within the sequence. The signal sequence is underlined; other signal sequences can be substituted therefore, as described herein. Certain substitutions are envisioned in the mature form of N-terminal TIMP-3, and are designated herein as "n # m" where "n" designates the amino acid found in the native, N-terminal domain of TIMP-3, "#" designates the amino acid residue number, and "m" designates the amino acid that has been substituted (a '-' indicates that the amino acid has been deleted). Thus, for example, "K45E" indicates that the lysine (K) at amino acid 45 has been substituted with glutamine (E). The mutated forms of human TIMP-3 exemplified herein comprise the following mutations (alone, or in combination): T25G; T25H; T25K; T25P; T25R; T25S; T25W; C26A; S27V; S27A; P28A;

Figure 3:
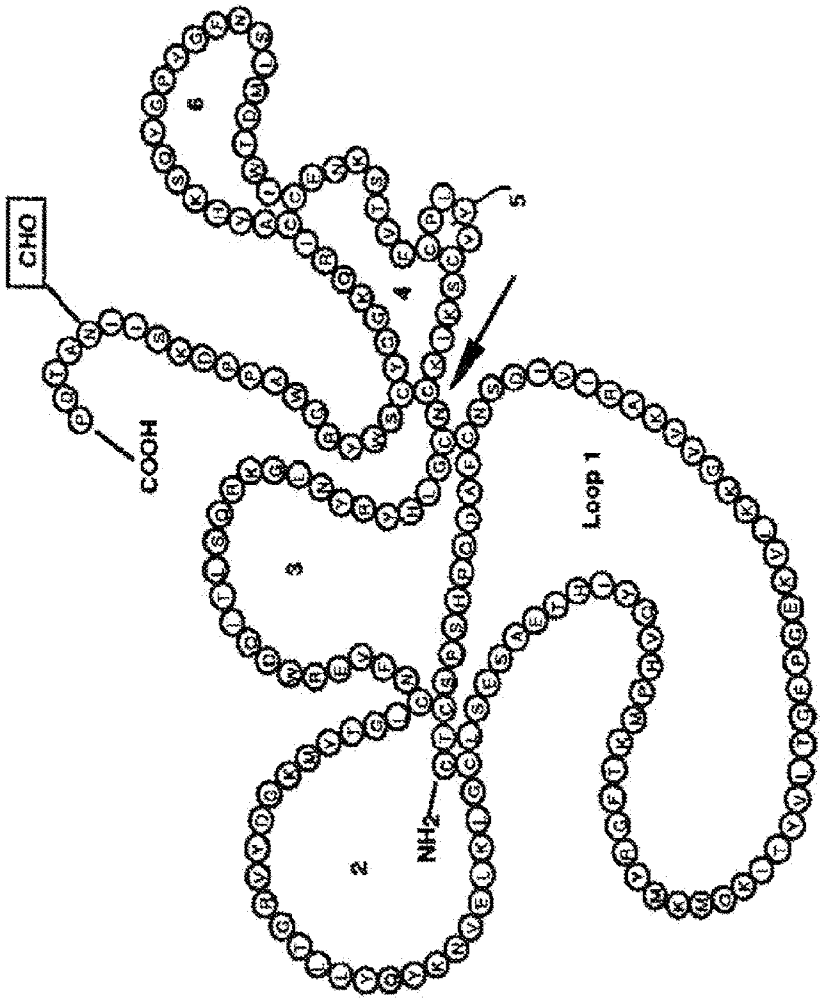
FIG. 3 presents a two dimensional polypeptide map wherein amino acids are arrayed to identify those residues comprising TIMP-3's N-domain (residues 23-143) and C-Domain (144-211), as well as the cysteine positions that form disulfide bonds.

P28D; P28L; P28S; S29I; H30A; P31A; Q32A; F35A; C36A; N37A; D39A; V41A; I42A; R43A; R43E; R43T; K45E;V46A; G48A; G48S; K49S; K49E; L51E; L51T; K53D; E54S; P56N; L60I; V61Q; T63E; T74E; H78D; H78E; Q80E; G116T; C118A; N119D; C143A; and 144N-. Specific combinations of mutations include: S27V S29I; V46A G48S K49E L51E K53D E54S P56N L60I V61Q G116T N119D; C26A C118A; C36A C143A; K45E K49E; K45E K49S; K45E Q80E; K45E T63E; K45E T63E H78E; K45E T63E H78E Q80E; L51T T74E H78D; R43E T74E H78D Q80E; R43T T74E H78D Q80E; T63E H78D; T63E H78E; T63E H78E Q80E; T63E T74E H78D; T63E T74E H78E; T74E H78D Q80E; T74E H78E Q80E; Y70-GG-78H.

FIG. 6 presents an alignment of native TIMP-2 and native TIMP-3. Identity of the amino acids in a corresponding residue is indicated by an asterisk beneath the sequences.

SUMMARY OF THE INVENTION

In one embodiment, the invention provides an isolated TIMP-3 mutein having a mature region that is at least 95% identical in amino acid sequence to the mature region of TIMP-3 set forth in SEQ ID NO:2, having at least one mutation, the mutation being selected from the group consisting of K45E; K45N; K45S; V47T; K49N; K49E; K49S; K50N; L51T; L51N; V52T; K53T; P56N; F57N; G58T; T63E; T63N; K65T; K65N; M67T; K68S; T74E; K75N; P77T; H78D; H78E; H78N; Q80E; Q80T; K94N; E96T; E96N; V97N; N98T; K99T; D110N; K112T; Q126N; K133S; R138T; R138N; H140T; T158N; K160T; T166N; M168T; G173T; H181N; A183T; R186N; R186Q, R186E, K188T; K188Q, K188E, P201N; K203T; I205F, I205Y, A208G, A208V, and A208Y.

In another embodiment of the invention, there is provided an isolated TIMP-3 mutein having a mature region that is at least 95% identical in amino acid sequence to the mature region of TIMP-3 set forth in SEQ ID NO:2, having, having the mutation F57N and at least one further mutation, wherein the mutation is substitution at one or more of K residues of TIMP-3. In a further aspect of the invention, the further mutation introduces an N-linked glycosylation site into the amino acid sequence.

Also embodied within the invention is an isolated TIMP-3 mutein having a mature region that is at least 90% identical in amino acid sequence to the mature region of TIMP-3 set forth in SEQ ID NO:2, wherein the mutein has at least one mutation that introduces at least one N-linked glycosylation site into the amino acid sequence. In an additional embodiment, the TIMP-3 mutein has two, three, four, five or six N-linked glycosylation sites; in a still further embodiment, the number of N-linked glycosylation sites introduced is seven, eight, nine or ten.

In one embodiment of the invention, the N-linked glycosylation site is introduced at a region of the TIMP-3 amino acid sequence selected from the group consisting of: the region comprising amino acids 48-54; the region comprising amino acids 93-100; the region comprising amino acids 121-125; the region comprising amino acids 143-152; amino acids 156-164; the region comprising amino acids 183-191; and combinations thereof. In an additional embodiment, the TIMP-3 mutein has two, three, four, or five N-linked glycosylation sites; in a still further embodiment, the number of N-linked glycosylation sites introduced is six, seven, eight, nine or ten.

Further provided is an isolated TIMP-3 mutein having a mature region that is at least 95% identical in amino acid sequence to the mature region of TIMP-3 set forth in SEQ ID NO:2, wherein the mutein has at least one mutation selected from the group consisting of: (a) one or more mutations in a TIMP-3 surface exposed positively charged patch that results in changes in the characteristics of the TIMP-3 charged patch that mimic a TIMP-2 charged surface; (b) one or more mutations that reduce susceptibility to proteolytic cleavage; (c) one or more mutations that result in decreased interaction of the TIMP-3 mutein with the scavenger receptor LRP-1; (d) one or more mutations that result in decreased interaction of the TIMP-3 mutein heparin or extracellular matrix components; (e) addition of one or more cysteinyl residues to the native TIMP-3 sequence; (f) improved pharmacokinetic and/or pharmacodynamic properties; and (g) combinations of the mutations set forth in (a)-(f). In one embodiment, the mutation or mutations is or are introduced at a region of the TIMP-3 amino acid sequence selected from the group consisting of: the region comprising amino acids 48-54; the region comprising amino acids 93-100; the region comprising amino acids 121-125; the region comprising amino acids 143-152; amino acids 156-164; the region comprising amino acids 183-191; and combinations thereof.

One aspect of the invention is an isolated nucleic acid that encodes a TIMP-3 mutein according to any one of the aforementioned TIMP-3 muteins. Other aspects of the invention are an expression vector comprising such isolated nucleic acid; an isolated host cell transformed or transfected with the expression vector; and a method of producing a recombinant TIMP-3 mutein comprising culturing the transformed or transfected host cell of under conditions promoting expression of the TIMP-3 mutein, and recovering the TIMP-3 mutein.

Further provided is a composition comprising the TIMP-3 mutein described herein, as well as a method of treating a condition in which matrix metalloproteases (MMPs) and/or other proteinases that are inhibited or inhibitable by TIMP-3 play a causative or exacerbating role, comprising administering to an individual afflicted with such a condition, an amount of such composition sufficient to treat the condition.

In one embodiment, the condition is selected from the group consisting of inflammatory conditions, osteoarthritis, myocardial ischemia, reperfusion injury, and progression to congestive heart failure. In another embodiment, the condition is selected from the group consisting of asthma, chronic obstructive pulmonary disease (COPD), and idiopathic pulmonary fibrosis (IPF), inflammatory bowel disease (for example, ulcerative colitis, Crohn's disease, and celiac disease), psoriases, myocarditis including viral myocarditis, inflammation related to atherosclerosis, and arthritic conditions including rheumatoid arthritis and psoriatic arthritis.

In a further embodiment, the condition is selected from the group consisting of dystrophic epidermolysis bullosa, osteoarthritis, Reiter's syndrome, pseudogout, rheumatoid arthritis including juvenile rheumatoid arthritis, ankylosing spondylitis, scleroderma, periodontal disease, ulceration including corneal, epidermal, or gastric ulceration, wound healing after surgery, restenosis, emphysema, Paget's disease of bone, osteoporosis, scleroderma, pressure atrophy of bone or tissues as in bedsores, cholesteatoma, abnormal wound healing, rheumatoid arthritis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease, ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis, pancreatitis, insulin-dependent diabetes mellitus, mastitis, cholecystitis, cholangitis, pericholangitis, multiple sclerosis (MS), asthma (including extrinsic and intrinsic asthma as well as related chronic inflammatory conditions, or hyperresponsiveness, of the airways), chronic obstructive pulmonary disease (COPD. i.e., chronic bronchitis, emphysema), Acute Respiratory Disorder Syndrome (ARDS), respiratory distress syndrome, cystic fibrosis, pulmonary hypertension, pulmonary vasoconstriction, acute lung injury, allergic bronchopulmonary aspergillosis, hypersensitivity pneumonia, eosinophilic pneumonia, bronchitis, allergic bronchitis bronchiectasis, tuberculosis, hypersensitivity pneumonitis, occupational asthma, asthma-like disorders, sarcoid, reactive airway disease (or dysfunction) syndrome, byssinosis, interstitial lung disease, hyper-eosinophilic syndrome, rhinitis, sinusitis, and parasitic lung disease, airway hyperresponsiveness associated with viral-induced conditions (for example, respiratory syncytial virus (RSV), parainfluenza virus (PIV), rhinovirus (RV) and adenovirus), Guillain-Barre disease, Graves' disease, Addison's disease, Raynaud's phenomenon, autoimmune hepatitis, graft versus host disease (GVHD), cerebral ischemia, traumatic brain injury, multiple sclerosis, neuropathy, myopathy, spinal cord injury, and amyotrophic lateral sclerosis (ALS).

DETAILED DESCRIPTION OF THE INVENTION

The present invention provides compositions, kits, and methods relating to TIMP-3 polypeptides, variants, derivatives or muteins. Also provided are nucleic acids, and derivatives and fragments thereof, comprising a sequence of nucleotides that encodes all or a portion of such a TIMP-3 polypeptide, variant, derivative or mutein, e.g., a nucleic acid encoding all or part of such TIMP-3 polypeptides, variants, derivatives or muteins; plasmids and vectors comprising such nucleic acids, and cells or cell lines comprising such nucleic acids and/or vectors and plasmids. The provided methods include, for example, methods of making, identifying, or isolating TIMP-3 polypeptides, variants, derivatives or muteins that exhibit desirable properties.

Numerous conditions exist in which it would be advantageous to augment endogenous TIMP-3 in a mammal, or to increase the level of TIMP-3 in a particular tissue. Accordingly, also provided herein are methods of making compositions, such as pharmaceutical compositions, comprising a TIMP-3 polypeptide, variant, derivative or mutein, and methods for administering a composition comprising a TIMP-3 polypeptide, variant, derivative or mutein to a subject, for example, a subject afflicted with a condition in which dysregulation of matrix metalloproteinase activity results in excessive or inappropriate remodeling of tissue.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated" as used to characterize a molecule (where the molecule is, for example, a polypeptide, a polynucleotide, or an antibody) indicates that the molecule by virtue of its origin or source of derivation (1) is not associated with naturally associated components that accompany it in its native state, (2) is substantially free of other molecules from the same species (3) is expressed by a cell from a different species, or (4) does not occur in nature without human intervention. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently, or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence or a tag protein).

A "variant" or "mutein" of a polypeptide (e.g., a TIMP-3 variant or mutein) comprises an amino acid sequence wherein one or more amino acid residues are inserted into, deleted from and/or substituted into the amino acid sequence relative to another polypeptide sequence. Variants of the invention include fusion proteins.

A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991), which are each incorporated herein by reference.

One way of referring to the degree of similarity of a variant or mutein to the native protein is by referring to the percent identity between the two (or more) polypeptide sequences, or the encoding nucleic acids sequences, being compared. The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

A "derivative" of a polypeptide is a polypeptide (e.g., a TIMP-3 polypeptide, variant or mutein) that has been chemically modified, e.g., via conjugation to another chemical moiety (such as, for example, polyethylene glycol or albumin, e.g., human serum albumin), phosphorylation, and/or glycosylation.

Polynucleotide and polypeptide sequences are indicated using standard one- or three-letter abbreviations. Unless otherwise indicated, each polypeptide sequence has an amino terminus at the left and a carboxy terminus at the right; each single-stranded nucleic acid sequence, and the top strand of each double-stranded nucleic acid sequence, has a 5' terminus at the left and a 3' terminus at the right. A particular polypeptide or polynucleotide sequence also can be described by explaining how it differs from a reference sequence. For example, substitutions of amino acids are designated herein as "n # m" where "n" designates the amino acid found in the native, full-length polypeptide, "#" designates the amino acid residue number, and "m" designates the amino acid that has been substituted.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding a TIMP-3 polypeptide, fragment, variant, derivative or mutein, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

Naturally occurring extracellular proteins typically include a "signal sequence," which directs the protein into the cellular pathway for protein secretion and which is not present in the mature protein. The signal sequence may also be referred to as a "signal peptide" or "leader peptide" and is enzymatically cleaved from the extracellular protein. The protein that has been so processed (i.e., having the signal sequence removed) is often referred to as "mature" protein. A polynucleotide encoding a protein or polypeptide of the invention may encode a naturally occurring signal sequence or a heterologous signal sequence, numerous of which are known in the art.

As appreciated by one of skill in the art, recombinant proteins or polypeptides in accordance with the present embodiments can be expressed in cell lines, including mammalian cell lines. Sequences encoding particular proteins can be used for transformation of a suitable mammalian host cell. Transformation can be by any known method for introducing polynucleotides into a host cell, including, for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740, 461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells.

Typically, a host cell is a cultured cell that can be transformed or transfected with a polypeptide-encoding nucleic acid, which can then be expressed in the host cell. In a "transient transfection," the nucleic acid is introduced into the host cell by one of several methods known in the art, and the recombinant protein is expressed for a finite period of time, typically up to about four days, before the nucleic acid is lost or degraded, for example, when the host cell undergoes mitosis. If a "stable transfection" is desired, the polypeptide-encoding nucleic acid may be introduced into the host cell along with a nucleic acid encoding a selectable marker. Use of a selectable marker allows one of skill in the art to select transfected host cells in which the polypeptide-encoding nucleic acid is integrated into the host cell genome in such a way that the polypeptide-encoding nucleic acid is maintained through mitosis, and can be expressed by progeny cells.

The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

As used herein, "TIMP-3 DNA," "TIMP-3-encoding DNA" and the like indicate a selected TIMP-3 encoding nucleic acid in which the TIMP-3 that is expressed therefrom may be either native TIMP-3 or a TIMP-3 variant or mutein as described herein. Likewise, "TIMP-3,""TIMP-3 protein" and "TIMP-3 polypeptide" are used to designate either a native TIMP-3 protein or a TIMP-3 protein comprising one or more mutations (i.e., a TIMP-3 polypeptide, variant, derivative or mutein). A particular mutein of TIMP-3 may be designated by the mutation or mutations, for example, "K45N TIMP-3" or "K45N TIMP-3 polypeptide" indicates a polypeptide in which the lysine (K) at amino acid 45 of native TIMP-3 has been substituted with an asparagine (N).

The term "native TIMP-3" as used herein refers to wild type TIMP-3. TIMP-3 is expressed by various cells or tissues in a mammal and is present in the extracellular matrix; the TIMP-3 that is so expressed is also referred to herein as "endogenous" TIMP-3. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. The amino acid numbering system used in U.S. Pat. No. 6,562,596 designates the amino acids in the signal (or leader) peptide with negative numbers, and references the mature protein (i.e., the protein from which the signal or leader peptide has been removed) as amino acids 1-188. The numbering systems used herein refers to TIMP-3 with the first amino acid of the native leader peptide designated #1; the full-length TIMP-3 thus includes amino acids 1-211, and the mature form is amino acids 24-211. Those of ordinary skill in the art readily comprehend the differences in amino acid numbering that may occur by the use of these different numbering systems, and can thus easily apply the numbering system used herein to, for example, a TIMP-3 polypeptide in which the first amino acid of the mature form is referred to as #1. Thus, for example, K45N as designated herein would be designated K22N using the numbering system of U.S. Pat. No. 6,562,596.

TIMP-3 is formed of two domains, an N-terminal domain comprising amino acids 24 through 143 of TIMP-3 (i.e., about two-thirds of the molecule), and the C-terminal domain, which comprises amino acids 144 though 211. FIG. 3 presents a 2 dimensional polypeptide array of TIMP-3, highlighting the complex nature of the disulphide bonds that facilitate formation of the secondary and tertiary structure TIMP-3. The N-terminal domain of TIMP-3, often referred to as "N-TIMP-3," has been found to exhibit at least some of the biological activities of TIMP-3; accordingly, TIMP-3 variants, derivatives and muteins as described herein comprehend variants, derivatives and muteins of a fragment of TIMP-3 that comprises the N-terminal domain.

Native TIMP-3 protein presents several challenges for its use as a therapeutic molecule. For example, mammalian expression titers for TIMP-3 protein using standard mammalian expression techniques are too low to allow sufficient quantities of TIMP-3 to be produced at a scale that is suitable for a therapeutic protein. Moreover, the binding of TIMP-3 to extracellular matrix necessitates the inclusion of heparin (or a similar agent that reduces binding of TIMP-3 to extracellular matrix) in cell culture medium, and binding to the Low density lipoprotein Receptor-related Protein 1 (LRP1) scavenger protein exacerbates the challenge of secretion of recombinant TIMP-3 into the medium at a level that allows a production-scale process to be developed.

Microbial production in prokaryotic cells of full-length TIMP-3 has proved difficult due to incorrect folding of the protein.

Accordingly, the TIMP-3 variants or muteins of the invention have been modified to overcome one or more of these challenges. Polypeptides of the invention include polypeptides that have been modified in any way and for any reason, for example, to: (1) reduce susceptibility to proteolysis, (2) reduce susceptibility to oxidation, (3) reduce the need for agents that inhibit binding of TIMP-3 to extracellular matrix in cell culture, (4) alter binding affinities for other moieties, for example scavenger receptors such as LRP-1, (5) confer or modify other physicochemical or functional properties, including pharmacokinetics and/or pharmacodynamics, (6) facilitate expression and/or purification of recombinant protein. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). Consensus sequences can be used to select amino acid residues for substitution; those of skill in the art recognize that additional amino acid residues may also be substituted.

In one aspect of the invention, there is provided a TIMP-3 mutein or variant that will exhibit an increase in expression levels of the mutein or variant over that observed with native TIMP-3; in another aspect of the invention the increased expression occurs in a mammalian cell expression system. Expression levels may be determined by any suitable method that will allow a quantitative or semi-quantitative analysis of the amount or recombinant TIMP-3 (native, variant or mutein) in cell culture supernatant fluid, i.e., conditioned media (CM). In one embodiment, samples or CM are assessed by Western blot; in another embodiment, CM samples are assessed using a standard human TIMP-3 ELISA.

In one embodiment, the increase in expression is observed in a transient expression system; in another embodiment, the increase in expression is observed in a stable transfection system. One embodiment provides a TIMP-3 mutein or variant for which the increase in expression observed is two-fold (2×) greater than that observed for native TIMP-3; another embodiment provides a TIMP-3 mutein or variant for which the increase in expression observed is five-fold (5×) greater than that observed for native TIMP-3. Further embodiments include TIMP-3 muteins or variants for which the increase in expression is three-fold (3×), four-fold (4×) or six-fold (6×). In one embodiment, the expression of the TIMP-3 mutein or variant is ten-fold (10×) greater than that observed with native TIMP-3; in another embodiment, the observed expression is more than ten-fold, for example, 20-fold (20×) or greater, than that observed with native TIMP-3

In another aspect of the invention, there are provided TIMP-3 muteins (or variants) that exhibit reduced requirement for the addition of heparin (or another agent that inhibits binding of TIMP-3 to extracellular matrix) to cell culture media. The reduction in the amount of heparin (or other agent) may be described in a semi-quantitative manner, i.e., the reduction may be partial, moderate, substantial, or complete. In another embodiment, the reduction is expressed as a percentage, for example the amount of heparin (or similar agent) may be reduced by 10%, 20%, 30%, 40%, 50%, or more (for example by 60%, 70% 80%, 90% or 100%).

In one embodiment, there are provided TIMP-3 variants or muteins comprising inserted glycosylation sites. As is known in the art, glycosylation patterns can depend on both the sequence of the protein (e.g., the presence or absence of particular glycosylation amino acid residues, discussed below), or the host cell or organism in which the protein is produced. Particular expression systems are discussed below. The presence, absence, or degree of glycosylation may be determined by any method that is known to one of skill in the art, including semiqualitative measures of shifts in molecular weight (MW) as observed by western blotting or from coomassie stained SDS-PAGE gels, while quantitative measures can include utilizing mass spectrophotometer techniques and observation of mw shifts corresponding to addition of Asparagine-linked glycosylation, or through observation of mass shift with the removal of Asparagine-linked glycosylation by an enzyme such as Peptide —N-Glycosidase F (PNGase-F; SigmaAldrich, St. Louis, Mo.).

Glycosylation of polypeptides is typically either N-linked or O-linked. N-linked refers to the attachment of the carbohydrate moiety to the side chain of an asparagine residue. The tri-peptide sequences asparagine-X-serine (N X S) and asparagine-X-threonine (N X T), where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antigen binding protein is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the protein amino acid sequence is preferably altered through changes at the DNA level, particularly by mutating the DNA encoding the target polypeptide at preselected bases such that codons are generated that will translate into the desired amino acids.

Accordingly, N-linked glycosylation sites may be adding by altering a codon for a single amino acid. For example, codons encoding N-X-z (where z is any amino acid) can be altered to encode N-X-T (or N-X-S), or codons encoding y-X-T/S can be altered to encode N-X-T/S. Alternatively, codons encoding two amino acids can be simultaneously changed to introduce an N-linked glycosylation site (for example, codons for y-X-z can be altered to encode N-X-T/S). In this manner, from one to ten N-linked glycosylation sites can be inserted.

In addition to inserting N-linked glycosylation sites into TIMP-3, any glycosylation sites that are present in native TIMP-3 can be modified, for example in an effort to stabilize the structure of the molecule. Thus, for example, the A at residue 208 may be substituted with a different residue, such as Y, V, or G. Additional modifications at the 'N—X-T' site at residues 206-208 include substituting F for I at residue 205, or Y for I at residue 205, in combination with one of the aforementioned substitutions at residue 208.

In another embodiment, regions sensitive or susceptible to proteolytic cleavage are identified and mutated. In another aspect of the invention, there are provided TIMP-3 muteins or variants that exhibit decreased interaction with the scavenger receptor LRP-1. In one embodiment, such muteins are made by identifying and mutating Lysine residues that are hypothesized to be important in the interaction between TIMP-3 and LRP-1.

Moreover, it is recognized that a TIMP-3 mutein or variant may exhibit more than one of these properties (for example, an inserted glycosylation site may decrease the need for heparin in the cell culture medium, decrease the interaction with LRP-1 and increase resistance to proteolysis). Additional embodiments include TIMP-3 muteins or variants having more than one mutation, such that a combination of mutations results in more than one of the aforementioned properties or effects.

Desirable TIMP-3 muteins can be identified in several ways. In a first method, in silico analysis is used to facilitate charge rebalancing between TIMP-3 and the related metalloproteinase inhibitor, TIMP-2 (the latter has been observed to exhibit a good mammalian expression profile). In one embodiment of the present invention, TIMP-3 surface exposed positively charged patches are redistributed to mimic the TIMP-2 charged surface. In another embodiment, charge differences between TIMP-2 and TIMP-3 are masked by the insertion of glycosylation sites. Glycosylation insertion may also be useful for expression improvement (see, for example, Enhancing the Secretion of Recombinant Proteins by Engineering N-Glycosylation Sites. Liu Y. et al, Amer Inst Chem Eng 2009, pg. 1468).

Thus, in another embodiment, a sub-set of solvent exposed sites developed by computational analysis are screened for N-glycosylation likelihood. For methods involving insertion of glycosylation sites, an N-glycosylation prediction tool is useful in selecting sites that may be mutated to facilitate potential N-linked glycosylation, for example by identifying residues that could be mutated to form a canonical N-x-T glycosylation site (where N is asparagine, x is any amino acid and T is threonine). In a further embodiment, structure based methods are used to identify all solvent exposed amino acids (including those amino acids with sidechain exposure >20 $Å^2$). An additional embodiment includes the mutation of LRP1 interacting lysines on TIMP-3, based upon the crystal structure of LRP1/RAP (Receptor Associated Protein) with interacting RAP lysines mapped against TIMP-3.

Additional combinations are contemplated herein. For example, an F57N mutation can be made in combination with a mutation at a lysine residue, wherein the lysine residue is any lysine in TIMP-3. In one embodiment, a single lysine is mutated; in another embodiment, two, three, four or five lysine residues are mutated. In certain embodiments, lysine residues at amino acid 45 and/or 133 can be mutated. In another example, an F57N mutation introduces a single N-linked glycosylation site; this mutation can be made with additional mutations to introduce additional glycosylation sites, or with other mutations designed to affect one or more of the aforementioned properties of TIMP-3. Contemplated herein are TIMP-3 muteins, or variants, that comprise one introduced N-linked glycosylation site, that comprise two, three or four N-linked glycosylation sites, and that comprise five or more N-linked glycosylation sites.

Particular mutations are shown in FIGS. 1 and 2. FIG. 1 presents an alignment of native, full-length human TIMP-3 and a mutated form of full-length human TIMP-3 in which the letter "X" has been substituted for particular amino acids within the sequence. The signal sequence is underlined; other signal sequences can be substituted therefore, as described herein. Certain substitutions are envisioned in the mature form of TIMP-3, and are designated herein as "n # m" where "n" designates the amino acid found in the native, full-length TIMP-3, "#" designates the amino acid residue number, and "m" designates the amino acid that has been substituted. Thus, for example, "K45N" indicates that the lysine (K) at amino acid 45 has been substituted with asparagine (N). The mutated forms of human TIMP-3 exemplified herein comprise the following mutations (alone, or in combination): K45N; K45S; V47T; K50N; V52T; P56N; F57N; G58T; T63E; T63N; K65T; T74E; H78E; H78E; H78N; Q80T; K94N; E96T; D110N; K112T; Q126N; R138T; and G173T. Combinations of these mutations are also contemplated, and can include from two to ten (i.e., 2, 3, 4, 5, 6, 7 8, 9 or 10) of the aforementioned substitutions.

Specific combinations of mutations include K45E, K49S; K45E, K49E; K45E, T63E; K45E, Q80E; K45E, T63E, H78E; T63E, H78E, Q80E; K45E, T63E, H78E, Q80E; L51T, T74E, H78D; T74E, H78E, Q80E; T74E, H78D, Q80E; K45N, V47T; K49N, L51T; K75N, P77T; K45E, K49N, L51T, T63E; E96N, N98T; V97N,K99T; R138N, H140T; T158N,K160T; T166N, M168T; H181N, A183T; R186N,K188T; P201N,K203T; A208Y; A208V; T63E, T74E, H78E; T63E, T74E, H78D; K65N, M67T; K45N, V47T, T63E, T74E, H78E; K49N, L51T, T63E, T74E, H78E; K49N, L51T, T74E, H78E; K49N,L51T; K50N, V52T; L51N, K53T; T63N, K65T; H78N, Q80T; K94N, E96T; D110N, K112T; Q126N; R138T; G173T; F57N; P56N,G58T; P56N,G58T; T63N, K65T; K45S, F57N; K49S, F57N; K68S, F57N; K133S, F57N; K45S, K133S, F57N; and K49S, K68S, F57N.

Additional combinations include K45S, F57N, D110N, K112T; K45S, F57N, H78N, Q80T, D110N, K112T; K45S, F57N, H78N, Q80T, D110N, K112T, Q126N; K45S, F57N, H78N, Q80T, K94N, E96T Q126N; K45S, F57N, H78N, Q80T, Q126N, G173T; K45S, F57N, T63N, K65T; K45S, F57N, T63N, K65T, K94N, E96T; K45S, F57N, T63N, K65T, K94N, E96T, G173T; K45S, F57N, T63N, K65T, R138T, G173T; K45N, V47T, F57N, T63N, K65T, R138T, G173T; K45S, F57N, T63N, K65T, K94N, E96T, R138T; K45N, V47T, F57N, T63N, K65T, K94N, E96T, R138T; K45S, F57N, Q126N, R138T, G173T; P56N, G58T, T63N, K65T, K94N, E96T, Q126N, G173T; P56N, G58T, T63N, K65T, D110N, K112T, Q126N, G173T; and K45S, F57N, Q126N, R138T, G173T.

Further mutations include K49S, K50N/V52T, K53E, V97N/K99T, R186N/K188T; K50N/V52T, V97N/K99T, R186N/K188T; K49E, K53E, K188Q; K50N/V52T, R186N/K188T; K50N/V52T, F57N, R186N/K188T; K45S, K50N/V52T, F57N, R186N/K188T; K50N/V52T, F57N, T63N/K65T, R186N/K188T; K45S, K50N/V52T, F57N R186N/K188T; K45S, K49S, K50N/V52T, F57N R186N/K188T; K49S, K50N/V52T, F57N, V97N/K99T, R186N/K188T; and K45S, K50N/V52T, F57N, V97N/K99T, R186N/K188T.

FIG. 2 presents an alignment of native, full-length human TIMP-3, and a TIMP-3 variant in which certain amino acid substitutions have been made that render the sequence more similar to that of TIMP-2. The signal sequence is present and underlined for the native, full-length TIMP-3 sequence to maintain consistency of numbering; other signal sequences can be substituted therefore, as described herein. In the sequence for the TIMP-3 variant, "X" has been substituted for particular amino acids to indicate residues in the mature form of TIMP-3 at which substitutions are envisioned; These substitutions include H, K, P, R, S or W at residue 25; A at residue 27; D, L or S at residue 28; N at residue 32; T at residue 39; T, F, A or N at residue 43; I or T at residue 45; D at residue 46; S at residue 48; S at residue 49; T at residue 51; N at residue 63; N at residue 67; I at residue 68; D or W at residue 78; T at residue 96; N at residue 202 and S at residue 207. The substitutions can be made individually, or in combination. Thus, using the formatting described for FIG. 1, one variant exemplified in FIG. 2 is A27T, I68K. Additional combinations are also contemplated, and can include from two to ten of the aforementioned substitutions. Moreover, the substitutions described in FIG. 2 can be combined with the substitutions described in FIG. 1, for example, A27T, P56N, G58T.

Lee et al. (J. Biol. Chem. 282:6887; 2007) disclose studies that purported to identify extracellular matrix binding motifs in TIMP-3. When they failed to identify known heparin binding sequences in TIMP-3, they identified eleven lysine and arginine residues, the location of which suggested that the side chains of these basic amino acids would be exposed at the surface of TIMP-3 in considerable high density. These residues were K26, K27, K30, K71, K76, R100, K123, K125, K137, R163, K165 (using the numbering system used herein, these residues would be numbered K49, K50, K53, K94, K99, R123, K146, K148, K160, R186, K188). Accordingly, additional TIMP-3 muteins include those shown below. These muteins are expected to exhibit partial or full heparin independence. In additional to modification of surface-exposed basic amino acid sidechains. Certain of the mutations will also introduce an N-liked glycosylation site into the TIMP-3 mutein (i.e., K94N/E96T).

Among muteins that are made to reduce heparin independence are K49E, K50E, K53E, K99E, R186Q, K188Q; K49E, K50E, K53E, F57N, K99E, R186Q, K188Q; K45S, K50E, K53E, F57N, K99E, R186Q, K188Q; K49S, K50N/V52T, K99E, K188Q; K50N/V52T, K99E, K188Q; K50N/V52T, K94N/E96T, K188Q; K50N/V52T, K94N/E96T, G173T; K50N/V52T, R186N/K188T; K50N/V52T, K94N/E96T, R186N,K188T; K50N/V52T, F57N, K94N/E96T, R186N/K188T; K45S, K50N/V52T, F57N, K94N/E96T, R186N/K188T; K50N/V52T, T63N/K65T, K94N/E96T, R186N/K188T; K45S, K50N/V52T, T63N/K65T, K94N/E96T, R186N/K188T. In accordance with the present invention, several of these muteins may exhibit multiple favorable properties. For example, several of the muteins contain inserted N-linked glycosylation sites; other muteins comprises mutations that enhance expression in mammalian cell system.

The TIMP-3 variants, muteins or derivative will have an amino acid sequence that is quite similar to that of native TIMP-3. In one embodiment, a TIMP-3 variant, mutein or derivative will be at least 85% identical to native TIMP-3; in another embodiment, a TIMP-3 variant, mutein or derivative will be at least 90% identical to native TIMP-3; in another embodiment, a TIMP-3 variant, mutein or derivative will be at least 95% identical to native TIMP-3. In further embodiments, a TIMP-3 variant, mutein or derivative is at least 96% identical, 97% identical, 98% identical or 99% identical to native TIMP-3. As used herein, the percent identities refer to a comparison of the mature, full-length variant, mutein or derivative to the mature, full-length form of native TIMP-3, i.e., TIMP-3 lacking a signal peptide (amino acids 24 through 211 of TIMP-3). Those of skill in the art will readily understand that a similar comparison can be made between a variant, mutein or derivative of the N-terminal domain of TIMP-3 and the N-terminal domain of native TIMP-3.

Similarity can also be expressed by the number of amino acids that differ between a mutein or variant and a native TIMP-3. For example, a TIMP-3 variant or mutein can vary from native TIMP-3 by one amino acid, two amino acids, three amino acids, four amino acids, five amino acids, six amino acids, seven amino acids, eight amino acids, nine amino acids, or ten amino acids. A variant or mutein that differs from native TIMP-3 at ten amino acids will be about 95% identical to native TIMP-3. In further embodiments, a TIMP-3 variant or mutein differs from native mature TIMP-3 at 11, 12, 13, 14, 15, 16, 17, 18, 19 or 20 amino acids Additional changes can be made in a nucleic acid encoding a TIMP-3 polypeptide (either native, mutein, variant or derivative) to facilitate expression. For example, the signal peptide of native TIMP-3 can be substituted with a different signal peptide.

Other derivatives of TIMP-3 polypeptides within the scope of this invention include covalent or aggregative conjugates of TIMP-3 polypeptides, or fragments thereof, with other proteins or polypeptides, such as by expression of recombinant fusion proteins comprising heterologous polypeptides fused to the N-terminus or C-terminus of a TIMP-3 polypeptides. For example, the conjugated peptide may be a heterologous signal (or leader) peptide, e.g., the yeast alpha-factor leader, or a peptide such as an epitope tag. Those of ordinary skill in the art understand that a heterologous signal peptide may differ in length from the native TIMP-3 signal peptide, but can correctly identify the location of muteins with respect to the amino acid sequence of mature TIMP-3 by aligning the N-terminal cysteine residues of TIMP-3 polypeptides produced using a heterologous signal peptide.

TIMP-3 polypeptide-containing fusion proteins can comprise peptides added to facilitate purification or identification of the TIMP-3 polypeptide (e.g., poly-His). Another tag peptide is the FLAG® peptide described in Hopp et al., *Bio/Technology* 6:1204, 1988, and U.S. Pat. No. 5,011,912. The FLAG® peptide is highly antigenic and provides an epitope reversibly bound by a specific monoclonal antibody (mAb), enabling rapid assay and facile purification of expressed recombinant protein. Reagents useful for preparing fusion proteins in which the FLAG® peptide is fused to a given polypeptide are commercially available (Sigma, St. Louis, Mo.).

Covalent modifications are also considered derivatives of the TIMP-3 polypeptides and are included within the scope of this invention, and are generally, but not always, done post-translationally. For example, several types of covalent modifications of the antigen binding protein are introduced into the molecule by reacting specific amino acid residues of the antigen binding protein with an organic derivatizing agent that is capable of reacting with selected side chains or the N- or C-terminal residues.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Accordingly, in one aspect of the invention, cysteinyl residues are added to the native TIMP-3 sequence, for example by altering selected codon(s) to encode Cys. Such Cys substitution can be made in regions of TIMP-3 that are shown to be important for expression, folding or other properties as shown herein.

The number of carbohydrate moieties on the proteins of the invention can be increased by chemical or enzymatic coupling of glycosides to the protein. These procedures are advantageous in that they do not require production of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, 1981, *CRC Crit. Rev. Biochem.*, pp. 259-306.

Removal of carbohydrate moieties present on the starting recombinant protein may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo- and exo-glycosidases as described by Thotakura et al., 1987, *Meth. Enzymol.* 138:350. Glycosylation at potential glycosylation sites may be prevented by the use of the compound tunicamycin as described by Duskin et al., 1982, *J. Biol. Chem.* 257:3105. Tunicamycin blocks the formation of protein-N-glycoside linkages.

Another type of covalent modification of the antigen binding protein comprises linking the protein to various nonproteinaceous polymers, including, but not limited to, various polyols such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the protein to facilitate the addition of polymers such as PEG.

Expression of TIMP-3 Polypeptides

Any expression system known in the art can be used to make the recombinant polypeptides of the invention. In general, host cells are transformed with a recombinant expression vector that comprises DNA encoding a desired TIMP-3 polypeptide (including TIMP-3 muteins or variants). Among the host cells that may be employed are prokaryotes, yeast or higher eukaryotic cells. Prokaryotes include gram negative or gram positive organisms, for example *E. coli* or *bacilli*. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, New York, 1985).

Mammalian cell expression can provide advantages for the production of TIMP-3 polypeptides, in facilitating folding and adoption of conformation that closely resembles that of native TIMP-3. Numerous mammalian cell expression systems are known in the art, and/or are commercially available; the latter includes systems such as Gibco®Freedom® CHO-S® (a product designed for ease of use with all aspects of cloning and expression of recombinant proteins in Chinese Hamster Ovary (CHO)-derived suspension culture; ProBioGen, Life Technologies; Carlsbad, Calif.), GS Gene Expression System® (a transfection system designed to provide development of high-yielding, stable, cGMP-compatible mammalian cell lines; Lonza Biologics, Slough, UK), PER.C6® technology (a package of tools designed to facilitate the large-scale production of recombinant proteins, utilizing a continuously dividing set of cells derived from a single, immortalized human cell; Crucell, Leiden, The Netherlands), or immortalized amniocyte cells such as CAP and CAP-T (human cell-based expression systems for the expression and production of complex proteins; Cevec, Cologne, Germany).

Additional cell expression systems include systems such as the Selexis SUREtechnology Platform™ (a technology platform that can be applied to a variety of cell lines to facilitate development cell lines for the production of recombinant proteins; Selexis Inc., Switzerland); ProFection® Mammalian Transfection Systems (a transfection system that provides high-efficiency transfections of cells for the production of recombinant proteins; Promega, Madison Wis.); the Expi293™ Expression System (a high-density mammalian transient protein expression system, Life Technologies, Grand Island, N.Y.); and MaxCyte® VLX™ and STX™ Transient Transfection Systems (a scalable transfection system for use in the production of recombinant proteins, including antibodies; MaxCyte, Gaithersburg, Md. Those of skill in the art are further aware of other expression systems, such as techniques originally described by Wigler et al. (Cell 1979:777) and additional techniques that are described, for example, by the National Research Council of Canada on their website.

Various vessels are known in the art to be suitable for the culture of transformed cells and production of recombinant proteins. These include 24-deep well plates, 250 ml and 1 L shakeflasks; and various bioreactors of various sizes, for example, 2 L, 5 L, 10 L, 30 L, 100 L, 1000 L, 10000 L and larger Bioreactors. Other suitable vessels for cell culture are know in the art and can also be used as described herein.

Cell culture media formulations are well known in the art; typically, a culture medium provides essential and non-essential amino acids, vitamins, energy sources, lipids, and trace elements required by the cell for minimal growth and/or survival, as well as buffers, and salts. A culture medium may also contain supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source; as described herein, cell-cycle inhibitors can be added to a culture medium. In certain embodiments, a medium is advantageously formulated to a pH and salt concentration optimal for cell survival and proliferation. In certain embodiments, the medium is a feed medium that is added after the beginning of the cell culture. In certain embodiments, the cell culture medium is a mixture of a starting nutrient solution and any feed medium that is added after the beginning of the cell culture.

Various tissue culture media, including defined culture media, are commercially available, for example, any one or a combination of the following cell culture media can be used: RPMI-1640 Medium, RPMI-1641 Medium, Dulbecco's Modified Eagle's Medium (DMEM), Minimum Essential Medium Eagle, F-12K Medium, Ham's F12 Medium, Iscove's Modified Dulbecco's Medium, McCoy's 5A Medium, Leibovitz's L-15 Medium, and serum-free media such as EX-CELL™ 300 Series (JRH Biosciences, Lenexa, Kans.), among others. Serum-free versions of such culture media are also available. Cell culture media may be supplemented with additional or increased concentrations of components such as amino acids, salts, sugars, vitamins, hormones, growth factors, buffers, antibiotics, lipids, trace elements and the like, depending on the requirements of the cells to be cultured and/or the desired cell culture parameters.

The transformed cells can be cultured under conditions that promote expression of the polypeptide, and the polypeptide recovered by conventional protein purification procedures. One such purification procedure includes the use of affinity chromatography as well as other methods that are known in the art. One method to isolate TIMP-3 parent or TIMP-3 muteins from mammalian supernatants is to utilize a TIMP-3 that is fused to a carboxy-terminal 6×-Histidine tag in combination a 6×-Histidine affinity Ni-Sepharose resin (for example, Immobilized Metal Affinity Chromatography (IMAC); general procedures are known in the art, and reagents for, and examples of such procedures are outlined by QIAGEN, Germantown, Md. and GE Healthcare, Pittsburg, Pa.). Cation exchange chromatography (eg SP-HP Sepharose®, GE Healthcare) can be utilized to further isolate TIMP-3 post IMAC elution, or as an alternative strategy without the use of IMAC to capture TIMP-3 from mammalian supernatants (elution of TIMP-3 and muteins thereof occurs with the use of a sodium chloride gradient at neutral pH). Size Exclusion Chromatography (eg. Superdex 200®, GE Healthcare, (mobile phase example: 10 mM $Na_2HPO_4$, 1.8 mM KH2PO4, 137 mM NaCl, 2.7 mM KCl),) is a general strategy that can be used to further isolate TIMP-3 or muteins thereof (in combination with an IMAC process or ion exchange chromatography. These and other methods are known in the art; see for example, Protein Purification: Principles: High Resolution Methods, and Applications, Third Edition (2012, John Wiley and Sons; Hoboken, N.J.).

The amount of polypeptide (native TIMP-3 or a TIMP-3 mutein or variant) can be determined by any suitable, quantitative or semi-quantitative method that will allow analysis of the amount of recombinant TIMP-3 (native, variant or mutein) in cell culture supernatant fluid, i.e., conditioned media (CM). Suitable qualitative or semi-quantitative methods include Western Blot and Coomassie stained SDS PAGE gels. Quantitative measurements could include use of an enzyme immunoassay such as a human TIMP-3 ELISA (R&D Systems Inc., Minneapolis, Minn.), or ForteBio Octet® (Pall ForteBio Corp, Menlo Park, Calif.) with antibody mediated capture of TIMP-3, or direct UV (ultraviolet) absorbance (280 nm) measurements on purified TIMP-3.

Thus, the effects of a particular mutation in TIMP-3 can be evaluated by comparing the amount of recombinant mutein made to the amount of native protein made under similar culture conditions. A TIMP-3 mutein or variant can be expressed at levels that are 1×, 2×, 3×, 4×, 5×, 10× or greater, levels as observed for native TIMP-3. If desired, the specific productivity of a particular transformed or transfected cell line can be determined to allow comparison or the specific productivity for various forms of TIMP-3. Specific productivity, or qP, is expressed in picograms of recombinant protein per cell per day (pg/c/d), and can be readily determined by applying methods known in the art to quantitated the cells in a culture and the above-mentioned methods of quantifying recombinant protein.

Uses for TIMP-3 Polypeptides

TIMP-3 polypeptides, variants, muteins or derivatives can be used, for example, in assays, or they can be employed in treating any condition in which a greater level of TIMP-3 activity is desired (i.e., conditions in which matrix metalloproteases (MMPs) and/or other proteinases that are inhibited or inhibitable by TIMP-3 play a causative or exacerbating role), including but not limited to inflammatory conditions, osteoarthritis, and other conditions in which excessive or inappropriate MMP activity occurs (for example, myocardial ischemia, reperfusion injury, and during the progression to congestive heart failure). Inflammatory conditions include asthma, chronic obstructive pulmonary disease (COPD), and idiopathic pulmonary fibrosis (IPF), inflammatory bowel disease (for example, ulcerative colitis, Crohn's disease, and celiac disease), psoriases, myocarditis including viral myocarditis, inflammation related to atherosclerosis, and arthritic conditions including rheumatoid arthritis, psoriatic arthritis, and the like.

The TIMP-3 polypeptide, variant mutein or derivative compositions described herein modify the pathogenesis and provide a beneficial therapy for diseases or conditions characterized by matrix degradation and/or inflammation, i.e., those in which metalloproteinases play a deleterious role. The compositions may be used alone or in conjunction with one or more agents used in treating such conditions. Accordingly, the present TIMP-3 polypeptide, variant mutein or derivative compositions may be useful in the treatment of any disorder where excessive matrix loss is caused by metalloproteinase activity. The inventive TIMP-3 variant mutein or derivative compositions are useful, alone or in combination with other drugs, in the treatment of various disorders linked to the overproduction of collagenase, aggrecanase, or other matrix-degrading or inflammation-promoting enzyme(s), including dystrophic epidermolysis bullosa, osteoarthritis, Reiter's syndrome, pseudogout, rheumatoid arthritis including juvenile rheumatoid arthritis, ankylosing spondylitis, scleroderma, periodontal disease, ulceration including corneal, epidermal, or gastric ulceration, wound healing after surgery, and restenosis. Other pathological conditions in which excessive collagen and/or proteoglycan degradation may play a role and thus where TIMP-3 polypeptide, variant mutein or derivative compositions can be applied, include emphysema, Paget's disease of bone, osteoporosis, scleroderma, pressure atrophy of bone or tissues as in bedsores, cholesteatoma, and abnormal wound healing. Additional conditions that are, directly or indirectly, a result of decreased amounts of TIMP-3 or increased amounts of metalloproteases (for example, in myocardial ischemia, reperfusion injury, and during the progression to congestive heart failure) may also be treated with the presently described compositions, either alone or in conjunction with other drugs commonly used to treat individuals afflicted with such conditions. TIMP-3 polypeptide, variant, mutein or derivative compositions can additionally be applied as an adjunct to other wound healing promoters, e.g., to modulate the turnover of collagen during the healing process.

Many metalloproteinases also exhibit pro-inflammatory activity; accordingly, additional embodiments include methods of treating inflammation and/or autoimmune disorders, wherein the disorders include, but are not limited to, cartilage inflammation, and/or bone degradation, arthritis, rheumatoid arthritis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, polymyalgia rheumatica, sarcoidosis, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease, ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis, pancreatitis, insulin-dependent diabetes mellitus, mastitis, cholecystitis, cholangitis, pericholangitis, multiple sclerosis (MS), asthma (including extrinsic and intrinsic asthma as well as related chronic inflammatory conditions, or hyperresponsiveness, of the airways), chronic obstructive pulmonary disease (COPD. i.e., chronic bronchitis, emphysema), Acute Respiratory Disorder Syndrome (ARDS), respiratory distress syndrome, cystic fibrosis, pulmonary hypertension, pulmonary vasoconstriction, acute lung injury, allergic bronchopulmonary aspergillosis, hypersensitivity pneumonia, eosinophilic pneumonia, bronchitis, allergic bronchitis bronchiectasis, tuberculosis, hypersensitivity pneumonitis, occupational asthma, asthma-like disorders, sarcoid, reactive airway disease (or dysfunction) syndrome, byssinosis, interstitial lung disease, hypereosinophilic syndrome, rhinitis, sinusitis, and parasitic lung disease, airway hyperresponsiveness associated with viral-induced conditions (for example, respiratory syncytial virus (RSV), parainfluenza virus (PIV), rhinovirus (RV) and adenovirus), Guillain-Barre disease, Graves' disease, Addison's disease, Raynaud's phenomenon, autoimmune hepatitis, GVHD, and the like. TIMP-3 polypeptides, variants, muteins or derivatives also have application in cases where decreased relative levels of TIMP-3 (i.e., a decrease in the ratio of endogenous TIMP-3 to metalloproteases, which may be a result of decreased amounts of TIMP-3 or increased amounts of metalloproteases) are associated with pathological effects, for example, in myocardial ischemia, reperfusion injury, and during the progression to congestive heart failure.

Based on the ability of TIMP-3 to inhibit connective tissue degradation, TIMP-3 polypeptides, variants, muteins or derivatives have application in cases where inhibition of angiogenesis is useful, e.g., in preventing or retarding tumor development, and the prevention of the invasion of parasites. For example, in the field of tumor invasion and metastasis, the metastatic potential of some particular tumors correlates with the increased ability to synthesize and secrete collagenases, and with the inability to synthesize and secrete significant amounts of a metalloproteinase inhibitor. The presently disclosed TIMP-3 proteins also have therapeutic application in inhibiting tumor cell dissemination during removal of primary tumors, during chemotherapy and radiation therapy, during harvesting of contaminated bone marrow, and during shunting of carcinomatous ascites. Diagnostically, correlation between absence of TIMP-3 production in a tumor specimen and its metastatic potential is useful as a prognostic indicator as well as an indicator for possible prevention therapy.

MMPs also act on the basal lamina and tight junction proteins in the brain, as part of the pathway for opening the blood-brain barrier (BBB), facilitating the entrance of cells and soluble mediators of inflammation into the brain. Accordingly, the present compositions and methods may be useful in the treatment of disorders of the nervous system characterized by excessive or inappropriate permeabilization of the BBB. Additionally, degradation of matrix proteins around neurons can result in loss of contact and cell death; thus, the disclosed TIMP-3 compositions may protect nerve cells from damage by preserving the basement membrane surrounding nerve cells. The inventive TIMP-3 compositions are useful in treating or ameliorating the neuroinflammatory response to injury, for example, cerebral ischemia, or for traumatic brain injury. The compositions disclosed herein will also be useful in the treatment of neurodegenerative diseases where inflammation is an underlying cause of the disease, for example, multiple sclerosis, as well as in treatment of various forms of neuropathy and/or myopathy, spinal cord injury, and amyotrophic lateral sclerosis (ALS). Accordingly, uses of the inventive compositions may involve co-administration with BDNF, NT-3, NGF, CNTF, NDF, SCF, or other nerve cell growth or proliferation modulation factors. In addition, the present compositions and methods may be applicable for cosmetic purposes, in that localized inhibition of connective tissue breakdown may alter the appearance of tissue.

TIMP-3 polypeptides, variants, muteins or derivatives may be employed in an in vitro procedure, or administered in vivo to augment endogenous TIMP-3 activity and/or enhance a TIMP-3-induced biological activity. The inventive TIMP-3 polypeptides, variants, muteins or derivative may be employed in vivo under circumstances in which endogenous TIMP-3 is downregulated or present at low levels. Disorders caused or exacerbated (directly or indirectly) by TIMP-3-inhibitable proteinases, examples of which are provided herein, thus may be treated. In one embodiment, the present invention provides a therapeutic method comprising in vivo administration of a TIMP-3 polypeptide, variant, mutein or derivative to a mammal in need thereof in an amount effective for increasing a TIMP-3-induced biological activity. In another embodiment, the present invention provides a therapeutic method comprising in vivo administration of a TIMP-3 polypeptide, variant, mutein or derivative to a mammal in need thereof in an amount effective for elevating endogenous levels of TIMP-3.

In another aspect, the present invention provides TIMP-3 polypeptides, variants, muteins or derivatives having improved half-life in vivo. In one embodiment, the half-life of a TIMP-3 mutein is at least twice that of native TIMP-3; in another embodiment, the half-life is at least three times, four times, five times, six times, eight times or ten times greater than that of native TIMP-3. In one embodiment, the half-life is determined in a non-human mammal; in another embodiment, the half-life is determined in a human subject. Further embodiments provide a TIMP-3 mutein or variant that has a half-life of at least one day in vivo (e.g., when administered to a human subject). In one embodiment, the TIMP-3 polypeptides, variants, muteins or derivatives have a half-life of at least three days. In another embodiment, the TIMP-3 polypeptides, variants, muteins or derivatives have a half-life of four days or longer. In another embodiment, the TIMP-3 polypeptides, variants, muteins or derivatives have a half-life of eight days or longer.

In another embodiment, the TIMP-3 polypeptide, variants, or muteins is derivatized or modified such that it has a longer half-life as compared to the underivatized or unmodified TIMP-3 binding protein. The derivatized polypeptide can comprise any molecule or substance that imparts a desired property to the polypeptide, such as increased half-life in a particular use. The derivatized polypeptide can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the polypeptide for a particular use (e.g., administration to a subject, such as a human subject, or other in vivo or in vitro uses).

In one such example, the polypeptide is derivatized with a ligand that specifically binds to articular cartilage tissues, for example as disclosed in WO2008063291 and/or Rothenfluh et al., Nature Materials 7:248 (2008). Examples of molecules that can be used to derivatize a polypeptide include albumin (e.g., human serum albumin) and polyethylene glycol (PEG). Albumin-linked and PEGylated derivatives of polypeptides can be prepared using techniques well known in the art. In one embodiment, the polypeptide is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols (US Pat. App. No. 20030195154).

Compositions

Also comprehended by the invention are pharmaceutical compositions comprising effective amounts of polypeptide products (i.e., TIMP-3 polypeptides, variants, muteins or derivatives) of the invention together with pharmaceutically acceptable diluents, preservatives, solubilizers, emulsifiers, adjuvants and/or carriers useful in TIMP-3 therapy (i.e., conditions in which increasing the endogenous levels of TIMP-3 or augmenting the activity of endogenous TIMP-3 are useful). Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); covalent attachment of polymers such as polyethylene glycol to the protein (as discussed supra, see, for example U.S. Pat. No. 4,179,337 hereby incorporated by reference); incorporation of the material into particulate preparations of polymeric compounds such as polylactic acid, polyglycolic acid, etc. or into liposomes. Such compositions will influence the physical state, stability, rate of in vivo release, and rate of in vivo clearance of TIMP-3 binding proteins. See, e.g., Remington's Pharmaceutical Sciences, 18th Ed. (1990, Mack Publishing Co., Easton, Pa. 18042) pages 1435-1712 which are herein incorporated by reference.

Generally, an effective amount of the present polypeptides will be determined by the age, weight and condition or severity of disease of the recipient. See, Remingtons Pharmaceutical Sciences, supra, at pages 697-773, herein incorporated by reference. Typically, a dosage of between about 0.001 g/kg body weight to about 1 g/kg body weight, may be used, but more or less, as a skilled practitioner will recognize, may be used. For local (i.e., non-systemic) applications, such as topical or intra-articular applications, the dosing may be between about 0.001 $g/cm^2$ to about 1 $g/cm^2$. Dosing may be one or more times daily, or less frequently, and may be in conjunction with other compositions as described herein. It should be noted that the present invention is not limited to the dosages recited herein.

As is understood in the pertinent field, pharmaceutical compositions comprising the molecules of the invention are administered to a subject in a manner appropriate to the indication. Pharmaceutical compositions may be administered by any suitable technique, including but not limited to parenterally, topically, locally or by inhalation. If injected, the pharmaceutical composition can be administered, for example, via intravenous, intramuscular, intralesional, intraperitoneal or subcutaneous routes, by bolus injection, or continuous infusion.

Localized administration, e.g. at a site of disease or injury is contemplated, as are transdermal delivery and sustained release from implants. Other alternatives include eyedrops; oral preparations including pills, syrups, lozenges or chewing gum; and topical preparations such as lotions, gels, sprays, and ointments. For example, localized administration to joints or the musculoskeletal systems includes periarticular, intra-articular, intrabursal, intracartilaginous, intrasynovial and intratendinous administration. Administration to the respiratory system includes intrapulmonary, intraplural, intrapulmonary, intratracheal, intrasinal and intrabronchial delivery, and can be facilitated, for example, by an inhaler or a nebulizer. Intrathecal delivery and other methods that are useful to introduce compositions into the brain and/or nervous system are also contemplated herein, for example, epidural, intradural or peridural, administration, as well as perineural, intracaudal, intracerebral, intracisternal, and intraspinal administration.

Further examples of local administration include delivery to tissue in conjunction with surgery or another medical procedure. For example, a pharmaceutical composition can be administered to heart tissue during surgery that is performed to treat or ameliorate cardiac symptoms, or during a procedure such as cardiac catheterization (for example, percutaneous coronary intervention). Delivery may be via intracoronary, intracardia, intramyocardial, and/or transendocardial route, for example, and may be guided by endocardial or electromechanical maps of the area of the heart to be injected, or by the use of other techniques, such as magnetic resonance imaging (MRI). Compositions can also be delivered via inclusion in a cardiac patch, or in the coating of a stent or other device useful in cardiac conditions.

In addition to eye drops, the use of ointments, creams or gels to administer the present compositions to the eye is also contemplated. Direct administration to the interior of the eye may be accomplished by periocular, conjunctival, intracorneal, subconjunctival, subtenons, retrobulbar, intraocular, and/or intravitreal injection or administration. These and other techniques are discussed, for example, in Gibaldi's Drug Delivery Systems in Pharmaceutical Care (2007, American Society of Health-System Pharmacists, Bethesda, Md.).

A plurality of agents act in concert in order to maintain the dynamic equilibrium of the extracellular matrix and tissues. In treatment of conditions where the equilibrium is skewed, one or more of the other agents may be used in conjunction with the present polypeptides. These other agents may be co-administered or administered in seriatim, or a combination thereof. Generally, these other agents may be selected from the list consisting of the metalloproteinases, serine proteases, inhibitors of matrix degrading enzymes, intracellular enzymes, cell adhesion modulators, and factors regulating the expression of extracellular matrix degrading proteinases and their inhibitors. While specific examples are listed below, one skilled in the art will recognize other agents performing equivalent functions, including additional agents, or other forms of the listed agents (such as those produced synthetically, via recombinant DNA techniques, and analogs and derivatives).

Other degradation inhibitors may also be used if increased or more specific prevention of extracellular matrix degradation is desired. Inhibitors may be selected from the group consisting of alpha$_2$ macroglobulin, pregnancy zone protein, ovostatin, alpha$_1$-proteinase inhibitor, alpha$_2$-antiplasmin, aprotinin, protease nexin-1, plasminogen activator inhibitor (PAI)-1, PAI-2, TIMP-1, and TIMP-2. Others may be used, as one skilled in the art will recognize.

Intracellular enzymes may also be used in conjunction with the present polypeptides. Intracellular enzymes also may affect extracellular matrix degradation, and include lysozomal enzymes, glycosidases and cathepsins.

Cell adhesion modulators may also be used in combination with the present polypeptides. For example, one may wish to modulate cell adhesion to the extracellular matrix prior to, during, or after inhibition of degradation of the extracellular matrix using the present polypeptides. Cells which have exhibited cell adhesion to the extracellular matrix include osteoclasts, macrophages, neutrophils, eosinophils, killer T cells and mast cells. Cell adhesion modulators include peptides containing an “RGD” motif or analog or mimetic antagonists or agonists.

Factors regulating expression of extracellular matrix degrading proteinases and their inhibitors include cytokines, such as IL-1 and TNF-alpha, TGF-beta, glucocorticoids, and retinoids. Other growth factors effecting cell proliferation and/or differentiation may also be used if the desired effect is to inhibit degradation of the extracellular matrix using the present polypeptides, in conjunction with such cellular effects. For example, during inflammation, one may desire the maintenance of the extracellular matrix (via inhibition of enzymatic activity) yet desire the production of neutrophils; therefore one may administer G-CSF. Other factors include erythropoietin, interleukin family members, SCF, M-CSF, IGF-I, IGF-II, EGF, FGF family members such as KGF, PDGF, and others. One may wish additionally the activity of interferons, such as interferon alpha’s, beta’s, gamma’s, or consensus interferon. Intracellular agents include G-proteins, protein kinase C and inositol phosphatases. The use of the present polypeptides may provide therapeutic benefit with one or more agents involved in inflammation therapy.

Cell trafficking agents may also be used. For example, inflammation involves the degradation of the extracellular matrix, and the movement, or trafficking of cells to the site of injury. Prevention of degradation of the extracellular matrix may prevent such cell trafficking. Use of the present polypeptides in conjunction with agonists or antagonists of cell trafficking-modulation agents may therefore be desired in treating inflammation. Cell trafficking-modulating agents may be selected from the list consisting of endothelial cell surface receptors (such as E-selectins and integrins); leukocyte cell surface receptors (L-selectins); chemokines and chemoattractants. For a review of compositions involved in inflammation, see Carlos et al., Immunol. Rev. 114: 5-28 (1990), which is herein incorporated by reference.

Moreover, compositions may include neu differentiation factor, “NDF,” and methods of treatment may include the administration of NDF before, simultaneously with, or after the administration of TIMP-3. NDF has been found to stimulate the production of TIMP-2, and the combination of NDF, TIMP-1, -2 and/or -3 may provide benefits in treating tumors.

Polypeptide products of the invention may be “labeled” by association with a detectable marker substance (e.g., radiolabeled with $^{125}$I, or labeled with a fluorophore such as AlexaFluor® [LifeTechnologies, Grand Island N.Y.]) to provide reagents useful in detection and quantification of TIMP-3 in solid tissue and fluid samples such as blood or urine. Nucleic acid products of the invention may also be labeled with detectable markers (such as radiolabels and non-isotopic labels such as biotin) and employed in hybridization processes to identify relevant genes, for example.

As described above, the present TIMP-3 polypeptide, variant mutein or derivative compositions have wide application in a variety of disorders. Thus, another embodiment contemplated herein is a kit including the present compositions and optionally one or more of the additional compositions described above for the treatment of a disorder involving the degradation of extracellular matrix. An additional embodiment is an article of manufacture comprising a packaging material and a pharmaceutical agent within said packaging material, wherein said pharmaceutical agent contains the present polypeptide(s), variant(s), mutein(s) or derivative(s) and wherein said packaging material comprises a label which indicates a therapeutic use for TIMP-3. In one embodiment, the pharmaceutical agent may be used for an indication selected from the group consisting of: cancer, inflammation, arthritis (including osteoarthritis and the like), dystrophic epidermolysis bullosa, periodontal disease, ulceration, emphysema, bone disorders, scleroderma, wound healing, erythrocyte deficiencies, cosmetic tissue reconstruction, fertilization or embryo implant modulation, and nerve cell disorders. This article of manufacture may optionally include other compositions or label descriptions of other compositions.

The following examples are provided for the purpose of illustrating specific embodiments or features of the instant invention and do not limit its scope.

EXAMPLE 1

This Example describes a method used to determine the effects, if any, of a mutations or mutations in TIMP-3 resulted on expression in a mammalian expression system. This Example describes a general vector and host cell system, numerous vector and host cell systems are known in the art, described herein, and are suitable for determination of the effects, if any, of particular mutations in a TIMP-3 sequence on the expression of recombinant protein.

In general, a TIMP-3-encoding DNA is ligated into an expression vector under conventional conditions (i.e., the TIMP-3 encoding DNA is operably linked to other sequences in the vector so as to be expressible), and suitable mammalian cells are transformed or transfected with the vector. The transformed or transfected cells are cultured under appropriate conditions, and the recombinant protein is expressed and the amount evaluated, either qualitatively/semi-quantitatively, for example by Western blot or SDS=PAGE, or more quantitatively using an assay such as an ELSA (R&D Systems, Minneapolis Minn.) or ForteBio Octet® (Pall ForteBio Corp, Menlo Park, Calif.) In this manner, the effects of various mutations on the ability of mammalian cells to express a TIMP-3 protein, mutein or variant can be determined.

If the mutation or mutations were made to introduce N-linked glycosylation sites into a TIMP-3 polypeptide, or to enhance the native glycosylation site, it may be desirable to evaluate the presence and/or degree of glycosylation. Cells are transformed or transfected as described previously and semi-quantitative measures (eg. western blots) can be used to determine if N-linked glycosylation was not successfully incorporated, partially incorporated, or fully incorporated.

EXAMPLE 2

This Example describes a method used to determine whether a mutations or mutations in TIMP-3 resulted in increased heparin independence. Cells are transformed or transfected as described previously, and cultured in the presence or absence of heparin. The heparin can be added in varying amounts, to develop a semi-quantitative notion of the degree of heparin dependence. The amounts of TIMP-3 protein, mutein or variant expressed under various conditions is then determined, and a comparison is made to determine whether a particular mutation has any effect on whether or not heparin is required for release of the TIMP-3 protein, mutein or variant from the extracellular matrix, or whether the amount or heparin required is reduced.

EXAMPLE 3

This Example describes MMP Inhibition Assays in which MMP activity is measured by using fluorimetric methods; other methods are known in the art. For example, fluorescence signal is increased upon cleaving a quenched MMP subtype 5-FAM/QXL 520 fluorescence resonance energy transfer (FRET) peptide substrate by an activated MMP subtype or subtype specific catalytic domain. FRET peptides are available for a number of different MMP, for example, from Anaspec, Fremont, Calif. The TIMP-3 proteins used herein may be either nativeTIMP-3 or TIMP-3 mutein, variant or derivative; the proteins to be tested are referred to as test molecules.

For MMP2 activity assay, human pro-MMP2 (Anaspec, Fremont, Calif.) is activated with 1 mM 4-aminophenylmercuric acetate (APMA, Anaspec, Fremont, Calif.) for 1 hour at 37° C. before incubating with MMP2 sensitive 5-FAM/QXL 520 FRET peptide in assay buffer provided by the vendor against various concentrations of test molecules in a black 384-well Optiplate (PerkinElmer, Waltham, Mass.) at 37° C. After 2 hours of incubation, fluorescence signal from the reaction plate is measured at excitation (490 nm) and emission (520 nm) on EnVision multilabel microplate reader (PerkinElmer, Waltham, Mass.). Data in relative fluorescence unit (RFU) is plotted against tested test molecule concentrations in GraphPad Prism 5.0 (GraphPad, San Diego, Calif.) to estimate half maximal inhibition constant (IC50).

For MMP9 activity measurement, a catalytic domain of human MMP9 (Anaspec, Fremont, Calif.) is incubated with MMP9 sensitive 5-FAM/QXL 520 FRET peptide and various concentrations of test molecules in a black 384-well Optiplate (PerkinElmer, Waltham, Mass.) at 37° C. After 2 hours of incubation, fluorescence signal is measured at excitation (490 nm) and emission (520 nm) on EnVision multilabel microplate reader (PerkinElmer, Waltham, Mass.). Data in relative fluorescence unit (RFU) is plotted against tested test molecule concentrations in GraphPad Prism 5.0 (GraphPad, San Diego, Calif.) to estimate half maximal inhibition constant (IC50).

For MMP13 activity, test molecules are titrated in assay buffer (20 mM Tris, 10 mM $CaCl_2$, 10 uM $ZnCl_2$, 0.01% Brij 35 (Calbiochem/EMD, San Diego, Calif.), pH 7.5) and added to black polystyrene 96 or 384 well assay plate (Griener Bio-One, Germany). Active MMP13 (Calbiochem/EMD) is diluted in assay buffer and added to the test molecule titration and incubated for 10 minutes at room temperature in a final volume of 50 microL. Alternatively, pro-MMP-13 (R & D Systems, Minneapolis, Minn.) is activated with APMA for 2 hours at 37 degrees C., and used in the assay. A fluorogenic substrate such as Mca-PLGL-Dpa-AR-NH2 Fluorogenic MMP Substrate or Mca-KPLGL-Dpa-AR-NH2 Fluorogenic Peptide Substrate (R & D Systems) is prepared, and added to the MMP-13 enzyme/huTIMP-3/test molecule solution. MMP-13 activity is measured kinetically, for example for 20 minutes using Molecular Devices fluorescent plate reader (or equivalent).

The effect of the molecules being tested may be expressed as percent of expected maximum TIMP-3 inhibition of MMP enzymatic activity. Alternatively, a quantitative evaluation of MMP inhibitory activity may not be necessary; rather, individual test molecules can be evaluated as to whether they inhibit MMP or not. Those of ordinary skill in the art recognize that the parameters outlined herein can be varied by the application of routine experimentation. For example, preliminary experiments are performed using previously tested TIMP-3 and other materials to determine an appropriate concentration of an MMP or pro-MPP. Similarly, the type and appropriate concentration of substrate can also be determined. Thus, for example, MMP can be titrated and compared to a previously tested batch of MMP to optimize the assay parameters. Additionally, those of ordinary skill in the art can utilize similar assays to evaluate the effects, if any, or various TIMP-3 mutations on ability to of a TIMP-3 mutein or variant to inhibit other MMPs.

EXAMPLE 4

Using standard techniques of molecular biology, nucleic acids encoding numerous muteins of TIMP-3 were prepared and expressed in mammalian cells, substantially as described previously. The effects of the mutations on the expression of the encoded TIMP-3 muteins were evaluated. The listing of mutations made includes: G115T, N118D; K45E, K49S; K45E, K49E; K45E, T63E; K45E, Q80E; T63E, H78E; K45E, T63E, H78E; T63E, H78E, Q80E; K45E, T63E, H78E, Q80E; T63E, H78D; T63E, T74E, H78E; T63E, T74E, H78D; L51T, T74E, H78D; T74E, H78E, Q80E; T74E, H78D, Q80E; R43T, T74E, H78D, Q80E; R43E, T74E, H78D, Q80E; R43N, K45T; K45N, V47T; K49N, L51T; K65N, M67T; K75N, P77T; R43N, K45T, K49N, L51T; K45N, V47T, K49N, L51T; R43N, K45T, T63E, T74E, H78E; K45N, V47T, T63E, T74E, H78E; K49N, L51T, T63E, T74E, H78E; K45E, K49N, L51T, T63E; R43T, K49N, L51T, T74E, H78D; R43N, K45T, T74E, H78E; K49N, L51T, T74E, H78E; R43N, K45T, K49N, L51T, T74E, H78E; Q32N, A34T; S38D, D39T; R43N, K45T; V47N, K49T; K49N,L51T; K50N, V52T; L51N, K53T; F57N; P56N,G58T; T63N, K65T; P56N,G58T, T63N, K65T; M67N, M69T; H78N, Q80T; T84N, A86T; K94N, E96T; E96N, N98T; V97N,K99T; K99N,Q101T; T105N, R107T; D110N, K112T; E122N, W124T; R123N,D125T; Q126N; T128N; Q131N,K133T;

R132N G134T; R138N,H140T; R138T; H140N,G142T; K142T; K146N, K148T; T158N,K160T; T166N, M168T; M168N; G173T; HS179N, H181T; H181N, A183T; R186N, K188T; R196N,W198T; P200N,D202T; P201N,K203T; D202N; A208Y; A208V; K45S, F57N; K49S, F57N; K68S, F57N; K133S, F57N; K45S, K133S, F57N; and K49S, K68S, F57N.

Further evaluations of the muteins that expressed were performed, and are described below. Additional muteins are contemplated, including K49E, K50E, K53E, K99E, R186Q, K188Q; K49S, K50N/V52T, K53E, V97N/K99T, R186N/K188T; K50N/V52T, V97N/K99T, R186N/K188T; K49E, K53E, K188Q; K50N/V52T, R186N/K188T; K50N/V52T, F57N, R186N/K188T; K45S, K50N/V52T, F57N, R186N/K188T; K50N/V52T, F57N, T63N/K65T, R186N/K188T; K45S, K50N/V52T, F57N R186N/K188T; K45S, K49S, K50N/V52T, F57N R186N/K188T; K49S, K50N/V52T, F57N, V97N/K99T, R186N/K188T; K45S, K50N/V52T, F57N, V97N/K99T, R186N/K188T. These muteins can be made and tested as described herein.

EXAMPLE 5

This Table summarizes expression and MMP inhibition results obtained with numerous TIMP-3 muteins that did express in mammalian cells. For "Mammalian Expression vs. WT" the data are recorded as '+' indicating that expression was substantially the same as that of wild-type (or native) TIMP-3; '++' indicating that expression was increased 2-4 fold versus that observed with wild-type TIMP-3, and '+++' indicating that greater than 4-fold increase in expression versus wild-type TIMP-3. The designation '---' in the column referring to enzyme inhibition indicates that such testing was not done. The increase in the level of expression demonstrating the fold increase in expression as compared to that observed for wild-type TIMP-3 is determined either qualitatively through the use of western blots or SDS-PAGE Coomassie stained gels, or through the measurement of expression titers as measured using a ForteBio Octet® readout using an anti TIMP-3 antibody to capture TIMP-3 (such antibodies are publicly available, for example from EMD Millipore, Billerica, Mass.: AbCam®, Cambridge, Mass.:, or R&D Systems, Minneapolis, Minn.).

TABLE 1

| TIMP-3 Mutein (SEQ ID NO) | TIMP-3 Mutein Yield | Retains MMP2, 9 or 13 Inhibition |
|---|---|---|
| K45E, K49S; (SEQ ID NO: 5) | + | — |
| K45E, K49E; (SEQ ID NO: 6) | + | — |
| K45E, T63E; (SEQ ID NO: 7) | + | — |
| K45E, Q80E; (SEQ ID NO: 8) | + | — |
| K45E, T63E, H78E; (SEQ ID NO: 10) | + | — |
| T63E, H78E, Q80E; (SEQ ID NO: 11) | + | — |
| K45E, T63E, H78E, Q80E; (SEQ ID NO: 12) | + | — |
| T63E, T74E, H78E; (SEQ ID NO: 13) | ++ | Yes |
| T63E, T74E, H78D; (SEQ ID NO: 14) | ++ | — |
| L51T, T74E, H78D; (SEQ ID NO: 53) | + | — |
| T74E, H78E, Q80E; (SEQ ID NO: 16) | + | — |
| T74E, H78D, Q80E; (SEQ ID NO: 17) | + | — |
| K45N, V47T; (SEQ ID NO: 26) | + | — |
| K65N, M67T; (SEQ ID NO: 37) | ++ | — |
| K45N, V47T, T63E, T74E, H78E; (SEQ ID NO: 18) | ++ | Yes |
| K49N, L51T, T63E, T74E, H78E; (SEQ ID NO: 19) | ++ | — |
| K45E, K49N, L51T, T63E; (SEQ ID NO: 20) | + | — |
| K49N, L51T, T74E, H78E; (SEQ ID NO: 21) | ++ | — |
| K49N, L51T; (SEQ ID NO: 27) | ++ | — |

TABLE 1-continued

| TIMP-3 Mutein (SEQ ID NO) | TIMP-3 Mutein Yield | Retains MMP2, 9 or 13 Inhibition |
|---|---|---|
| K50N, V52T; (SEQ ID NO: 30) | ++ | Yes |
| L51N, K53T; (SEQ ID NO: 54) | ++ | — |
| F57N; (SEQ ID NO: 33) | +++ | Yes |
| P56N, G58T; (SEQ ID NO: 31) | +++ | Yes |
| T63N, K65T; (SEQ ID NO: 36) | ++ | Yes |
| P56N, G58T, T63N, K65T; (SEQ ID NO: 32) | +++ | Yes |
| K75N, P77T; (SEQ ID NO: 38) | ++ | — |
| H78N, Q80T; (SEQ ID NO: 39) | ++ | — |
| K94N, E96T; (SEQ ID NO: 40) | ++ | Yes |
| E96N, N98T; (SEQ ID NO: 41) | + | — |
| V97N, K99T; (SEQ ID NO: 42) | + | — |
| D110N, K112T; (SEQ ID NO: 43) | ++ | — |
| Q126N; (SEQ ID NO: 44) | ++ | — |
| R138N, H140T; (SEQ ID NO: 46) | + | — |
| R138T; (SEQ ID NO: 45) | ++ | Yes |
| T158N, K160T; (SEQ ID NO: 47) | + | — |
| T166N, M168T; (SEQ ID NO: 48) | + | — |
| G173T; (SEQ ID NO: 49) | ++ | Yes |
| H181N, A183T; (SEQ ID NO: 50) | + | — |
| R186N, K188T; (SEQ ID NO: 51) | + | — |
| P201N, K203T; (SEQ ID NO: 52) | + | — |
| A208Y; (SEQ ID NO: 55) | + | — |
| A208V; (SEQ ID NO: 56) | + | — |
| K45S, F57N; (SEQ ID NO: 23) | +++ | Yes |
| K49S, F57N; (SEQ ID NO: 28) | +++ | Yes |
| K68S, F57N; (SEQ ID NO: 34) | +++ | Yes |
| K133S, F57N; (SEQ ID NO: 35) | +++ | Yes |
| K45S, K133S, F57N; (SEQ ID NO: 24) | +++ | Yes |
| K49S, K68S, F57N (SEQ ID NO: 29). | +++ | Yes |

Certain of these mutations exhibited increased expression as compared to wild-type TIMP-3 in mammalian cells: T63E, T74E, H78E; T63E, T74E, H78D; K65N, M67T; K45N, V47T, T63E, T74E, H78E; K49N, L51T, T63E, T74E, H78E; K49N, L51T, T74E, H78E; K49N,L51T; K50N, V52T; L51N, K53T; T63N, K65T; K75N, P77T; H78N, Q80T; K94N, E96T; D110N, K112T; Q126N; R138T; G173T; F57N; P56N,G58T; P56N,G58T; T63N, K65T; K45S, F57N; K49S, F57N; K68S, F57N; K133S, F57N; K45S, K133S, F57N; and K49S, K68S, F57N. Of these, a subset (F57N; P56N,G58T; P56N,G58T; T63N, K65T; K45S, F57N; K49S, F57N; K68S, F57N; K133S, F57N; K45S, K133S, F57N; and K49S, K68S, F57N) expressed at levels that were fourfold or greater than that observed with wild-type TIMP-3.

A detailed comparison was performed on the MMP activity results for several of the muteins and wild-type TIMP-3 (WT); these results are shown below.

TABLE 2

| TIMP-3 Mutein | MMP2 IC50 (M) | MMP9 IC50 (M) | MMP13 IC50 (M) |
|---|---|---|---|
| WT | $0.6 \times 10^{-9}$ | $1.0 \times 10^{-9}$ | $0.9 \times 10^{-9}$ |
| F57N | $0.5 \times 10^{-9}$ | $4.6 \times 10^{-9}$ | $0.5 \times 10^{-9}$ |
| P56N,G58T | $1.0 \times 10^{-9}$ | $2.3 \times 10^{-9}$ | $3.1 \times 10^{-9}$ |
| T63N, K65T | $0.8 \times 10^{-9}$ | $0.5 \times 10^{-9}$ | $2.2 \times 10^{-9}$ |
| K45S, F57N | $0.3 \times 10^{-9}$ | $4.0 \times 10^{-9}$ | nd |

EXAMPLE 6

This Example describes an assay to evaluate the ability of a TIMP-3 protein to bind to HTB-94™ cells (a chondrocytic cell line available from the American Type Culture Collection, Manassas, Va.) by fluorescence activated cell sorter (FACS) analysis. HTB-94 cells are cultured in HTB-94 culture medium (high-glucose DMEM containing 10% fetal bovine serum [FBS] and 2 mM L Glutamine) at 37 C in 5% $CO_2$. Cells are seeded at a cell density of $2.5\times10^4$ cells/ml in standard tissue culture flasks for 6-12 weeks prior to staining and are passaged every 3-4 days after removal from flask via trypsinization. Approximately 16 hours prior to FACS stain, HTB-94 cells are seeded at 100,000 cells per well onto standard tissue culture 12-well plates in 2 ml volume HTB94 medium and incubated at 37 C in 5% $CO_2$. Cell are 80-90% confluent prior to stain.

After approximately 16 hours, the HTB94 culture medium is removed from the 12-well plates by aspiration and 1 ml 4 C stain buffer (phosphate buffered saline [PBS] 2% FBS 0.15% $NaN_3$) is applied per well. Cell plates are incubated 1 h on ice. Stain buffer is aspirated and TIMP-3 HIS-Myc tagged proteins (either native TIMP-3 or TIMP-3 variant) diluted in stain buffer to 80 microg/ml is added, 0.9 ml/well; the same volume of buffer only is added to a negative control well. Cell plates are incubated 30 min on ice, aspirated and washed twice with 1 ml/well stain buffer. After the second wash buffer is aspirated, and mouse anti-pentaHIS AlexaFluor488 conjugated antibody (Qiagen, Valencia, Calif.) diluted in stain buffer to 20 ug/ml is added, 0.9 mL/well. In parallel, irrelevant $mlgG_1$ AlexaFluor488 conjugated antibody (eBioscience, San Diego, Calif.) negative control stain reagent diluted in stain buffer to 20 microg/ml is added in parallel to a replicate well stained with known binder TIMP3 HIS-Myc (for example, K45S, F57N, SEQ ID NO:23).

Cell plates are incubated 30 min on ice while protected from light, aspirated and washed twice with 1 ml/well stain buffer. After the second wash buffer is aspirated, 1 mL per well cell-dissociation buffer (enzyme-free, PBS, catalog #13151-014; Life Technologies, Grand Island N.Y.,) is added. Cell plates are incubated 5 min at 37 C, and cells are transferred to 4 ml FACS tubes. Plate wells are rinsed with 1 ml well 25 C PBS and the rinses are added to corresponding FACS tubes containing cells in cell dissociation buffer. Tubes are centrifuged 5 min at 1000 RPM to form a cell pellet, and aspirated. Cells are resuspended in 300 microL 4% paraformaldehyde in PBS (PFA) and may be stored at 4 C protected from light until run on FACS.

Within two days of TIMP3 staining, 8000 fixed HTB94 cell events are acquired, for example on a Becton Dickinson FACS Calibur using FL1 for detecting AlexaFluor488 fluorescence. The forward scatter (FSC) detector's voltage is set at E00, and the side-scatter (SSC) detector's voltage is set at 316. Used in combination, these detectors measure light reflected off of cells as 'forward scatter' and 'side scatter,' which allows for the HTB-94 cell gate to be defined, also referred to as 'gated', and separated from non-cell material in the tube based on cell size and granularity. The FL1 detector's voltage is set at 370. Analysis is done, for example, using FlowJo vX.0.6.

Several TIMP-3 variants were analyzed for binding to HTB-94 cells in this manner; results for two different experiments are shown in Table 3 below (n.a.=not applicable; n.d.=not done). Nine TIMP3 HIS-Myc tagged glycovariants displayed no binding to HTB-94 cells in that no FL1 signal was detected over background for the method described. Results are shown in Table 3 below.

EXAMPLE 7

This Table summarizes expression and MMP inhibition results obtained with numerous TIMP-3 muteins that did express in mammalian cells.

TABLE 3

Expression and activity of TIMP-3 Muteins

| Hyperglycosylation variants | TIMP-3 Mutein Yield[1] | Retains MMP2, 9 or 13 Inhibition[2] | MMP2 Inhibition Shift[3] | MMP9 Inhibition Shift[3] |
|---|---|---|---|---|
| K45S, F57N, I205F, A208G (SEQ ID NO: 57) | ++ | nd | nd | nd |
| K45S, F57N, A208G (SEQ ID NO: 58) | ++ | nd | nd | nd |
| K45S, F57N, I205Y (SEQ ID NO: 59) | ++ | nd | nd | nd |
| K45S, F57N, I205Y, A208G (SEQ ID NO: 60) | ++ | nd | nd | nd |
| K45N,V47T,F57N,K75N,P77T,K94N,E96T,R138T,G173T (SEQ ID NO: 61) | + | Yes | 7 | 25 |
| K45N,V47T,F57N,K94N,E96T,R138T,G173T (SEQ ID NO: 62): | ++ | Yes | 5 | 15 |
| K45N,V47T,K50N,V52T,F57N,V97N,K99T (SEQ ID NO: 63) | — | nd | nd | nd |
| K45S,K50N,V52T,F57N,V97N,K99T,R186N, K188T (SEQ ID NO: 64) | — | nd | nd | nd |
| K45S,F57N,K94N,E96T,D110N,K112T,R138T,G173T (SEQ ID NO: 65) | + | Yes | 6 | 24 |
| K45S,F57N,T63N,K65T,K94N,E96T,G173T (SEQ ID NO: 66) | + | Yes | 2 | 16 |
| K45N,V47T,K50N,V52T,F57N,V97N,K99T,R138T,R186N,K188T (SEQ ID NO: 67) | — | nd | nd | nd |
| K45S,F57N,T63N,K65T,K94N,E96T,Q126N, R138T (SEQ ID NO: 68) | — | nd | nd | nd |
| K45N,V47T,K50N,V52T,F57N,V97N,K99T,R186N,K188T (SEQ ID NO: 69) | — | nd | nd | nd |
| K45N,V47T,K50N,V52T,V97N,K99T,R138T, R186N,K188T (SEQ ID NO: 70) | — | nd | nd | nd |
| K45S,F57N,H78N,Q80T,K94N,E96T,R138T, G173T (SEQ ID NO: 71) | +++ | Yes | 5 | 18 |
| K45S,F57N,K75N,P77T,K94N,E96T,R138T, G173T (SEQ ID NO: 72) | — | nd | nd | nd |
| K45N,V47T,K50N,V52T,V97N,K99T,G173T, R186N,K188T (SEQ ID NO: 73) | — | nd | nd | nd |

TABLE 3-continued

Expression and activity of TIMP-3 Muteins

| Hyperglycosylation variants | TIMP-3 Mutein Yield[1] | Retains MMP2, 9 or 13 Inhibition[2] | MMP2 Inhibition Shift[3] | MMP9 Inhibition Shift[3] |
|---|---|---|---|---|
| K45E,F57N,Q126N,R138T,G173T (SEQ ID NO: 74) | ++ | Yes | 4 | 8 |
| K45S,F57N,T63N,K65T,K94N,E96T,R138T, G173T (SEQ ID NO: 75) | ++ | Yes | 8 | 16 |
| K45S,K50N,V52T,F57N,V97N,K99T,R138T, R186N,K188T (SEQ ID NO: 76) | — | nd | nd | nd |
| K45S.K50N,V52T,F57N,V97N,K99T,G173T, R186N,K188T (SEQ ID NO: 77) | — | nd | nd | nd |
| K45N, V47T, F57N, K94N, E96T, G173T, R186N, K188T (SEQ ID NO: 78) | — | nd | nd | nd |
| K45N, V47T, F57N, K94N, E96T, D110N, K112T, R186N, K188T (SEQ ID NO: 79) | ++ | Yes | 3 | 8 |
| K45N, V47T, F57N, V97N, K99T, R138T, G173T (SEQ ID NO: 80) | ++ | Yes | 6 | 8 |
| K45N, V47T, F57N, K99E G173T, R186N, K188T (SEQ ID NO: 81) | — | nd | nd | nd |
| K45E, K49E, F57N, K94N, E96T, D110N, K112T, G173T, R186N, K188T (SEQ ID NO: 82) | + | Yes | 1 | 5 |
| K50N, V52T, K94N, E96T, R138T, G173T (SEQ ID NO: 83) | ++ | Yes | 2 | 1 |
| K45E, K50N, V52T, K94N, E96T, D110N, K112T, R138T, G173T (SEQ ID NO: 84) | + | Yes | 2 | 1 |
| K50N, V52T, K94N, E96T, R138T, G173T, R186N, K188T (SEQ ID NO: 85) | — | nd | nd | nd |
| K45E, F57N, T63N, K65T, K94N, E96T, G173T, R186N, K188T (SEQ ID NO: 86) | — | nd | nd | nd |
| K45N, V47T, F57N, K94N, E96T, D110N, K112T, G173T, R186Q, K188Q (SEQ ID NO: 87) | +++ | Yes | 3 | 12 |
| K45S F57N K94N, E96T R138T G173T (SEQ ID NO: 88) | + | tbd | tbd | tbd |
| K45E F57N K94N, E96T R138T G173T (SEQ ID NO: 89) | + | tbd | tbd | tbd |
| K45E F57N K94N, E96T D110N, K112T R138T G173T (SEQ ID NO: 90) | + | tbd | tbd | tbd |
| K45E F57N K94N, E96T R138T G173T R186Q, K188Q (SEQ ID NO: 91) | + | tbd | tbd | tbd |
| K45E F57N K94N, E96T R138T G173T R186E (SEQ ID NO: 92) | + | tbd | tbd | tbd |
| K45E F57N K94N, E96T R138T G173T K188E (SEQ ID NO: 93) | + | tbd | tbd | tbd |
| K45E F57N K94N, E96T R138T G173T R186N, K188T (SEQ ID NO: 94) | — | tbd | tbd | tbd |
| K45E K50N, V52T K94N, E96T D110N, K112T R138T G173T (SEQ ID NO: 95) | + | tbd | tbd | tbd |
| K45E K50N, V52T K94N, E96T R138T G173T K188E (SEQ ID NO: 96) | + | tbd | tbd | tbd |
| K50N, V52T F57N K94N, E96T R138T G173T (SEQ ID NO: 97) | ++ | yes | 2 | 91 |
| K50N, V52T F57N K94N, E96T D110N, K112T R138T (SEQ ID NO: 98) | +++ | yes | 1 | 70 |
| K45E F57N K94N, E96T D110N, K112T R138T (SEQ ID NO: 99) | ++ | yes | 1 | 128 |

[1]yield is relative to the yield of wild-type (WT) TIMP-3; "—" indicates that the expression levels observed were less than the expression levels of wild-type TIMP-3; "+" indicates that the levels observed similar to the expression levels of wild-type TIMP-3; "++" and "+++" indicate expression levels greater than and significantly greater than that of wild-type TIMP-3

[2]activity is within 10-fold of the activity of WTTIMP-3

[3]Shift is the fold decrease (increase) in activity against respective MMP

This Table summarizes glycosylation sites and other characteristics of numerous TIMP-3 muteins that expressed in mammalian cells.

TABLE 4

Glycosylation and Characteristic of TIMP-3 Muteins

| Hyperglycosylation variants | # N-Glyc sites[4] | Heparin Ind.[5] | HTB-94 binding |
|---|---|---|---|
| K45S, F57N, I205F, A208G (SEQ ID NO: 57) | 1* | No | Nd |
| K45S, F57N, A208G (SEQ ID NO: 58) | 1* | No | Nd |
| K45S, F57N, I205Y (SEQ ID NO: 59) | 1* | No | Nd |
| K45S, F57N, I205Y, A208G (SEQ ID NO: 60) | 1* | No | Nd |
| K45N,V47T,F57N,K75N,P77T,K94N,E96T,R138T,G173T (SEQ ID NO: 61) | 6 | Partial | No |
| K45N,V47T,F57N,K94N,E96T,R138T,G173T (SEQ ID NO62): | 5 | Partial | No |
| K45N,V47T,K50N,V52T,F57N,V97N,K99T (SEQ ID NO: 63) | 4 | Partial | nd |
| K45S,K50N,V52T,F57N,V97N,K99T,R186N,K188T (SEQ ID NO: 64) | 4 | Partial | nd |
| K45S,F57N,K94N,E96T,D110N,K112T,R138T,G173T (SEQ ID NO: 65) | 5 | Partial | No |
| K45S,F57N,T63N,K65T,K94N,E96T,G173T (SEQ ID NO: 66) | 4 | Partial | No |
| K45N,V47T,K50N,V52T,F57N,V97N,K99T,R138T,R186N,K188T (SEQ ID NO: 67) | 6 | Partial | nd |
| K45S,F57N,T63N,K65T,K94N,E96T,Q126N,R138T (SEQ ID NO: 68) | 5 | Partial | nd |
| K45N,V47T,K50N,V52T,F57N,V97N,K99T,R186N,K188T (SEQ ID NO: 69) | 5 | Partial | nd |
| K45N,V47T,K50N,V52T,V97N,K99T,R138T,R186N,K188T (SEQ ID NO: 70) | 5 | Partial | nd |
| K45S,F57N,H78N,Q80T,K94N,E96T,R1381,G1731 (SEQ ID NO: 71) | 5 | Partial | No |
| K45S,F57N,K75N,P77T,K94N,E96T,R138T,G173T (SEQ ID NO: 72) | 5 | Partial | nd |
| K45N,V47T,K50N,V52T,V97N,K99T,G173T,R186N,K188T (SEQ ID NO: 73) | 5 | Partial | nd |
| K45E,F57N,Q126N,R138T,G173T (SEQ ID NO: 74) | 4 | Partial | No |
| K45S,F57N,T63N,K65T,K94N,E96T,R138T,G173T (SEQ ID NO: 75) | 5 | Partial | No |
| K45S,K50N,V52T,F57N,V97N,K99T,R138T,R186N,K188T (SEQ ID NO: 76) | 5 | Partial | nd |
| K45S.K50N,V52T,F57N,V97N,K99T,G173T,R186N,K188T (SEQ ID NO: 77) | 5 | Partial | nd |
| K45N, V47T, F57N, K94N, E96T, G173T, R186N, K188T (SEQ ID NO: 78) | 5 | Yes | nd |
| K45N, V47T, F57N, K94N, E96T, D110N, K112T, R186N, K188T (SEQ ID NO: 79) | 5 | Yes | nd |
| K45N, V47T, F57N, V97N, K99T, R138T, G173T (SEQ ID NO: 80) | 5 | Yes | nd |
| K45N, V47T, F57N, K99E G173T, R186N, K188T (SEQ ID NO: 81) | 4 | Yes | nd |
| K45E, K49E, F57N, K94N, E96T, D110N, K112T, G173T, R186N, K188T (SEQ ID NO: 82) | 5 | Yes | No |
| K50N, V52T, K94N, E96T, R138T, G173T (SEQ ID NO: 83) | 4 | Yes | No |
| K45E, K50N, V52T, K94N, E96T, D110N, K112T, R138T, G173T (SEQ ID NO: 84) | 5 | Yes | nd |
| K50N, V52T, K94N, E96T, R138T, G173T, R186N, K188T (SEQ ID NO: 85) | 5 | Yes | nd |
| K45E, F57N ,T63N, K65T, K94N, E96T ,G173T, R186N, K188T (SEQ ID NO: 86) | 5 | Yes | nd |
| K45N, V47T, F57N, K94N, E96T, D110N, K112T, G173T, R186Q, K188Q (SEQ ID NO: 87) | 5 | Yes | nd |
| K45S F57N K94N, E96T R138T G173T (SEQ ID NO: 88) | 4 | tbd | tbd |
| K45E F57N K94N, E96T R138T G173T (SEQ ID NO: 89) | 4 | tbd | tbd |
| K45E F57N K94N, E96T D110N, K112T R138T G173T (SEQ ID NO: 90) | 5 | tbd | tbd |
| K45E F57N K94N, E96T R138T G173T R186Q, K188Q (SEQ ID NO: 91) | 4 | tbd | tbd |
| K45E F57N K94N, E96T R138T G173T R186E (SEQ ID NO: 92) | 4 | tbd | tbd |
| K45E F57N K94N, E96T R138T G173T K188E (SEQ ID NO: 93) | 4 | tbd | tbd |
| K45E F57N K94N, E96T R138T G173T R186N, K188T (SEQ ID NO: 94) | 5 | tbd | tbd |

TABLE 4-continued

| Glycosylation and Characteristic of TIMP-3 Muteins | | | |
|---|---|---|---|
| Hyperglycosylation variants | # N-Glyc sites[4] | Heparin Ind.[5] | HTB-94 binding |
| K45E K50N, V52T K94N, E96T D110N, K112T R138T G173T (SEQ ID NO: 95) | 4 | tbd | tbd |
| K45E K50N, V52T K94N, E96T R138T G173T K188E (SEQ ID NO: 96) | 4 | tbd | tbd |
| K50N, V52T F57N K94N, E96T R138T G173T (SEQ ID NO: 97) | 5 | tbd | tbd |
| K50N, V52T F57N K94N, E96T D110N, K112T R138T (SEQ ID NO: 98) | 5 | tbd | tbd |
| K45E F57N K94N, E96T D110N, K112T R138T (SEQ ID NO: 99) | 4 | tbd | tbd |

[4]Number represents the number of N-glycosylation sites engineered into the mutein, in addition to any native N-glycosylation sites
[5]Heparin independence is a yes/no characteristic that indicates whether a TIMP-3 mutein is secreted into the culture medium in the absence of heparin, as described in Example 2.
*Mutations at residues 208 and/or 205 were made to facilitate glycosylation at the native N-glycosylation site in TIMP-3

Additional muteins are contemplated, including K45S, F57N, D110N, K112T; K45S, F57N, H78N, Q80T, D110N, K112T; K45S, F57N, H78N, Q80T, D110N, K112T, Q126N; K45S, F57N, H78N, Q80T, K94N, E96T Q126N; K45S, F57N, H78N, Q80T, Q126N, G173T; K45S, F57N, T63N, K65T; K45S, F57N, T63N, K65T, K94N, E96T; K45S, F57N, T63N, K65T, R138T, G173T; K45N, V47T, F57N, T63N, K65T, R138T, G173T; K45S, F57N, T63N, K65T, K94N, E96T, R138T; K45N, V47T, F57N, T63N, K65T, K94N, E96T, R138T; K45S, F57N, Q126N, R138T, G173T; P56N, G58T, T63N, K65T, K94N, E96T, Q126N, G173T; P56N, G58T, T63N, K65T, D110N, K112T, Q126N, G173T; K49S, K50N, V52T, K53E, V97N, K99T, R186N, K188T; K50N, V52T, V97N, K99T, R186N, K188T; K49E, K53E, K188Q; K50N, V52T, R186N, K188T; K50N, V52T, F57N, R186N, K188T; K45S, K50N, V52T, F57N, R186N, K188T; K50N, V52T, F57N, T63N, K65T, R186N, K188T; K45S, K50N, V52T, F57N R186N, K188T; K45S, K49S, K50N, V52T, F57N R186N, K188T; K49S, K50N, V52T, F57N, V97N, K99T, R186N, K188T; K45S, K50N, V52T, F57N, V97N, K99T, R186N, K188T; K45E,K50N, V52T, D110N, K112T,R138T,G173T, K188E; K45E, F57N, D110N, K112T,R138T,G173T, K188E; K45E,K50N, V52T, K94N, E96T,D110N, K112T,G173T,K188E; K45E,F57N, K94N, E96T,D110N, K112T,G173T,K188E; K45E,K50N, V52T,D110N, K112T, R138T,G173T,R186N, K188T; K45E,F57N,D110N, K112T,R138T,G173T,R186N, K188T; K45E,K50N, V52T,K94N, E96T,D110N, K112T,G173T, R186N, K188T; K45E,F57N, K94N, E96T,D110N, K112T, G173T,R186N, K188T; K45E,K50N, V52T,D110N, K112T, R138T,G173T,R186Q, K188Q; K45E,F57N,D110N, K112T,R138T,G173T,R186Q, K188Q; K45E,K50N, V52T, K94N, E96T,D110N, K112T,G173T,R186Q, K188Q; K45E, F57N,K94N, E96T,D110N, K112T,G173T,R186Q, K188Q; K45E,K50N, V52T,D110N, K112T,R138T, K188E; K45E, F57N,D110N, K112T,R138T, K188E; K45E,K50N, V52T, K94N, E96T,D110N, K112T,K188E; K45E, F57N,K94N, E96T,D110N, K112T,K188E; K45E,K50N, V52T,D110N, K112T,R138T,R186N, K188T; K45E, F57N,D110N, K112T,R138T,R186N, K188T; K45E,K50N, V52T,K94N, E96T,D110N, K112T,R186N, K188T; K45E, F57N,K94N, E96T,D110N, K112T,R186N, K188T; K45E,K50N, V52T, D110N, K112T,R138T,R186Q, K188Q; K45E, F57N, D110N, K112T,R138T,R186Q, K188Q; K45E,K50N, V52T,K94N, E96T,D110N, K112T,R186Q, K188Q; K45E, F57N,K94N, E96T,D110N, K112T,R186Q, K188Q; K50N, V52T,D110N, K112T,R138T,G173T, K188E; K45S, F57N, D110N, K112T,R138T,G173T, K188E; K50N, V52T,K94N, E96T,D110N, K112T,G173T,K188E; K45S, F57N,K94N, E96T,D110N, K112T,G173T,K188E; K50N, V52T,D110N, K112T,R138T,G173T,R186N, K188T; K45S, F57N,D110N, K112T,R138T,G173T,R186N, K188T; K50N, V52T,K94N, E96T,D110N, K112T,G173T,R186N, K188T; K45S, F57N, K94N, E96T,D110N, K112T,G173T,R186N, K188T; K50N, V52T,D110N, K112T,R138T,G173T,R186Q, K188Q; K45S, F57N,D110N, K112T,R138T,G173T,R186Q, K188Q; K50N, V52T,K94N, E96T,D110N, K112T,G173T, R186Q, K188Q; K45S, F57N,K94N, E96T,D110N, K112T, G173T,R186Q, K188Q; K50N, V52T,D110N, K112T, R138T,K188E; K45S, F57N,D110N, K112T,R138T,K188E; K50N, V52T,K94N, E96T,D110N, K112T,K188E; K45S, F57N,K94N, E96T,D110N, K112T,K188E; K50N, V52T, D110N, K112T,R138T,R186N, K188T; K45S, F57N, D110N, K112T,R138T,R186N, K188T; K50N, V52T,K94N, E96T,D110N, K112T,R186N, K188T; K45S, F57N,K94N, E96T,D110N, K112T,R186N, K188T; K50N, V52T,D110N, K112T,R138T,R186Q, K188Q; K45S, F57N,D110N, K112T,R138T,R186Q, K188Q; K50N, V52T,K94N, E96T, D110N, K112T,R186Q, K188Q; K45S, F57N,K94N, E96T, D110N, K112T,R186Q, K188Q; K50N, V52T,K94N, E96T, D110N, K112T,R138T,G173T; K50N, V52T,K94N, E96T, R138T,G173T; K45E, F57N,K94N, E96T,D110N, K112T, R138T,G173T; K45E, F57N,K94N, E96T,R138T,G173T; K45S, F57N,K94N, E96T,D110N, K112T,R138T,G173T; K45S, F57N,K94N, E96T,R138T,G173T; K45N,V47T, H78N,Q80T, Q126N, R186Q, K188Q; K45N,V47T, F57N, H78N,Q80T, Q126N, R186Q,K188Q; K45N,V47T, F57N, H78N,Q80T, K94N,E96T, Q126N; K45N,V47T, F57N, H78N,Q80T, Q126N, R138T; K45N,V47T, F57N, H78N, Q80T, R138T, R186Q,K188Q; K45N,V47T, F57N, H78N, Q80T, K94N,E96T, D110N,K112T, R186Q,K188Q; K50N, V52T, K94N,E96T, H78N,Q80T, R138T; K50N,V52T, K94N,E96T, H78N,Q80T, R138T, R186Q,K188Q; K45E, F57N, Q126N, R138T, R186Q,K188Q; K45N,V47T, F57N, Q126N, R138T, R186Q,K188Q; K45N,V47T, F57N, H78N, Q80T, R186Q,K188Q; K45S, F57N, H78N,Q80T, Q126N, R138T, R186Q,K188Q; K45S, F57N, H78N,Q80T, K94N, E96T, R138T, R186Q,K188Q; K50N,V52T, K94N,E96T, H78N,Q80T, R138T; K45N,V47T, F57N, K94N,E96T, D110N,K112T, R186Q,K188Q; K45S, F57N, H78N,Q80T, K94N,E96T, R138T; K45N,V47T, F57N, K94N,E96T, D110N,K112T, R186Q; and K45N,V47T, F57N, K94N, E96T, D110N,K112T, K188Q. Further muteins include K50N, V52T, P56N, G58T, R186N, K188T; K45S, K50N, V52T, P56N, G58T, R186N, K188T; K50N, V52T, P56N, G58T, T63N, K65T, R186N, K188T; K45S, K50N, V52T, P56N, G58T R186N, K188T; K45S, K49S, K50N, V52T, P56N, G58T R186N, K188T; K49S, K50N, V52T, P56N, G58T, V97N, K99T, R186N, K188T; K45S, K50N, V52T, P56N, G58T, V97N, K99T, R186N, K188T; K45E, P56N, G58T,D110N, K112T,R138T,G173T, K188E; K45E,P56N, G58T,K94N, E96T,D110N, K112T,G173T,K188E; K45E, K50N, V52T,D110N, K112T, R138T,G173T,R186N, K188T; K45E,P56N, G58T,D110N, K112T,R138T,G173T, R186N, K188T; K45E,P56N, G58T, K94N, E96T,D110N, K112T,G173T,R186N, K188T; K45E,P56N, G58T,D110N, K112T,R138T,G173T,R186Q, K188Q; K45E, P56N, G58T, K94N, E96T,D110N, K112T,G173T,R186Q, K188Q; K45E, P56N, G58T,D110N, K112T,R138T, K188E; K45E, P56N, G58T,K94N, E96T,D110N, K112T,K188E; K45E, P56N, G58T,D110N, K112T,R138T,R186N, K188T; K45E, P56N, G58T,K94N, E96T,D110N, K112T,R186N, K188T; K45E, P56N, G58T,D110N, K112T,R138T,R186Q, K188Q; K45E, P56N, G58T,K94N, E96T,D110N, K112T,R186Q, K188Q; K45S, K45S, P56N, G58T,D110N, K112T,R138T,G173T, K188E; K45S, P56N, G58T,K94N, E96T,D110N, K112T,G173T, K188E; K45S, P56N, G58T,D110N, K112T,R138T,G173T, R186N, K188T; K45S, P56N, G58T,K94N, E96T,D110N, K112T,G173T,R186N, K188T; K45S, P56N, G58T,D110N, K112T,R138T,G173T,R186Q, K188Q; K45S, P56N, G58T, K94N, E96T,D110N, K112T,G173T,R186Q, K188Q; K45S, P56N, G58T,D110N, K112T,R138T,K188E; K45S, P56N, G58T,K94N, E96T,D110N, K112T,K188E; K45S, P56N, G58T,D110N, K112T,R138T,R186N, K188T; K45S, P56N, G58T,K94N, E96T,D110N, K112T,R186N, K188T; K45S, P56N, G58T,D110N, K112T,R138T,R186Q, K188Q; K45S, P56N, G58T,K94N, E96T,D110N, K112T,R186Q, K188Q; K45E, P56N, G58T,K94N, E96T,D110N, K112T,R138T, G173T; K45E, P56N, G58T,K94N, E96T,R138T,G173T; K45S, P56N, G58T,K94N, E96T,D110N, K112T,R138T, G173T; K45S, P56N, G58T,K94N, E96T,R138T,G173T; K45N,V47T, P56N, G58T, H78N,Q80T, Q126N, R186Q, K188Q; K45N,V47T, P56N, G58T, H78N,Q80T, K94N, E96T, Q126N; K45N,V47T, P56N, G58T, H78N,Q80T, Q126N, R138T; K45N,V47T, P56N, G58T, H78N,Q80T, R138T, R186Q,K188Q; K45N,V47T, P56N, G58T, H78N, Q80T, K94N,E96T, D110N,K112T, R186Q,K188Q; K45E, P56N, G58T, Q126N, R138T, R186Q,K188Q; K45N,V47T, P56N, G58T, Q126N, R138T, R186Q,K188Q; K45N,V47T, P56N, G58T, H78N,Q80T, R186Q,K188Q; K45S, P56N, G58T, H78N,Q80T, Q126N, R138T, R186Q,K188Q; K45S, P56N, G58T, H78N,Q80T, K94N,E96T, R138T, R186Q, K188Q; K45N,V47T, P56N, G58T, K94N,E96T, D110N, K112T, R186Q,K188Q; K45S, P56N, G58T, H78N,Q80T, K94N,E96T, R138T; K45N,V47T, P56N, G58T, K94N, E96T, D110N,K112T, R186Q; and K45N,V47T, P56N, G58T, K94N,E96T, D110N,K112T, K188Q. These muteins can be made and tested as described herein.

What is claimed is:

1. An isolated TIMP-3 mutein having a mature region that comprises the amino acid sequence of the mature region of TIMP-3 set forth in SEQ ID NO:2, wherein the mutein has (a) a mutation K45S, and (b) a mutation F57N.

2. A composition comprising the TIMP-3 mutein of claim 1 and a physiologically acceptable diluent, excipient or carrier.

3. An isolated nucleic acid that encodes a TIMP-3 mutein according to claim 1.

4. An expression vector comprising the isolated nucleic acid of claim 3.

5. An isolated host cell transformed or transfected with the expression vector of claim 4.

6. A method of producing a recombinant TIMP-3 mutein comprising culturing the transformed or transfected host cell of claim 5 under conditions promoting expression of the TIMP-3 mutein, and recovering the TIMP-3 mutein.

* * * * *